(12) United States Patent
DiNardo et al.

(10) Patent No.: US 10,905,415 B2
(45) Date of Patent: Feb. 2, 2021

(54) SURGICAL STAPLER WITH ELECTROMECHANICAL LOCKOUT

(71) Applicant: Ethicon Endo-Surgery, LLC, Guaynabo, PR (US)

(72) Inventors: Brian F. DiNardo, Cincinnati, OH (US); Christopher C. Miller, Loveland, OH (US); Richard F. Schwemberger, Cincinnati, OH (US); Charles J. Scheib, Loveland, OH (US); Kevin L. Houser, Springboro, OH (US); Frederick E. Shelton, IV, Hillsboro, OH (US)

(73) Assignee: Ethicon LLC, Guaynabo, PR (US)

( * ) Notice: Subject to any disclaimer, the term of this patent is extended or adjusted under 35 U.S.C. 154(b) by 1267 days.

(21) Appl. No.: 14/751,215

(22) Filed: Jun. 26, 2015

(65) Prior Publication Data
US 2016/0374665 A1 Dec. 29, 2016

(51) Int. Cl.
*A61B 17/068* (2006.01)
*A61B 17/115* (2006.01)
(Continued)

(52) U.S. Cl.
CPC ...... *A61B 17/068* (2013.01); *A61B 17/07207* (2013.01); *A61B 17/1155* (2013.01);
(Continued)

(58) Field of Classification Search
None
See application file for complete search history.

(56) References Cited

U.S. PATENT DOCUMENTS

| 5,205,459 A | 4/1993 | Brinkerhoff et al. |
| 5,271,544 A | 12/1993 | Fox et al. |

(Continued)

FOREIGN PATENT DOCUMENTS

EP 2 090 241 A1 8/2009

OTHER PUBLICATIONS

Brazilian Office Action dated May 28, 2020 for Application No. BR112017028118-0, 4 pgs.

(Continued)

*Primary Examiner* — Michelle Lopez
*Assistant Examiner* — Chinyere J Rushing-Tucker
(74) *Attorney, Agent, or Firm* — Frost Brown Todd LLC

(57) ABSTRACT

A surgical instrument includes a body, a shaft assembly, a stapling head assembly, an anvil, an anvil adjustment assembly, a trigger, and a lockout assembly. The stapling head assembly is operable to drive an annular array of staples. The anvil is configured to couple with the stapling head assembly. The anvil adjustment assembly includes a translating member, which translates relative to the body to thereby adjust the longitudinal position of the anvil relative to the stapling head assembly. The trigger is operable to actuate the stapling head assembly to thereby drive the annular array of staples through a distal surface of the stapling head assembly toward the anvil. The lockout assembly includes an electrically powered braking feature. In a first state, the lockout assembly is configured to permit translation of the translating member. In a second state, the lockout assembly is configured to prevent translation of the translating member.

20 Claims, 51 Drawing Sheets

(51) Int. Cl.
   *A61B 17/072* (2006.01)
   *A61B 17/11* (2006.01)
   *A61B 17/00* (2006.01)
   *A61B 90/00* (2016.01)

(52) U.S. Cl.
   CPC . *A61B 17/1114* (2013.01); *A61B 2017/00017* (2013.01); *A61B 2017/00022* (2013.01); *A61B 2017/00398* (2013.01); *A61B 2017/00818* (2013.01); *A61B 2017/00876* (2013.01); *A61B 2017/1132* (2013.01); *A61B 2090/0811* (2016.02)

(56) References Cited

U.S. PATENT DOCUMENTS

| | | | |
|---|---|---|---|
| 5,275,322 A | | 1/1994 | Wolf et al. |
| 5,285,945 A | | 2/1994 | Brinkerhoff et al. |
| 5,292,053 A | | 3/1994 | Smith et al. |
| 5,333,773 A | | 8/1994 | Main et al. |
| 5,350,104 A | * | 9/1994 | Main ............... A61B 17/115 227/179.1 |
| 5,533,661 A | | 7/1996 | Main et al. |
| 6,716,233 B1 | * | 4/2004 | Whitman ......... A61B 17/07207 606/219 |
| 6,945,444 B2 | | 9/2005 | Gresham et al. |
| 7,794,475 B2 | | 9/2010 | Hess et al. |
| 8,408,439 B2 | | 4/2013 | Huang et al. |
| 8,453,914 B2 | | 6/2013 | Laurent et al. |
| 8,646,674 B2 | | 2/2014 | Schulte et al. |
| 8,910,847 B2 | | 12/2014 | Nalagatla et al. |
| 8,979,827 B2 | | 3/2015 | Cappola |
| 9,161,803 B2 | | 10/2015 | Yates et al. |
| 9,220,505 B2 | | 12/2015 | Vasudevan et al. |
| 9,445,816 B2 | | 9/2016 | Swayze et al. |
| 9,603,599 B2 | | 3/2017 | Miller et al. |
| 9,907,552 B2 | | 3/2018 | Measamer et al. |
| 2006/0097025 A1 | * | 5/2006 | Milliman ............ A61B 17/115 227/175.1 |
| 2009/0206132 A1 | * | 8/2009 | Hueil ............ A61B 17/07207 227/175.2 |
| 2010/0237132 A1 | * | 9/2010 | Measamer ......... A61B 17/115 227/180.1 |
| 2013/0153630 A1 | * | 6/2013 | Miller ............... A61B 17/115 227/175.2 |
| 2013/0153631 A1 | * | 6/2013 | Vasudevan .......... A61B 17/115 227/175.2 |
| 2013/0175320 A1 | * | 7/2013 | Mandakolathur Vasudevan ........ A61B 17/072 227/175.2 |
| 2014/0005654 A1 | * | 1/2014 | Batross ......... A61B 17/320092 606/33 |
| 2014/0144968 A1 | | 5/2014 | Shelton |
| 2014/0144969 A1 | | 5/2014 | Scheib et al. |
| 2014/0151429 A1 | | 6/2014 | Scheib et al. |
| 2014/0151430 A1 | | 6/2014 | Scheib et al. |
| 2014/0158747 A1 | | 6/2014 | Measamer et al. |
| 2014/0166717 A1 | | 6/2014 | Swayze et al. |
| 2014/0166718 A1 | | 6/2014 | Swayze et al. |
| 2014/0166728 A1 | | 6/2014 | Swayze et al. |
| 2014/0305992 A1 | * | 10/2014 | Kimsey ............... A61B 17/068 227/176.1 |
| 2014/0305994 A1 | * | 10/2014 | Parihar ............... A61B 17/068 227/180.1 |
| 2015/0083772 A1 | | 3/2015 | Miller et al. |
| 2015/0083773 A1 | | 3/2015 | Measamer et al. |
| 2015/0083774 A1 | * | 3/2015 | Measamer .......... A61B 17/068 227/175.1 |
| 2015/0083775 A1 | * | 3/2015 | Leimbach .......... A61B 17/1155 227/175.1 |

OTHER PUBLICATIONS

Chinese Office Action, Notification of the First Office Action, and Search Report dated Mar. 27, 2020 for Application No. CN 201680037752, 10 pgs.
European Search Report and Written Opinion dated Sep. 23, 2016 for Application No. EP16176137.4, 9 pgs.
International Search Report and Written Opinion dated Sep. 7, 2016 for Application No. PCT/US2016/038863, 12 pgs.
Japanese Office Action, Notice of Reason for Refusal, and Search Report by Registered Search Organization dated Mar. 10, 2020 for Application No. JP 2017-567147, 30 pgs.

* cited by examiner

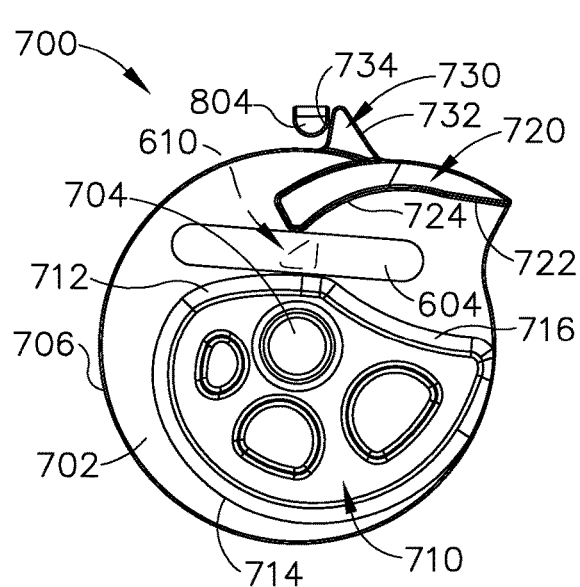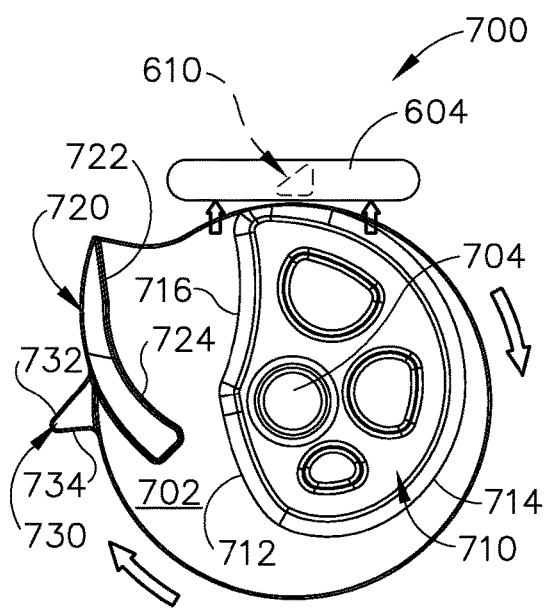
Fig.20A  Fig.20B
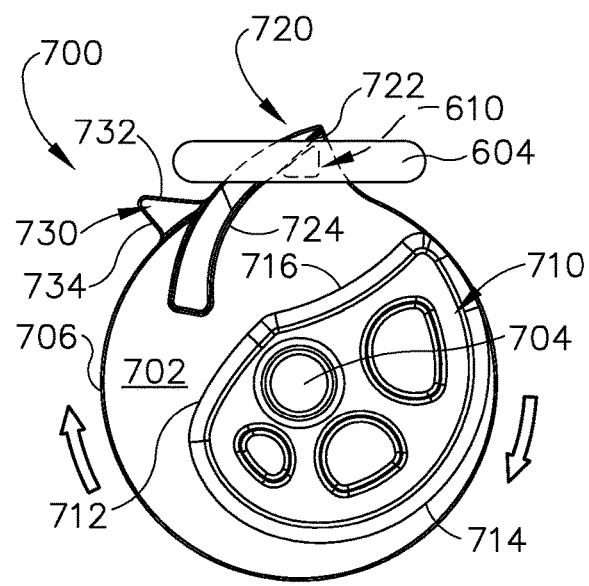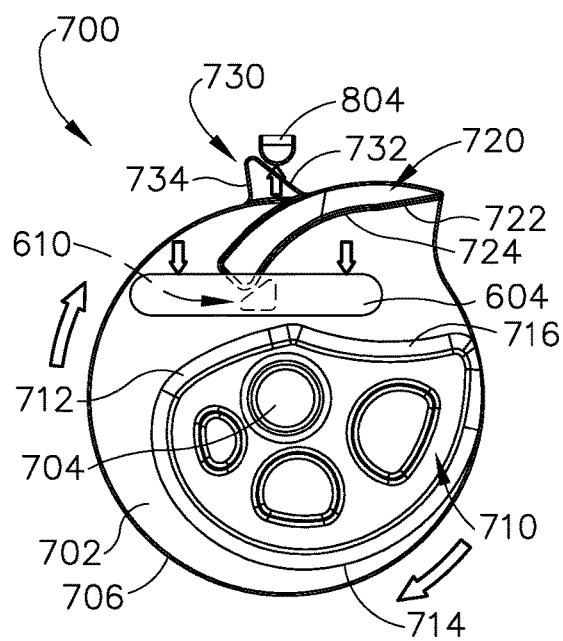
Fig.20C  Fig.20D

SURGICAL STAPLER WITH ELECTROMECHANICAL LOCKOUT

BACKGROUND

In some surgical procedures (e.g., colorectal, bariatric, thoracic, etc.), portions of a patient's digestive tract (e.g., the gastrointestinal tract and/or esophagus, etc.) may be cut and removed to eliminate undesirable tissue or for other reasons. Once the tissue is removed, the remaining portions of the digestive tract may be coupled together in an end-to-end anastomosis. The end-to-end anastomosis may provide a substantially unobstructed flow path from one portion of the digestive tract to the other portion of the digestive tract, without also providing any kind of leaking at the site of the anastomosis.

One example of an instrument that may be used to provide an end-to-end anastomosis is a circular stapler. Some such staplers are operable to clamp down on layers of tissue, cut through the clamped layers of tissue, and drive staples through the clamped layers of tissue to substantially seal the layers of tissue together near the severed ends of the tissue layers, thereby joining the two severed ends of the anatomical lumen together. The circular stapler may be configured to sever the tissue and seal the tissue substantially simultaneously. For instance, the circular stapler may sever excess tissue that is interior to an annular array of staples at an anastomosis, to provide a substantially smooth transition between the anatomical lumen sections that are joined at the anastomosis. Circular staplers may be used in open procedures or in endoscopic procedures. In some instances, a portion of the circular stapler is inserted through a patient's naturally occurring orifice.

Examples of circular staplers are described in U.S. Pat. No. 5,205,459, entitled "Surgical Anastomosis Stapling Instrument," issued Apr. 27, 1993; U.S. Pat. No. 5,271,544, entitled "Surgical Anastomosis Stapling Instrument," issued Dec. 21, 1993; U.S. Pat. No. 5,275,322, entitled "Surgical Anastomosis Stapling Instrument," issued Jan. 4, 1994; U.S. Pat. No. 5,285,945, entitled "Surgical Anastomosis Stapling Instrument," issued Feb. 15, 1994; U.S. Pat. No. 5,292,053, entitled "Surgical Anastomosis Stapling Instrument," issued Mar. 8, 1994; U.S. Pat. No. 5,333,773, entitled "Surgical Anastomosis Stapling Instrument," issued Aug. 2, 1994; U.S. Pat. No. 5,350,104, entitled "Surgical Anastomosis Stapling Instrument," issued Sep. 27, 1994; and U.S. Pat. No. 5,533,661, entitled "Surgical Anastomosis Stapling Instrument," issued Jul. 9, 1996; and U.S. Pat. No. 8,910,847, entitled "Low Cost Anvil Assembly for a Circular Stapler," issued Dec. 16, 2014. The disclosure of each of the above-cited U.S. patents is incorporated by reference herein.

Some circular staplers may include a motorized actuation mechanism. Examples of circular staplers with motorized actuation mechanisms are described in U.S. Pub. No. 2015/0083772, entitled "Surgical Stapler with Rotary Cam Drive and Return," published Mar. 26, 2015, now abandoned; U.S. Pub. No. 2015/0083773, entitled "Surgical Stapling Instrument with Drive Assembly Having Toggle Features," published Mar. 26, 2015, issued as U.S. Pat. No. 9,936,949 on Apr. 10, 2018; U.S. Pub. No. 2015/0083774, entitled "Control Features for Motorized Surgical Stapling Instrument," published Mar. 26, 2015, issued as U.S. Pat. No. 9,907,552 on Mar. 6, 2018; and U.S. Pub. No. 2015/0083775, entitled "Surgical Stapler with Rotary Cam Drive," published Mar. 26, 2015, issued as U.S. Pat. No. 9,713,469 on Jul. 25, 2017. The disclosure of each of the above-cited U.S. patent Publications is incorporated by reference herein.

While various kinds of surgical stapling instruments and associated components have been made and used, it is believed that no one prior to the inventor(s) has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

FIG. 20A depicts a schematic end view of the rotary cam of FIG. 16, the cam follower of FIG. 14, and the rocker member of FIG. 19A, with the rotary cam in the first angular position, the cam follower in the first pivotal position, and the rocker member in the first pivotal position;

FIG. 20B depicts a schematic end view of the rotary cam of FIG. 16 and the cam follower of FIG. 14, with the rotary cam in the second angular position, the cam follower in the second pivotal position, and the rocker member of FIG. 19A in the first pivotal position;

FIG. 20C depicts a schematic end view of the rotary cam of FIG. 16 and the cam follower of FIG. 14, with the rotary cam in a third angular position, the cam follower in the second pivotal position, and the rocker member of FIG. 19A in the first pivotal position;

FIG. 20D depicts a schematic end view of the rotary cam of FIG. 16, the cam follower of FIG. 14, and the rocker member of FIG. 19A, with the rotary cam in a fourth angular position, the cam follower in a third pivotal position, and the rocker member in a second pivotal position;

Figure 1:
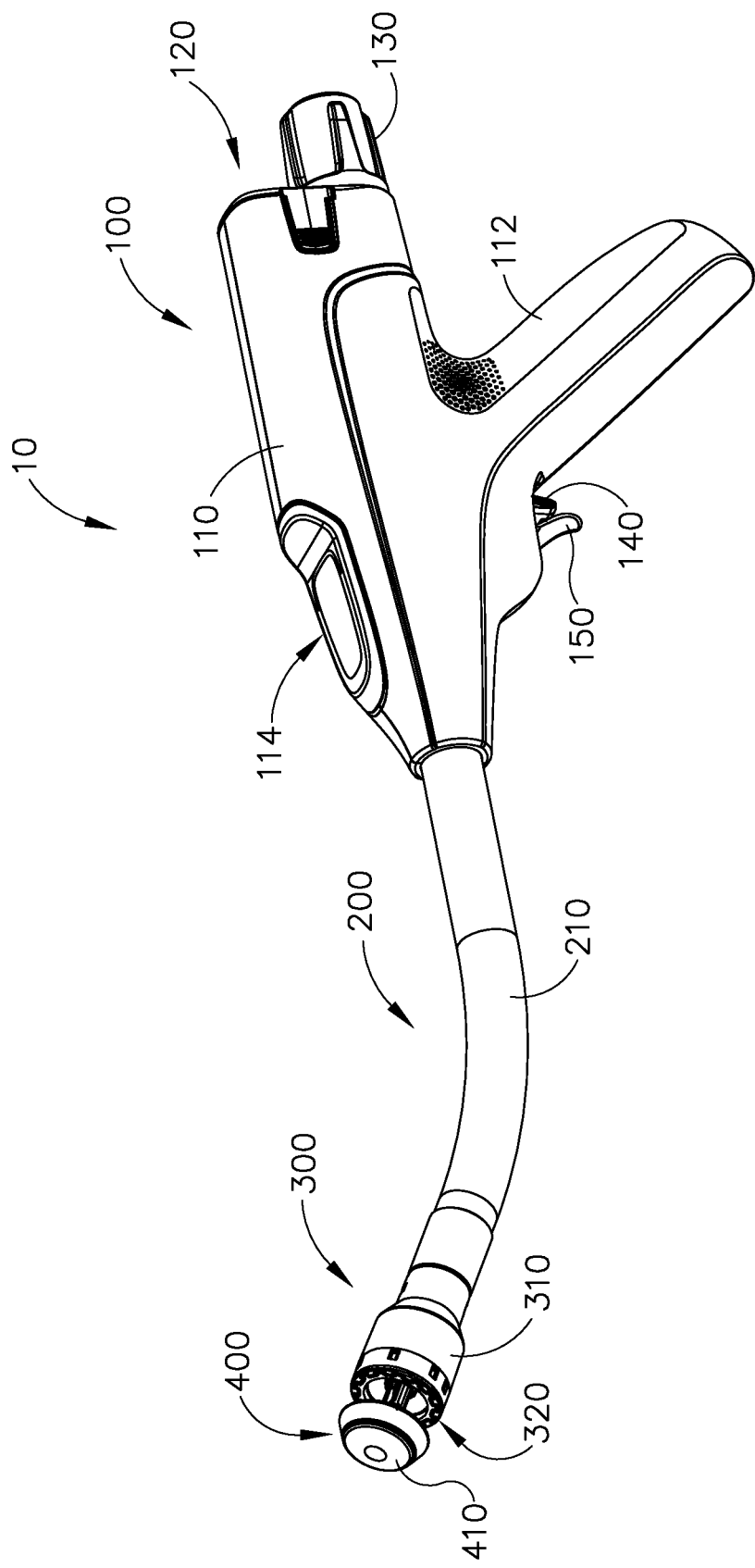
FIG. 1 depicts a perspective view of an exemplary circular stapler.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

I. Overview of Exemplary Circular Stapling Surgical Instrument

Figure 2:
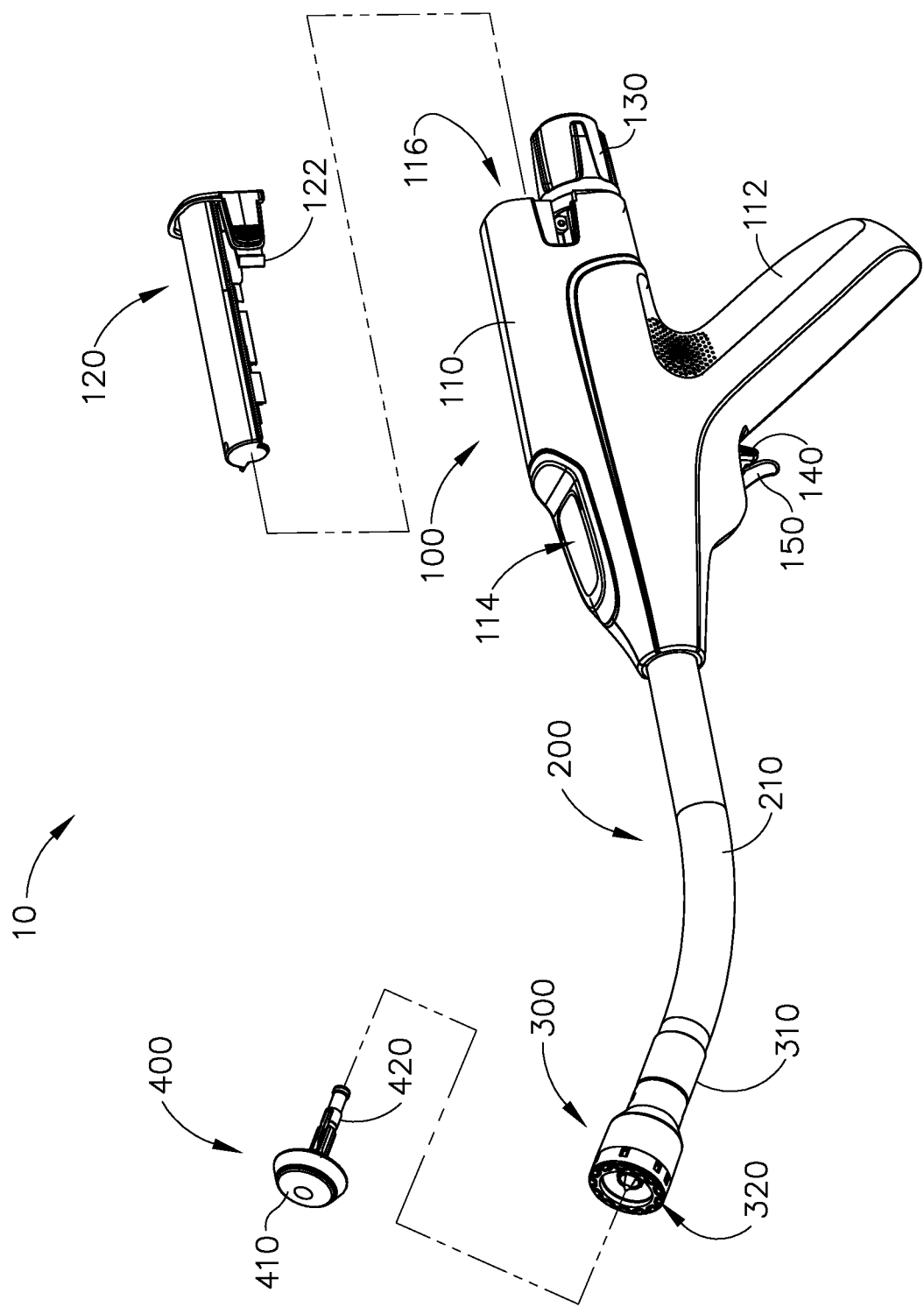
FIG. 2 depicts a perspective view of the circular stapler of FIG. 1, with a battery pack removed from a handle assembly and an anvil removed from a stapling head assembly.

FIGS. 1-2 depict an exemplary surgical circular stapling instrument (10) that may be used to provide an end-to-end anastomosis between two sections of an anatomical lumen such as a portion of a patient's digestive tract. Instrument (10) of this example comprises a handle assembly (100), a shaft assembly (200), a stapling head assembly (300), and an anvil (400). Handle assembly (100) comprises a casing (110) defining an obliquely oriented pistol grip (112). In some versions, pistol grip (112) is perpendicularly oriented. In some other versions, pistol grip (112) is omitted. Handle assembly (110) further includes a window (114) that permits viewing of a movable indicator needle (526) as will be described in greater detail below. In some versions, a series of hash marks, colored regions, and/or other fixed indicators are positioned adjacent to window (114) in order to provide a visual context for indicator needle (526), thereby facilitating operator evaluation of the position of needle (526) within window (114). Various suitable alternative features and configurations for handle assembly (112) will be apparent to those of ordinary skill in the art in view of the teachings herein.

Instrument (10) of the present example further includes a battery pack (120). Battery pack (120) is operable to provide electrical power to a motor (160) in pistol grip (112) as will be described in greater detail below. Battery pack (120) is removable from handle assembly (100). In particular, as shown in FIGS. 1-2, battery pack (120) may be inserted into a socket (116) defined by casing (110). Once battery pack (120) is fully inserted in socket (116), latches (122) of battery pack (120) may resiliently engage interior features of casing (110) to provide a snap fit. To remove battery pack (120), the operator may press latches (122) inwardly to disengage latches (122) from the interior features of casing (110) then pull battery pack (120) proximally from socket (116). It should be understood that battery pack (120) and handle assembly (100) may have complementary electrical contacts, pins and sockets, and/or other features that provide paths for electrical communication from battery pack (120) to electrically powered components in handle assembly (100) when battery pack (120) is inserted in socket (116). It should also be understood that, in some versions, battery pack (120) is unitarily incorporated within handle assembly (100) such that battery back (120) cannot be removed from handle assembly (100).

Shaft assembly (200) extends distally from handle assembly (100) and includes a preformed bend. In some versions, the preformed bend is configured to facilitate positioning of stapling head assembly (300) within a patient's colon. Various suitable bend angles or radii that may be used will be apparent to those of ordinary skill in the art in view of the teachings herein. In some other versions, shaft assembly (200) is straight, such that shaft assembly (200) lacks a preformed bend. Various exemplary components that may be incorporated into shaft assembly (100) will be described in greater detail below.

Stapling head assembly (300) is located at the distal end of shaft assembly (200). As shown in FIGS. 1-2 and as will be described in greater detail below, anvil (400) is configured to removably couple with shaft assembly (200), adjacent to stapling head assembly (300). As will also be described in greater detail below, anvil (400) and stapling head assembly (300) are configured to cooperate to manipulate tissue in three ways, including clamping the tissue, cutting the tissue, and stapling the tissue. A knob (130) at the proximal end of handle assembly (100) is rotatable relative to casing (110) to provide precise clamping of the tissue between anvil (400) and stapling head assembly (300). When a safety trigger (140) of handle assembly (100) is pivoted away from a firing trigger (150) of handle assembly (100), firing trigger (150) may be actuated to thereby provide cutting and stapling of the tissue.

A. Exemplary Anvil

In the following discussion of anvil (400), the terms "distal" and "proximal" (and variations thereof) will be used with reference to the orientation of anvil (400) when anvil (400) is coupled with shaft assembly (200) of instrument (10). Thus, proximal features of anvil (400) will be closer to the operator of instrument (10); while distal features of anvil (400) will be further from the operator of instrument (10).

Figure 3:
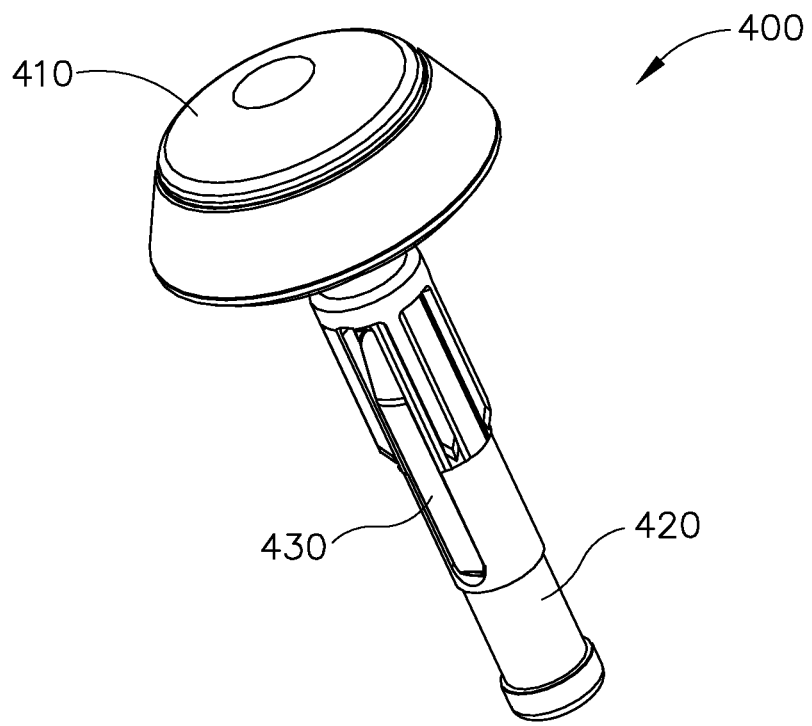
FIG. 3 depicts a perspective view of the anvil of the circular stapler of FIG. 1.
Figure 4:
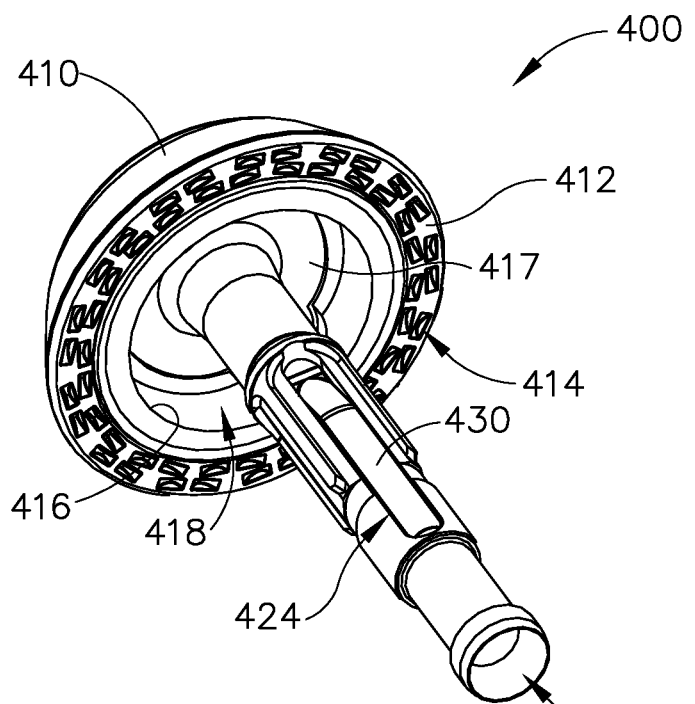
FIG. 4 depicts another perspective view of the anvil of FIG. 3.
Figure 5:
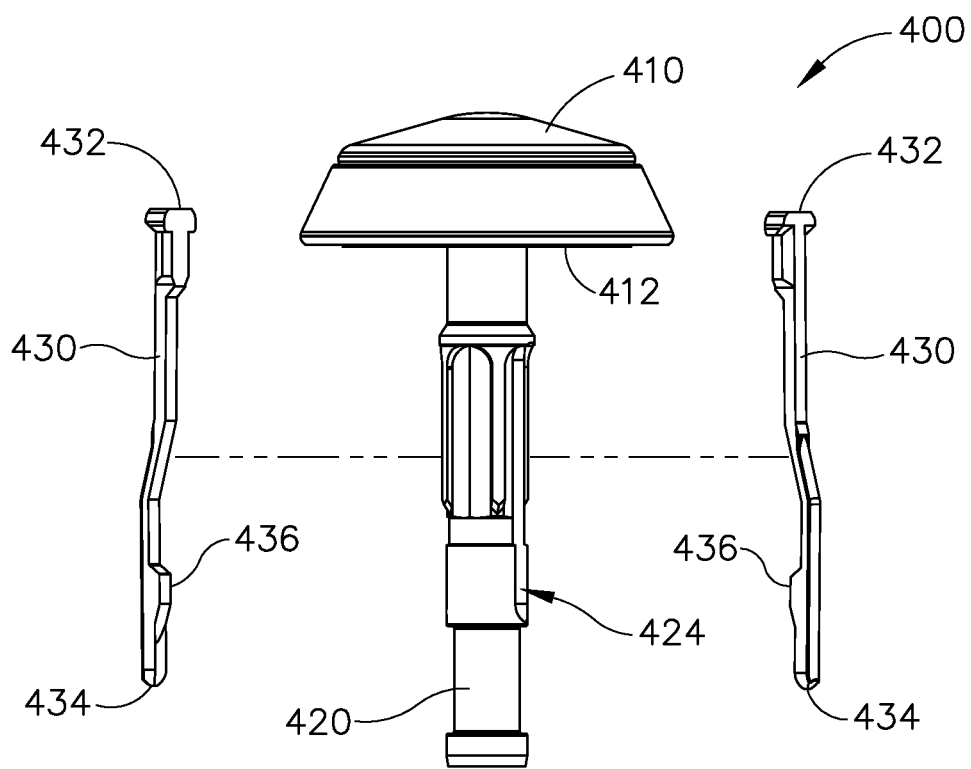
FIG. 5 depicts an exploded side elevational view of the anvil of FIG. 3.

As best seen in FIGS. 3-5, anvil (400) of the present example comprises a head (410) and a shank (420). Head (410) includes a proximal surface (412) that defines a plurality of staple forming pockets (414). Staple forming pockets (414) are arranged in two concentric annular arrays. In some other versions, staple forming pockets (414) are arranged in three or more concentric annular arrays. Staple forming pockets (414) are configured to deform staples as the staples are driven into staple forming pockets (414). For instance, each staple forming pocket (414) may deform a generally "U" shaped staple into a "B" shape as is known in the art. As best seen in FIG. 4, proximal surface (412) terminates at an inner edge (416), which defines an outer boundary of an annular recess (418) surrounding shank (420).

Shank (420) defines a bore (422) and includes a pair of pivoting latch members (430) positioned in bore (422). As best seen in FIG. 5, each latch member (430) includes a "T" shaped distal end (432), a rounded proximal end (434), and a latch shelf (436) located distal to proximal end (434). "T" shaped distal ends (432) secure latch members (430) within bore (422). Latch members (430) are positioned within bore (422) such that distal ends (434) are positioned at the proximal ends of lateral openings (424), which are formed through the sidewall of shank (420). Lateral openings (424) thus provide clearance for distal ends (434) and latch shelves (436) to deflect radially outwardly from the longitudinal axis defined by shank (420). However, latch members (430) are configured to resiliently bias distal ends (434) and latch shelves (436) to radially inwardly toward the longitudinal axis defined by shank (420). Latch members (430) thus act as retaining clips. This allows anvil (400) to be removably secured to a trocar (330) of stapling head assembly (300) as will be described in greater detail below. It should be understood, however, that latch members (436) are merely optional. Anvil (400) may be removably secured to a trocar (330) using any other suitable components, features, or techniques.

In addition to or in lieu of the foregoing, anvil (400) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

B. Exemplary Stapling Head Assembly

Figure 6:
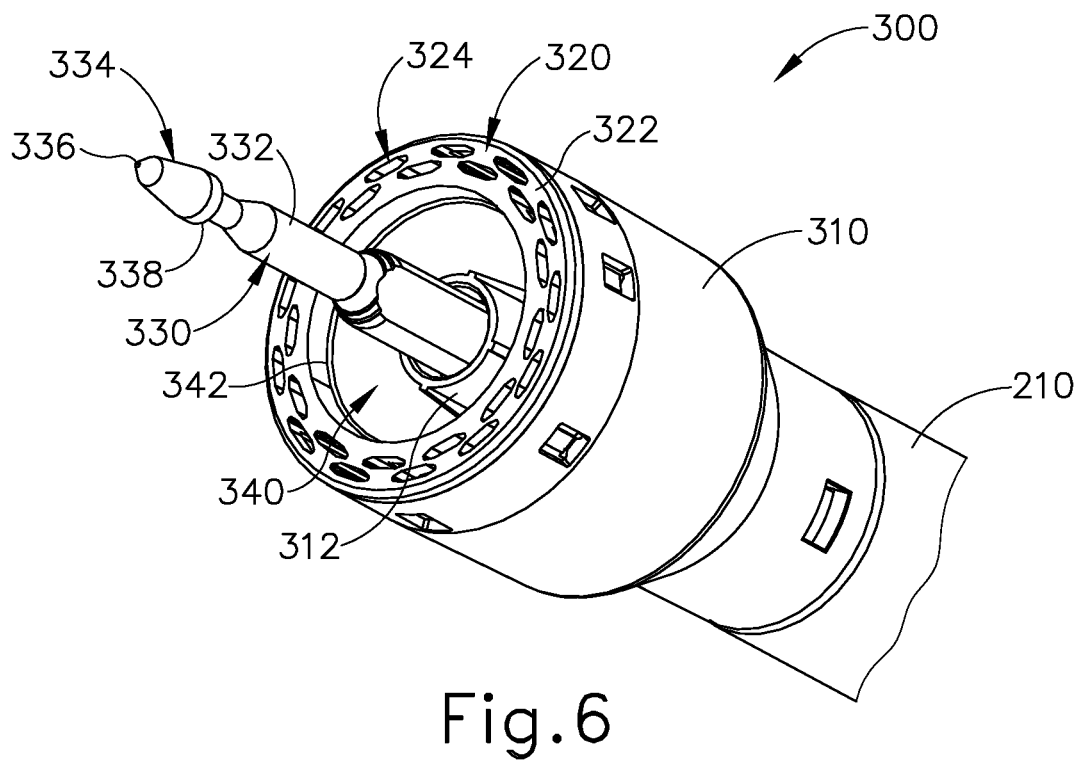
FIG. 6 depicts a perspective view of the stapling head assembly of the circular stapler of FIG. 1.
Figure 7:
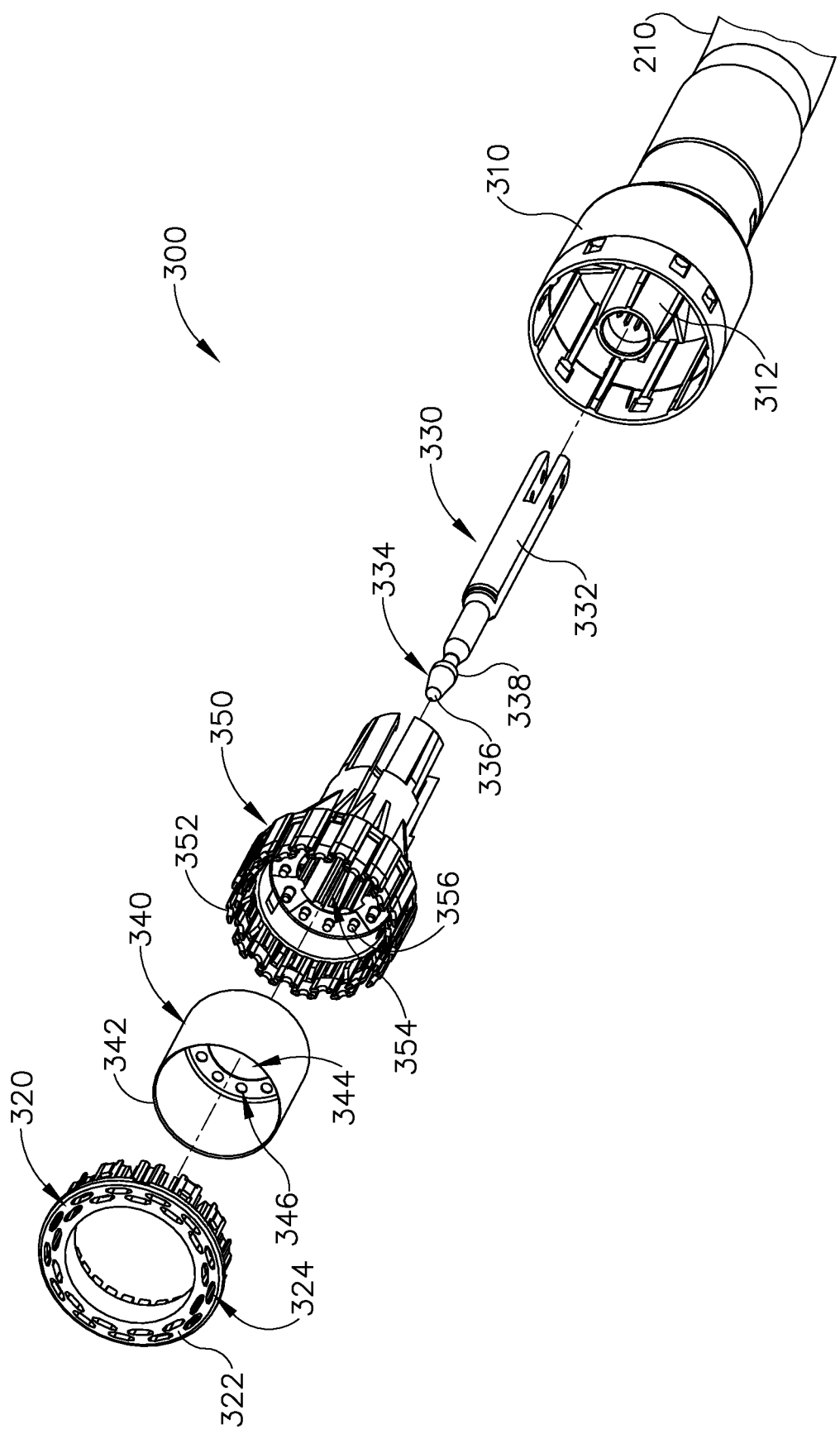
FIG. 7 depicts an exploded perspective view of the stapling head assembly of FIG. 6.

As best seen in FIGS. 6-7, stapling head assembly (300) of the present example is coupled to a distal end of shaft assembly (200) and comprises a tubular casing (310) housing a slidable staple driver member (350). A cylindraceous inner core member (312) extends distally within tubular casing (310). Tubular casing (310) is fixedly secured to an outer sheath (210) of shaft assembly (200), such that tubular casing (310) serves as a mechanical ground for stapling head assembly (300).

Trocar (330) is positioned coaxially within inner core member (312) of tubular casing (310). As will be described in greater detail below, trocar (330) is operable to translate distally and proximally relative to tubular casing (310) in response to rotation of knob (130) relative to casing (110) of handle assembly (100). Trocar (330) comprises a shaft (332) and a head (334). Head (334) includes a pointed tip (336) and an inwardly extending proximal surface (338). Shaft (332) thus provides a reduced outer diameter just proximal to head (334), with surface (338) providing a transition between that reduced outer diameter of shaft (332) and the outer diameter of head (334). While tip (336) is pointed in the present example, tip (336) is not sharp. Tip (336) will thus not easily cause trauma to tissue due to inadvertent contact with tissue. Head (334) and the distal portion of shaft (332) are configured for insertion in bore (422) of anvil (420). Proximal surface (338) and latch shelves (436) have complementary positions and configurations such that latch shelves (436) engage proximal surface (338) when shank (420) of anvil (400) is fully seated on trocar (330). Anvil (400) is thus secured to trocar (330) through a snap fit due to latch members (430).

Staple driver member (350) is operable to actuate longitudinally within tubular casing (310) in response to activation of motor (160) as will be described in greater detail below. Staple driver member (350) includes two distally presented concentric annular arrays of staple drivers (352). Staple drivers (352) are arranged to correspond with the arrangement of staple forming pockets (414) described above. Thus, each staple driver (352) is configured to drive a corresponding staple into a corresponding staple forming pocket (414) when stapling head assembly (300) is actuated. It should be understood that the arrangement of staple drivers (352) may be modified just like the arrangement of staple forming pockets (414) as described above. Staple driver member (350) also defines a bore (354) that is configured to coaxially receive core member (312) of tubular casing (310). An annular array of studs (356) project distally from a distally presented surface surrounding bore (354).

A cylindraceous knife member (340) is coaxially positioned within staple driver member (350). Knife member (340) includes a distally presented, sharp circular cutting edge (342). Knife member (340) is sized such that knife member (340) defines an outer diameter that is smaller than the diameter defined by the inner annular array of staple drivers (352). Knife member (340) also defines an opening that is configured to coaxially receive core member (312) of tubular casing (310). An annular array of openings (346) formed in knife member (340) is configured to complement the annular array of studs (356) of staple driver member (350), such that knife member (340) is fixedly secured to staple driver member (350) via studs (356) and openings (346). Other suitable structural relationships between knife member (340) and stapler driver member (350) will be apparent to those of ordinary skill in the art in view of the teachings herein.

A deck member (320) is fixedly secured to tubular casing (310). Deck member (320) includes a distally presented deck surface (322) defining two concentric annular arrays of staple openings (324). Staple openings (324) are arranged to correspond with the arrangement of staple drivers (352) and staple forming pockets (414) described above. Thus, each staple opening (324) is configured to provide a path for a corresponding staple driver (352) to drive a corresponding staple through deck member (320) and into a corresponding staple forming pocket (414) when stapling head assembly (300) is actuated. It should be understood that the arrangement of staple openings (322) may be modified just like the arrangement of staple forming pockets (414) as described above. It should also be understood that various structures and techniques may be used to contain staples within stapling head assembly (300) before stapling head assembly (300) is actuated. Such structures and techniques that are used to contain staples within stapling head assembly (300) may prevent the staples from inadvertently falling out through staple openings (324) before stapling head assembly (300) is actuated. Various suitable forms that such structures and techniques may take will be apparent to those of ordinary skill in the art in view of the teachings herein.

As best seen in FIG. 6, deck member (320) defines an inner diameter that is just slightly larger than the outer diameter defined by knife member (340). Deck member (320) is thus configured to allow knife member (340) to translate distally to a point where cutting edge (342) is distal to deck surface (322).

In addition to or in lieu of the foregoing, stapling head assembly (300) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

C. Exemplary Shaft Assembly

Figure 8:
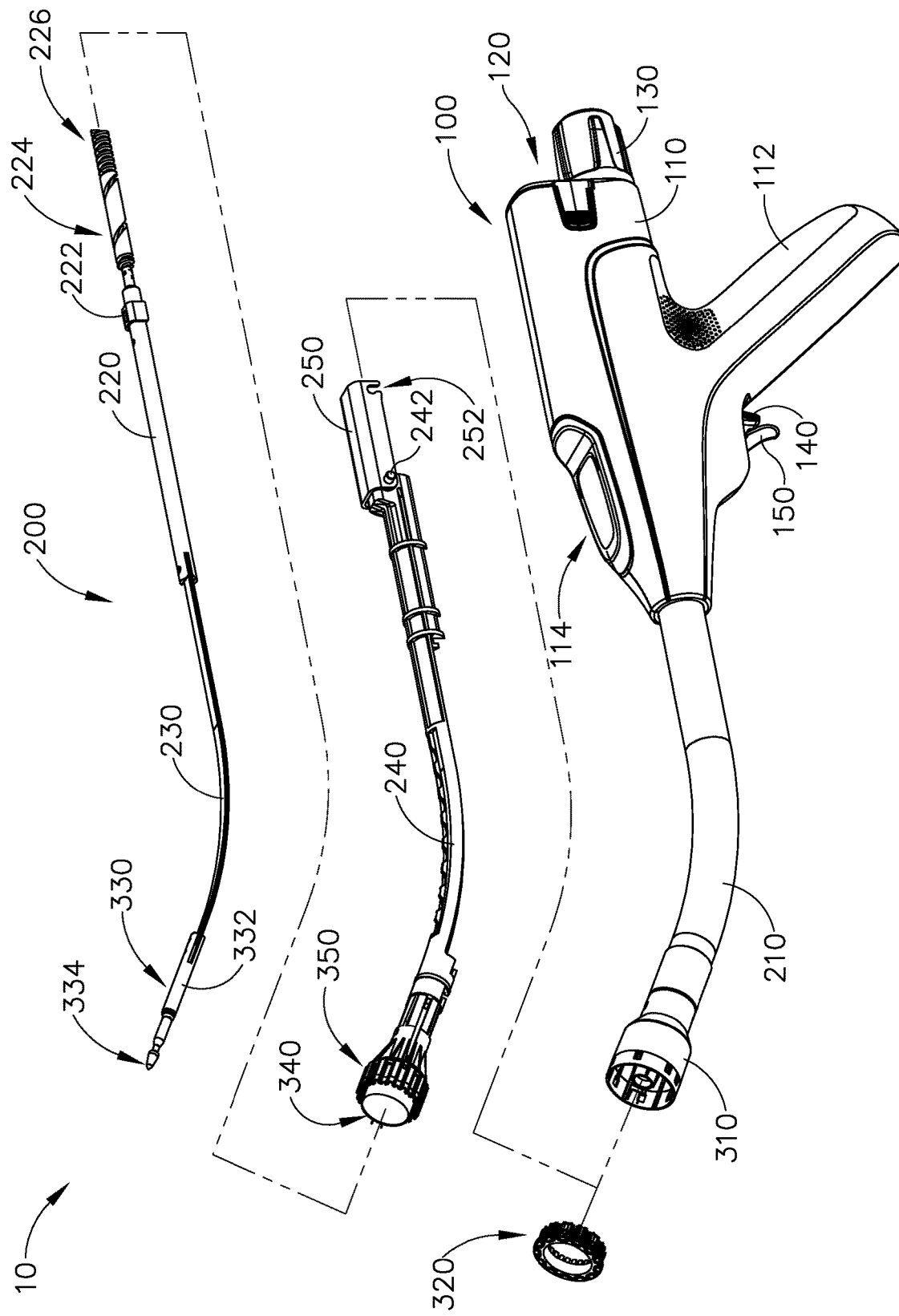
FIG. 8 depicts an exploded perspective view of the circular stapler of FIG. 1, with portions of the shaft assembly shown separately from each other.

FIG. 8 shows various components of shaft assembly (200), which couples components of stapling head assembly (300) with components of handle assembly (100). In particular, and as noted above, shaft assembly (200) includes an outer sheath (210) that extends between handle assembly (100) and tubular casing (310). In the present example, outer sheath (210) is rigid and includes a preformed curved section as noted above.

Shaft assembly (200) further includes a trocar actuation rod (220) and a trocar actuation band assembly (230). The distal end of trocar actuation band assembly (230) is fixedly secured to the proximal end of trocar shaft (332). The proximal end of trocar actuation band assembly (230) is fixedly secured to the distal end of trocar actuation rod (220). It should therefore be understood that trocar (330) will translate longitudinally relative to outer sheath (210) in response to translation of trocar actuation band assembly (230) and trocar actuation rod (220) relative to outer sheath (210). Trocar actuation band assembly (230) is configured to flex such that trocar actuation band assembly (230) may follow along the preformed curve in shaft assembly (200) as trocar actuation band assembly (230) is translated longitudinally relative to outer sheath (210). However, trocar actuation band assembly (230) has sufficient column strength and tensile strength to transfer distal and proximal forces from trocar actuation rod (220) to trocar shaft (332). Trocar actuation rod (220) is rigid. A clip (222) is fixedly secured to trocar actuation rod (220) and is configured to cooperate with complementary features within handle assembly (100) to prevent trocar actuation rod (220) from rotating within handle assembly (100) while still permitting trocar actuation rod (220) to translate longitudinally within handle assembly (100). Trocar actuation rod (220) further includes a coarse helical threading (224) and a fine helical threading (226). Details regarding the movement of trocar actuation rod (220) will be described in greater detail below.

Shaft assembly (200) further includes a stapling head assembly driver (240) that is slidably received within outer sheath (210). The distal end of stapling head assembly driver (240) is fixedly secured to the proximal end of staple driver member (350). The proximal end of stapling head assembly driver (240) is secured to a drive bracket (250) via a pin (242). It should therefore be understood that staple driver member (350) will translate longitudinally relative to outer sheath (210) in response to translation of stapling head assembly driver (240) and drive bracket (250) relative to outer sheath (210). Stapling head assembly driver (240) is configured to flex such that stapling head assembly driver (240) may follow along the preformed curve in shaft assembly (200) as stapling head assembly driver (240) is translated longitudinally relative to outer sheath (210). However, stapling head assembly driver (240) has sufficient column strength to transfer distal forces from drive bracket (250) to staple driver member (350). Details regarding the movement of drive bracket (250) will be described in greater detail below.

While not shown in FIG. 8, it should be understood that shaft assembly (200) may further include one or more spacer elements within outer sheath (210). Such spacer elements may be configured to support trocar actuation band assembly (230) and/or stapling head assembly driver (240) as trocar actuation band assembly (230) and/or stapling head assembly driver (240) translate through outer sheath (210). For instance, such spacer elements may prevent trocar actuation band assembly (230) and/or stapling head assembly driver (240) from buckling as trocar actuation band assembly (230) and/or stapling head assembly driver (240) translate through outer sheath (210). Various suitable forms that such spacer elements may take will be apparent to those of ordinary skill in the art in view of the teachings herein.

In addition to or in lieu of the foregoing, shaft assembly (200) may be further constructed and operable in accordance with at least some of the teachings of U.S. Pat. Nos. 5,205,459; 5,271,544; 5,275,322; 5,285,945; 5,292,053; 5,333,773; 5,350,104; 5,533,661; and/or U.S. Pat. No. 8,910,847, the disclosures of which are incorporated by reference herein. Still other suitable configurations will be apparent to one of ordinary skill in the art in view of the teachings herein.

D. Exemplary Actuator Handle Assembly

Figure 9:
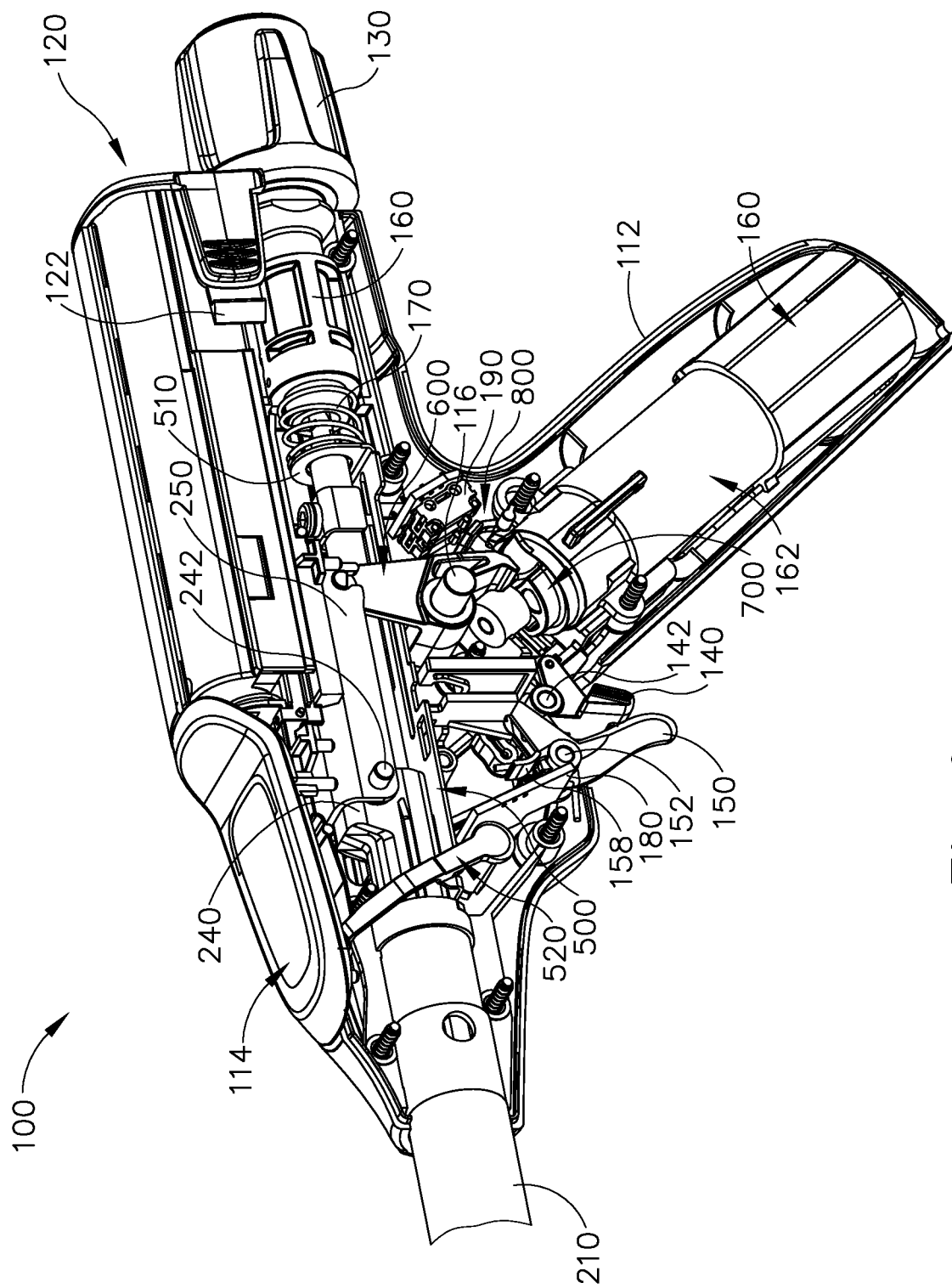
FIG. 9 depicts a perspective view of the handle assembly of the circular stapler of FIG. 1, with a housing half omitted to reveal internal components of the handle assembly.

As shown in FIG. 9, handle assembly (100) includes several components that are operable to actuate anvil (400) and stapling head assembly (300). Handle assembly (100) also includes components that are operable to selectively lock out triggers (140, 150) based on the position of anvil (400) relative to stapling head assembly (300). When triggers (140, 150) are locked out, firing trigger (150) is prevented from initiating actuation of stapling head assembly (300). Thus, trigger (150) is only operable to initiate actuation of stapling head assembly (300) when the position of anvil (400) relative to stapling head assembly (300) is within a predefined range. The components of handle assembly (100) that provide the foregoing operability will be described in greater detail below.

1. Exemplary Anvil Actuation Assembly

Knob (130) protrudes proximally from casing (110) of handle assembly and is rotatable relative to casing (110). As shown in FIG. 9, a nut (160) is secured to the distal end of knob (130). In the present example, nut (160) is fixedly secured to the distal end of knob (130) such that nut (160) will rotate unitarily with knob (130). Nut (160) and knob (130) are configured to cooperate with trocar actuation rod (220) to thereby translate trocar actuation rod (220) longitudinally relative to casing (110) in response to rotation of nut (160) and knob (130) relative to casing (110). As noted above, trocar (330) will translate longitudinally relative to outer sheath (210) in response to translation of trocar actuation rod (220) relative to outer sheath (210) and casing (110).

The proximal portion of trocar actuation rod (220) is positioned within handle assembly (100) to engage nut (160) and knob (130). In particular, trocar actuation rod (220) is positioned within handle assembly (100) such that coarse helical threading (224) will selectively engage a thread engagement feature (not shown) within the interior of nut (160); and such that fine helical threading (226) will selectively engage a thread engagement feature (not shown) within the interior of knob (130). In some versions, the thread engagement feature of nut (160) comprises an inwardly directed tab; while the thread engagement feature of knob (130) comprises a helical threading. Other suitable forms that such thread engagement features may take will be apparent to those of ordinary skill in the art in view of the teachings herein.

In the present example, when nut (160) and knob (130) are rotated relative to casing (110), trocar actuation rod (220) travels proximally through a first range of longitudinal motion where coarse helical threading (224) is engaged with nut (160) to provide a relatively rapid rate of translation. Fine helical threading (226) is not engaged with knob (130) during this range of motion. When nut (160) and knob (130) are further rotated relative to casing (110) after trocar actuation rod (220) completes the first range of motion, trocar actuation rod (220) will continue to travel proximally through a second range of longitudinal motion where fine helical threading (226) is engaged with knob (130) to provide a relatively slow rate of translation. Thus, trocar actuation rod (220) will translate proximally through a sequence of rapid translation followed by slow translation, based on engagement between coarse helical threading (224) and nut (160) followed by engagement between fine helical threading (226) and knob (130).

It should be understood that when anvil (400) is coupled with trocar (330), rotation of knob (130) will provide corresponding translation of anvil relative to stapling head assembly (300). It should also be understood that knob (130) may be rotated in a first angular direction (e.g., clockwise) to retract anvil (400) toward stapling head assembly (300); and in a second angular direction (e.g., counterclockwise) to advance anvil (400) away from stapling head assembly (300). Knob (130) may thus be used to adjust the gap distance (d) between opposing surfaces (412, 322) of anvil (400) and stapling head assembly (300) until a suitable gap distance (d) has been achieved as shown in FIG. 21C and as described in greater detail below.

2. Exemplary Trigger Lockout Assembly

As noted above, knob may be used to adjust the gap distance (d) between opposing surfaces (412, 322) of anvil (400) and stapling head assembly (300). Setting an appropriate gap distance (d) before actuating stapling head assembly (300) may be critical to the success of an anastomosis. For instance, if the gap distance (d) is too great, the staples that are deployed at the anastomosis site may not be sufficiently formed by staple forming pockets (414). This may result in leakage at the anastomosis site, and in some cases may ultimately lead to the separation of the anatomical lumen sections that are joined at the anastomosis site. If the gap distance (d) is too small, the internal structure of the tissue compressed between surfaces (412, 322) may be damaged to the point where the structural integrity of the tissue is compromised. This may prevent the tissue from adequately holding the formed staples, which again may result in leakage or other failure of the anastomosis. It may therefore be desirable to provide the operator with some form of feedback indicating whether the gap distance (d) is within an appropriate range. It may also be desirable to prevent the operator from actuating stapling head assembly (300) unless the gap distance (d) is within an appropriate range.

Figure 10:
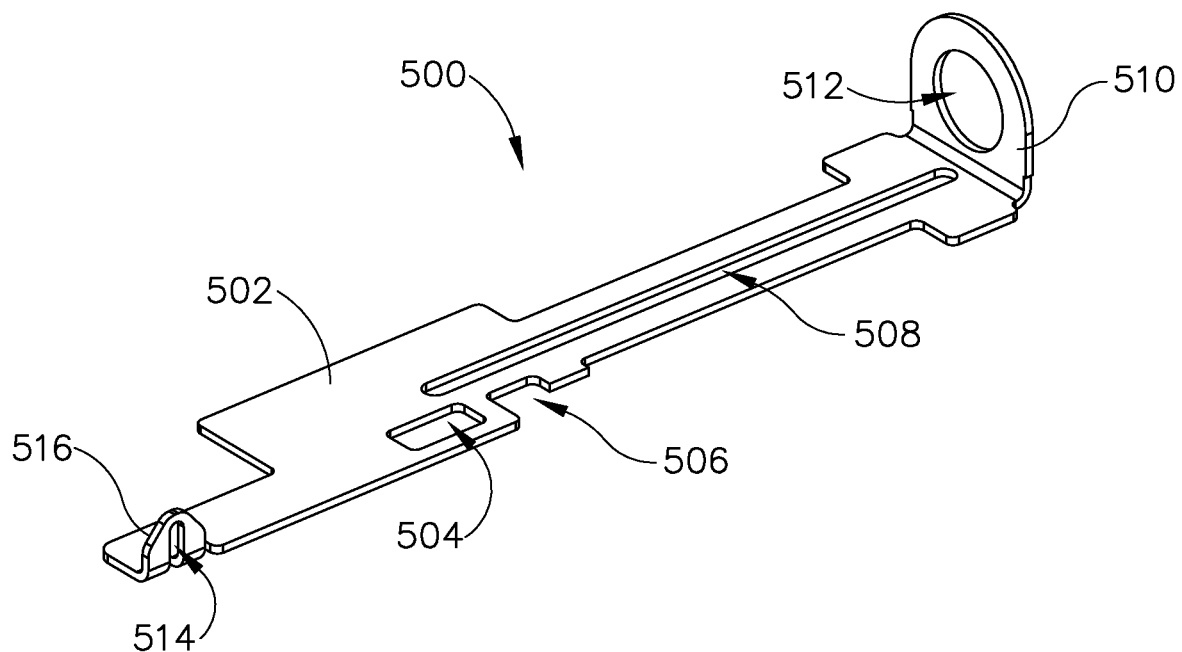
FIG. 10 depicts a perspective view of a bracket of the handle assembly of FIG. 9.

FIGS. 9-12E show components that provide feedback to the operator to indicate whether the gap distance (d) is within an appropriate range; and prevent the operator from actuating stapling head assembly (300) unless the gap distance (d) is within an appropriate range. As best seen in FIGS. 12B-12C, a bracket (500) is configured and positioned to move in response to movement of trocar actuation rod (220). As best seen in FIG. 10, bracket (500) includes a rigid body (502) that defines a first slot (504), a second slot (506), and a third slot (508). An upright feature (510) is positioned at the proximal end of body (502) and defines an opening (512). Trocar actuation rod (220) extends coaxially through opening (512). As shown in FIG. 9, a coil spring (170) is interposed between the proximal end of upright feature (510) and a rigid bulkhead feature that is defined by casing (110) and that forms a support journal for nut (160). The bulkhead is fixed within casing (110) and thereby provides a ground for the proximal end of coil spring (170), such that coil spring (170) resiliently imparts a distal bias to bracket (500) via upright feature (510). Bracket (500) further includes a laterally presented flange (516) at the distal end of body (502). Flange (516) defines a slot (514).

Figure 11:
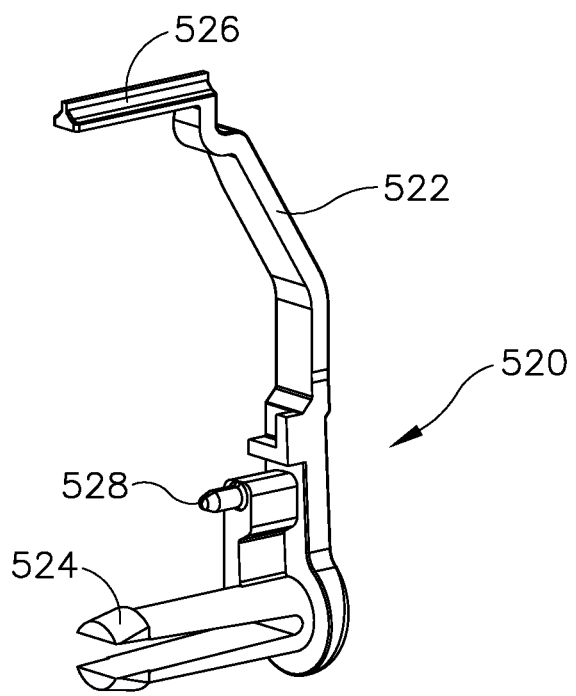
FIG. 11 depicts a perspective view of an indicator member of the handle assembly of FIG. 9.
Figure 12A:
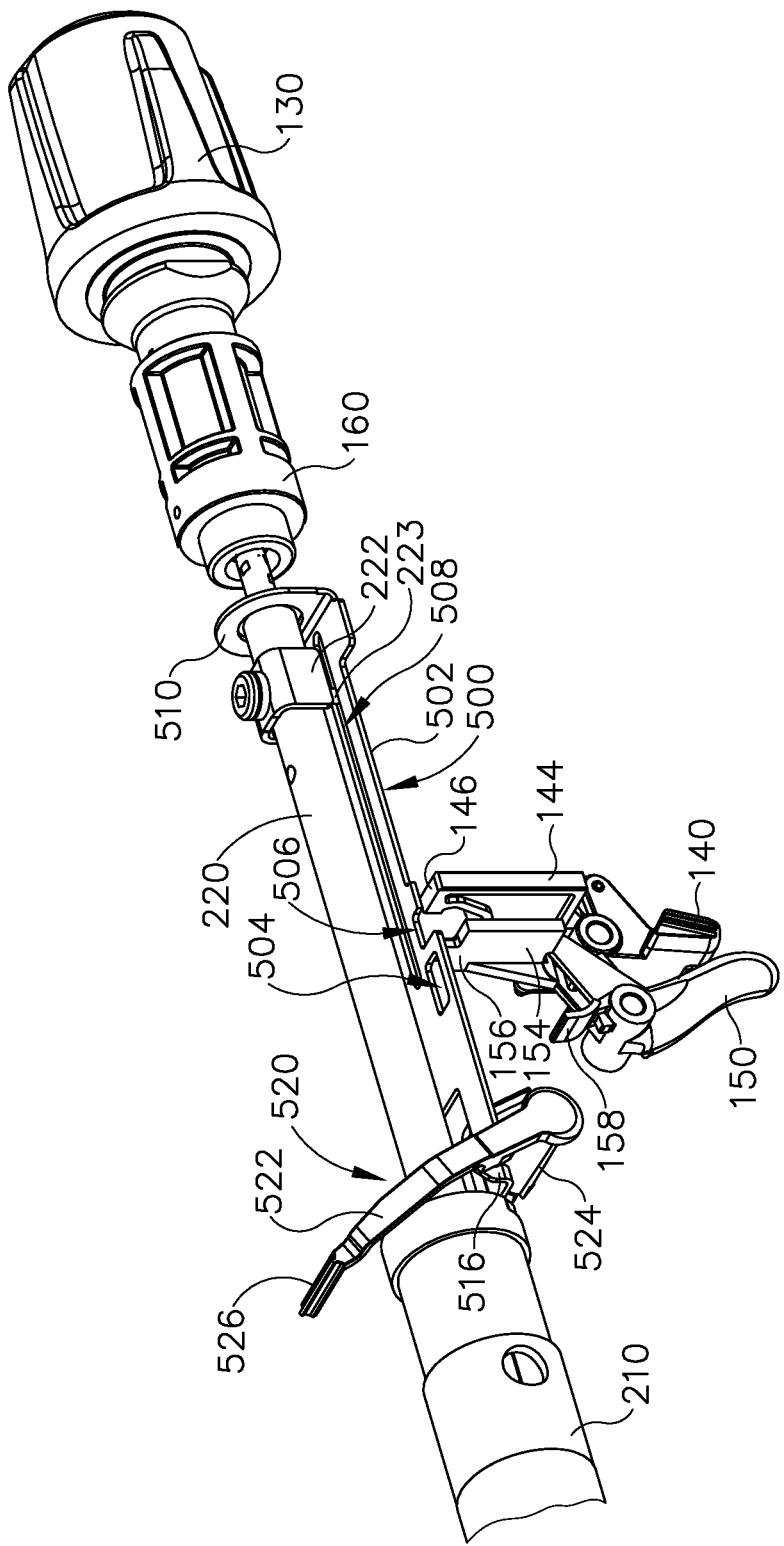
FIG. 12A depicts a perspective view of an anvil actuation assembly of the circular stapler of FIG. 1, an actuation rod in a first position.
Figure 12B:
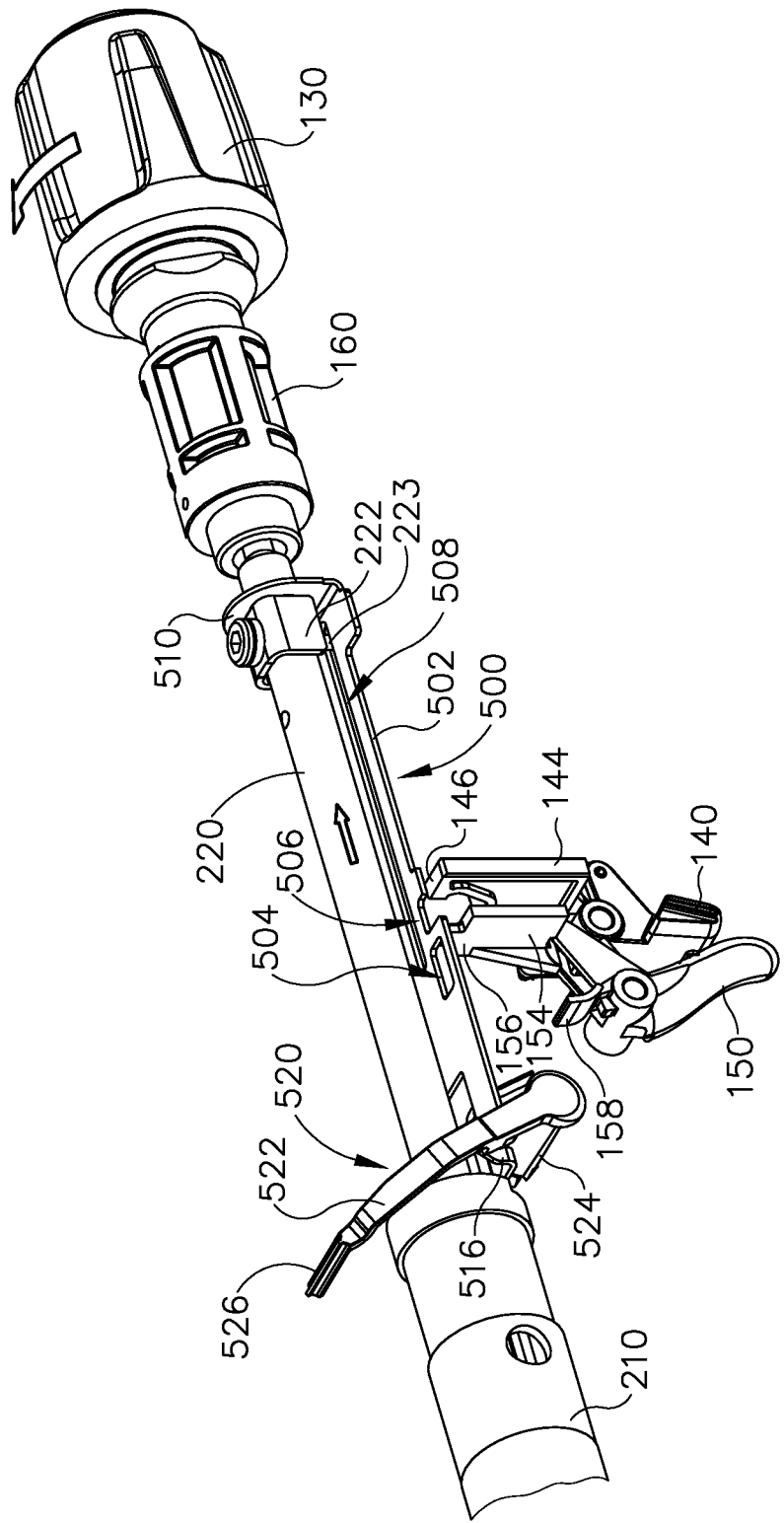
FIG. 12B depicts a perspective view of the anvil actuation assembly of FIG. 12A, with the actuation rod moved to a second position to engage the bracket of FIG. 10.
Figure 12C:
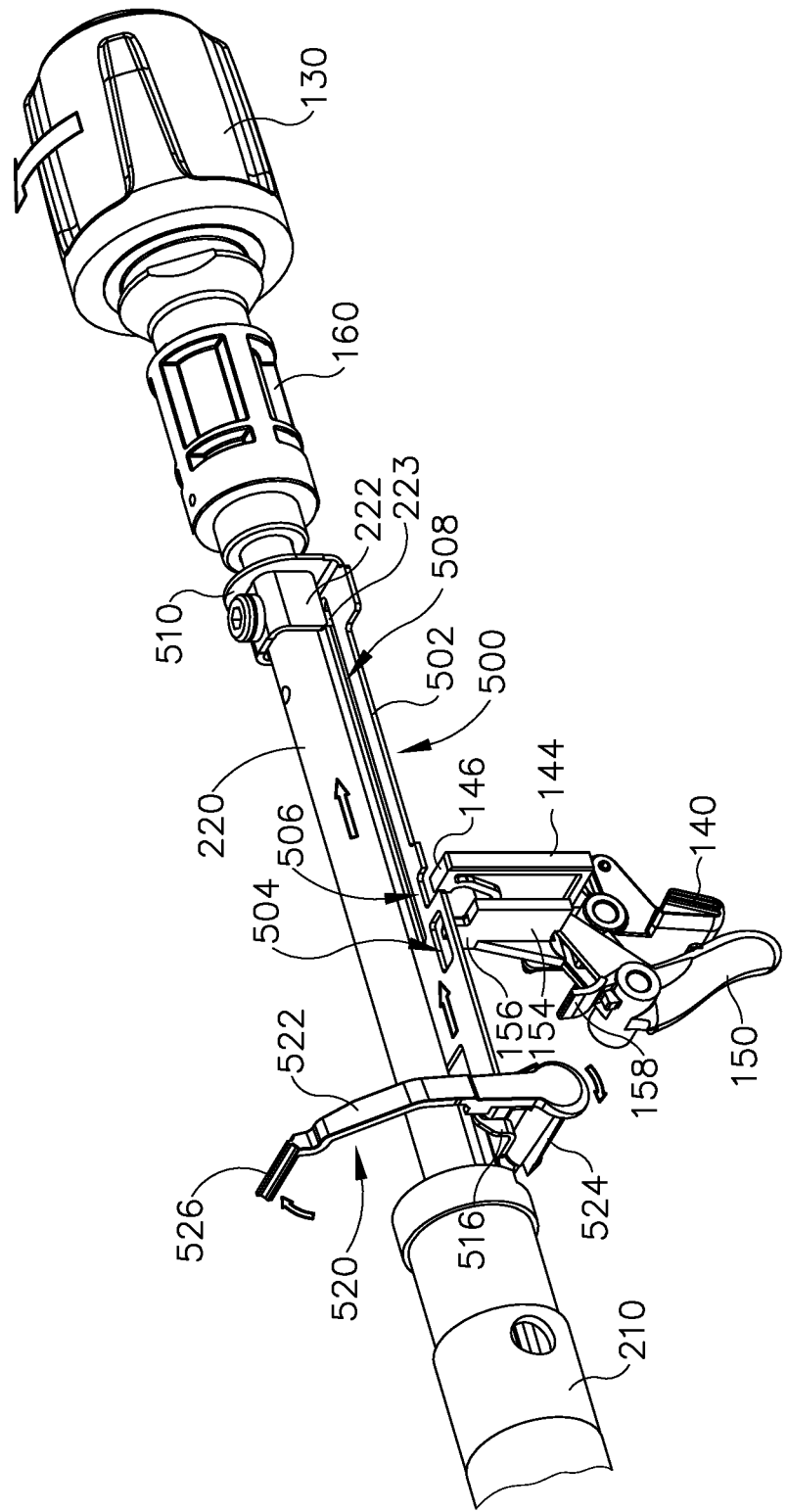
FIG. 12C depicts a perspective view of the anvil actuation assembly of FIG. 12A, with the actuation rod moved to a third position to retract the bracket of FIG. 10 proximally.

As best seen in FIGS. 12B-12C, an indicator member (520) is configured to pivot in response to translation of bracket (500). As best seen in FIG. 11, indicator member (520) comprises an upright arm (522), a snap pin (524) projecting laterally from a lower end of arm (522), an indicator needle (526) projecting laterally from an upper end of arm (522), and a coupling pin (528) projecting laterally from an intermediate region of arm (522). Snap pin (524) is configured to snap into a complementary recess provided by casing (110). Snap pin (524) thereby secures indicator member (520) to casing (110) yet permits indicator member (520) to pivot relative to casing (110) about the longitudinal axis of snap pin (524). Indicator needle (526) is positioned to be visible through window (114) of handle assembly (110) to thereby visually indicate the pivotal position of indicator member (520). Coupling pin (528) is slidably received in slot (514) of flange (516) of bracket (500). This engagement between indicator member (520), casing (110), and bracket (500) provides pivotal movement of indicator member (520) in response to translation of bracket (500).

Bracket (500) is configured to selectively prevent and permit actuation of triggers (140, 150). In particular, slots (504, 506) of bracket (500) are configured to selectively provide clearance for actuation of triggers (140, 150). As shown in FIGS. 12A-12E, safety trigger (140) is pivotably coupled with a first upright member (144). First upright member (144) is coupled with casing (110) such that first upright member (144) is configured to translate upwardly in response to pivoting of safety trigger (140) toward pistol grip (112). However, body (502) of bracket (500) is configured to prevent this movement of first upright member (144) and safety trigger (140) by engaging the upper end (146) of first upright member (144). Body (502) thus blocks movement of first upright member (144) and safety trigger (140) until bracket (500) is moved to a position where slot (506) is aligned with upper end (146) to thereby provide clearance for upward movement of first upright member (144). It should therefore be understood that safety trigger (140) cannot be pivoted toward pistol grip (112) until slot (506) is positioned over upper end (146).

Similarly, firing trigger (150) is pivotally coupled with a second upright member (154). Second upright member (154) is coupled with casing (110) such that second upright member (154) is configured to translate upwardly in response to pivoting of safety trigger (150) toward pistol grip (112). However, body (502) of bracket (500) is configured to prevent this movement of second upright member (154) and firing trigger (150) by engaging the upper end (156) of second upright member (154). Even if safety trigger (140) is pivoted out of the way to otherwise permit movement of firing trigger (150), body (502) blocks movement of second upright member (154) and firing trigger (150) until bracket (500) is moved to a position where slot (504) is aligned with upper end (156) to thereby provide clearance for upward movement of second upright member (154). It should therefore be understood that, even if safety trigger (140) is pivoted out of the way to otherwise permit movement of firing trigger (150), firing trigger (150) cannot be pivoted toward pistol grip (112) until slot (504) is positioned over upper end (156).

Third slot (508) is configured to receive a downwardly projecting boss (223) of clip (222), which is rigidly secured to trocar actuation rod (220). While casing (110) is configured to allow bracket (500) to translate longitudinally within casing (110), casing (110) includes rails, channels, and/or other features that prevent bracket (500) from rotating within casing (110). Thus, the positioning of boss (223) in slot (508) prevents clip (222) and trocar actuation rod (220) from rotating within casing (110). Boss (223) and slot (508) nevertheless allow bracket (500) to translate longitudinally within casing (110) as will be described in greater detail below.

FIGS. 12A-12E depict the above-described components at various stages of operation. In particular, in FIG. 12A, trocar actuation rod (220) is in a distal-most position, such that trocar (330) is in a distal-most position. At this stage, the operator may couple anvil (400) with trocar (330) by inserting trocar (330) into bore (422) until latch members (430) are secured to head (334) of trocar (330). The operator then rotates knob (130), which rotates nut (160). As knob (130) and nut (160) rotate, engagement between coarse helical threading (224) of trocar actuation rod (220) and the complementary feature of nut (160) causes trocar actuation rod (220) to retract proximally at a relatively rapid rate, such that trocar actuation rod (220) reaches the position shown in FIG. 12B. This provides proximal retraction of trocar actuation rod (220) provides retraction of trocar (330) and anvil (400). As trocar actuation rod (220) moves from the position shown in FIG. 12A to the position shown in FIG. 12B, bracket (500) remains stationary. This is due to the fact that clip (222) is spaced apart from upright feature (510) at the stage shown in FIG. 12A and does not engage upright feature (510) until trocar actuation rod (220) reaches the position shown in FIG. 12B.

After reaching the stage shown in FIG. 12B, the operator may continue rotating knob (130) and nut (160), which causes further proximal retraction of trocar actuation rod (220) as shown in FIG. 12C. This of course causes further proximal retraction of trocar (330) and anvil (400). As trocar actuation rod (220) moves from the position shown in FIG. 12B to the position shown in FIG. 12C, clip (222) bears against bracket (500), driving bracket (500) proximally. This proximal movement of bracket (500) causes indicator member (520) to pivot from the position shown in FIG. 12B to the position shown in FIG. 12C due to the positioning of pin (528) in slot (514) of flange (516).

As indicator member (520) pivots from the position shown in FIG. 12B to the position shown in FIG. 12C, the operator may observe the position of indicator needle (526) through window (114) of handle assembly (110). As noted above, a series of hash marks, colored regions, and/or other fixed indicators may be positioned adjacent to window (114) in order to provide a visual context for indicator needle (526), thereby facilitating operator evaluation of the position of needle (526) within window (114). It should be understood that the position of needle (526) within window (114) will be indicative of the longitudinal position of trocar (330) and anvil (400). The position of needle (526) within window (114) will thus indicate the gap distance (d) between opposing surfaces (412, 322) of anvil (400) and stapling head assembly (300). While observing the position of needle (526) within window (114), the operator may rotate knob (130) clockwise or counterclockwise to further retract or advance trocar (330) and anvil (400), thereby providing fine adjustment of the gap distance (d) until a desired gap distance (d) is reached within an appropriate range.

In order to provide fine control of the gap distance (d) adjustment at the stage shown in FIG. 12C, trocar actuation rod (220) will be at a longitudinal position where fine helical threading (226) is engaged with a complementary feature of knob (130) and coarse helical threading (224) is disengaged from the complementary feature of nut (160). In some versions, coarse helical threading (224) disengages nut (160) and fine helical threading (226) begins to engage knob (130) once trocar actuation rod (220) reaches the longitudinal position shown in FIG. 12B (i.e., when clip (222) first engages upright member (510)). In some other versions, the transition from engagement by coarse helical threading (224) to fine helical threading (226) occurs sometime between the stage shown in FIG. 12B and the stage shown in FIG. 12C. Other suitable stages at which the coarse-to-fine transition may occur will be apparent to those of ordinary skill in the art in view of the teachings herein. It should also be understood that some alternative versions of trocar actuation rod (220) may have just a single threading section, with the pitch of the threading being consistent along the length of the threading. In other words, trocar actuation rod (220) does not necessarily need to have two different sections of threading (224, 226) with different pitches.

At the stage shown in FIG. 12C, slot (506) is aligned with upper end (146) to thereby provide clearance for upward movement of first upright member (144). Similarly, slot (504) is aligned with upper end (156) to thereby provide clearance for upward movement of second upright member (154). In the present example, slots (504, 506) are sized and positioned such that slots (504, 506) only provide clearance for upward movement of upright members (144, 154) when the gap distance (d) is within a clinically acceptable range. By way of example only, a "clinically acceptable range" for the gap distance (d) may be between approximately 0.110 inches and approximately 0.040 inches. As another merely illustrative example, a "clinically acceptable range" for the gap distance (d) may be between approximately 0.110 inches and approximately 0.020 inches. Even when slots (504, 506) are positioned to provide clearance for upward movement of upright members (144, 154) as shown in FIG. 12C, safety trigger (140) will still block pivotal movement of firing trigger (150) about a pin (152) (FIG. 9) when safety trigger (140) is in the non-actuated position shown in FIG. 12C. Thus, in order to enable movement of firing trigger (150), the operator will need to first actuate safety trigger (140) about a pin (142) (FIG. 9) from the position shown in FIG. 12C to the position shown in FIG. 12D.

Figure 12D:
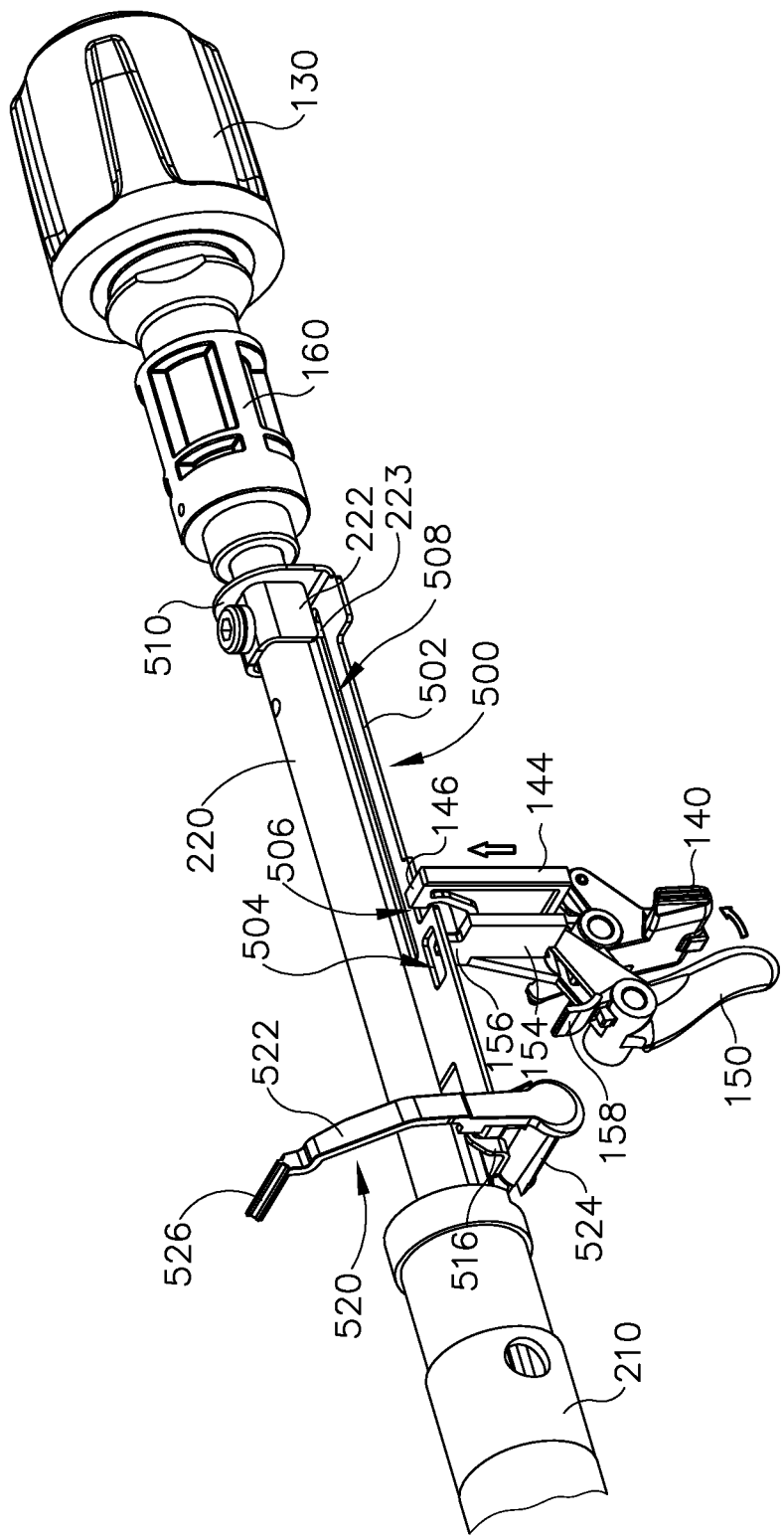
FIG. 12D depicts a perspective view of the anvil actuation assembly of FIG. 12A, with a safety trigger pivoted from a first position to a second position.

As shown in FIG. 12D, upper end (146) passes through slot (506) as safety trigger (140) is pivoted from the position shown in FIG. 12C to the position shown in FIG. 12D. It should be understood that this movement of upper end (146) would not be possible at the stages shown in FIGS. 12A-12B (when the gap distance (d) is too great) because body (502) would physically block upward movement of upright member (144), thereby physically blocking pivotal movement of safety trigger (140). In the present example, a cap (not shown) incorporated into knob (130) prevents knob (130) from rotating to a point where anvil (400) would be retracted too far proximally (such that the gap distance (d) is too small). In some other variations, even if knob (130) were to permit anvil (400) to be retracted too far proximally (such that the gap distance (d) is too small), body (502) would physically block upward movement of upright member (144), thereby physically blocking pivotal movement of safety trigger (140), in the event that the operator retracts trocar (330) and anvil (400) too far proximally (such that the gap distance (d) is too small). Regardless of whether body (502), knob (130), or some other feature prevents actuation when the gap distance (d) would be too small, it should be understood that instrument (10) permits actuation of safety trigger (140) only when the gap distance (d) is within the clinically acceptable range.

Figure 12E:
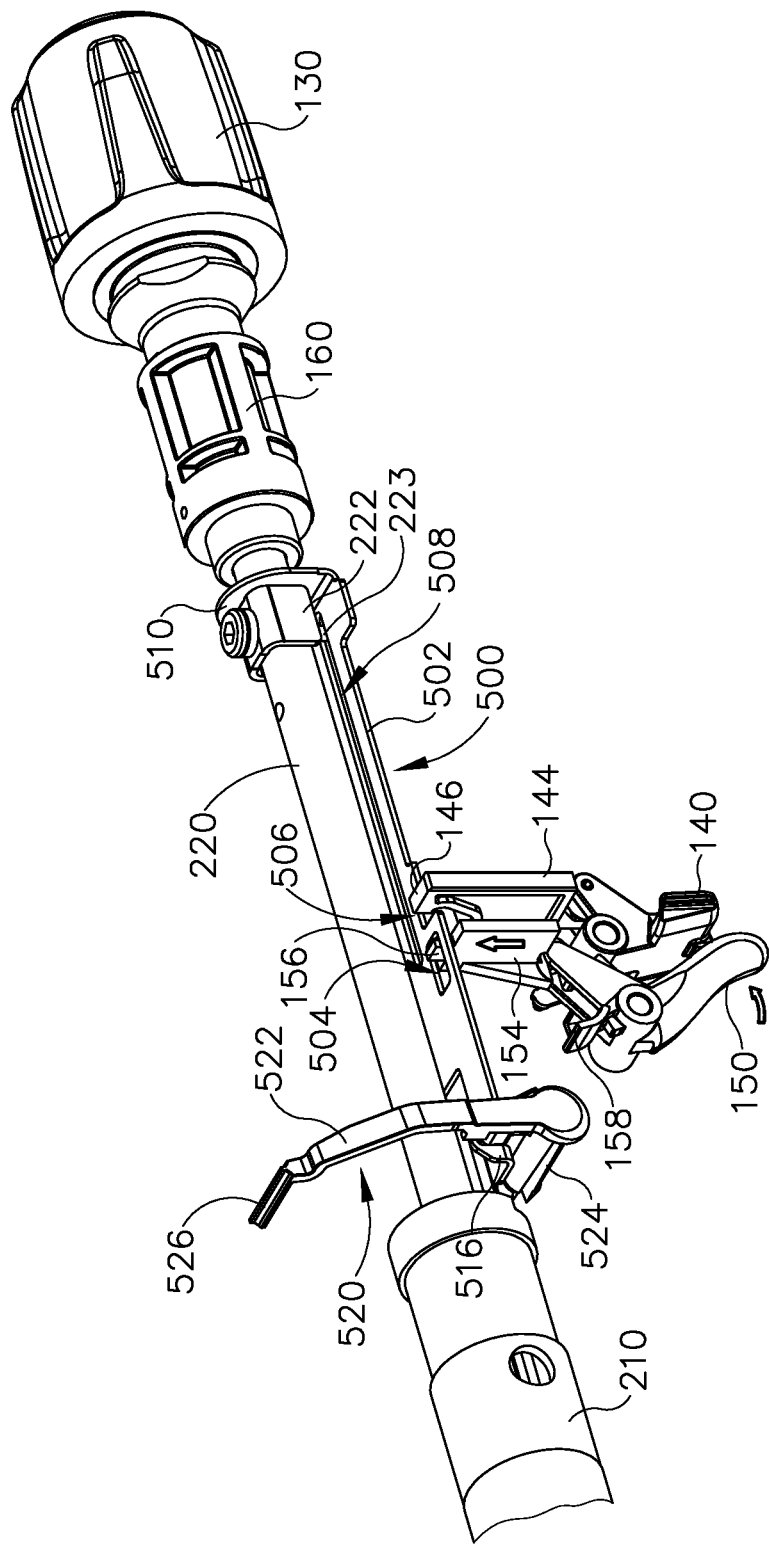
FIG. 12E depicts a perspective view of the anvil actuation assembly of FIG. 12A, with a firing trigger pivoted from a first position to a second position.
Figure 13:
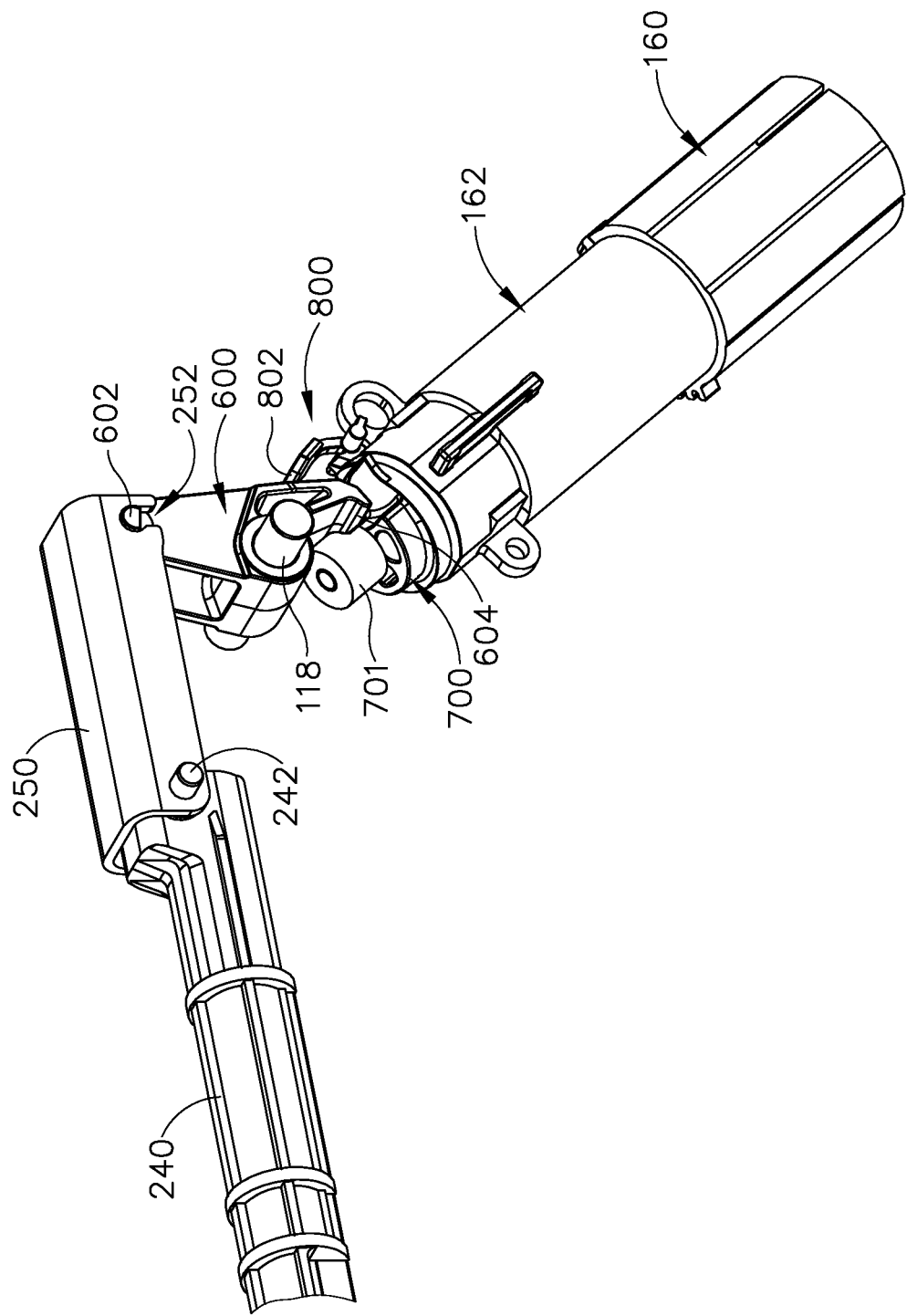
FIG. 13 depicts a perspective view of a stapling head actuation assembly of the circular stapler of FIG. 1.

As noted above, safety trigger (140) is configured to prevent actuation of firing trigger (150) until safety trigger (140) has been actuated. Once safety trigger (140) has been actuated, the operator may actuate firing trigger (150) from the position shown in FIG. 12D to the position shown in FIG. 12E. As shown in FIG. 12E, upper end (156) passes through slot (504) as firing trigger (150) is pivoted from the position shown in FIG. 12D to the position shown in FIG. 12E. It should be understood that, even in the complete absence of safety trigger (140), this movement of upper end (156) would not be possible at the stages shown in FIGS. 12A-12B (when the gap distance (d) is too great) because body (502) would physically block upward movement of upright member (154), thereby physically blocking pivotal movement of firing trigger (150). It should also be understood that body (502) would also physically block upward movement of upright member (154), thereby physically blocking pivotal movement of firing trigger (150), in the event that the operator retracts trocar (330) and anvil (400) too far proximally (such that the gap distance (d) is too small). Thus, even in the complete absence of safety trigger (140), firing trigger (150) may only be actuated when the gap distance (d) is within the clinically acceptable range.

Firing trigger (150) of the present example includes an integral actuation paddle (158). Paddle (158) pivots forwardly as firing trigger (150) pivots from the position shown in FIG. 12D to the position shown in FIG. 12E. Paddle (158) is configured to actuate a switch of a motor activation module (180), which is shown in FIG. 9, when firing trigger (150) pivots from the position shown in FIG. 12D to the position shown in FIG. 12E. Motor activation module (180) is in communication with battery pack (120) and motor (160), such that motor activation module (180) is configured to provide activation of motor (160) with electrical power from battery pack (120) in response to paddle (158) actuating the switch of motor activation module (180). Thus, motor (160) will be activated when firing trigger (150) is pivoted from the position shown in FIG. 12D to the position shown in FIG. 12E. This activation of motor (160) will actuate stapling head assembly (300) as described in greater detail below.

3. Exemplary Stapling Head Actuation Assembly

FIGS. 13-20D show various components that are operable to actuate stapling head assembly (300). These components include motor (160), a gearbox (162), a rotary cam member (700), a cam follower (600), drive bracket (250) and stapling head assembly driver (240). Gearbox (162) is coupled with a drive shaft of motor (160) and is further coupled with cam member (700). Activation of motor (160) thus causes rotation of cam member (700) via gearbox (162). Various suitable configurations that may be used for gearbox (162) will be apparent to those of ordinary skill in the art in view of the teachings herein. Cam member (700) is configured to interact with cam follower (160) to pivot cam follower (160) in two angular directions about a pin (118) as will be described in greater detail below. Pin (118) is coupled with casing (110). A bushing (701) provides rotary support to cam member (700) relative to casing (110).

Figure 14:
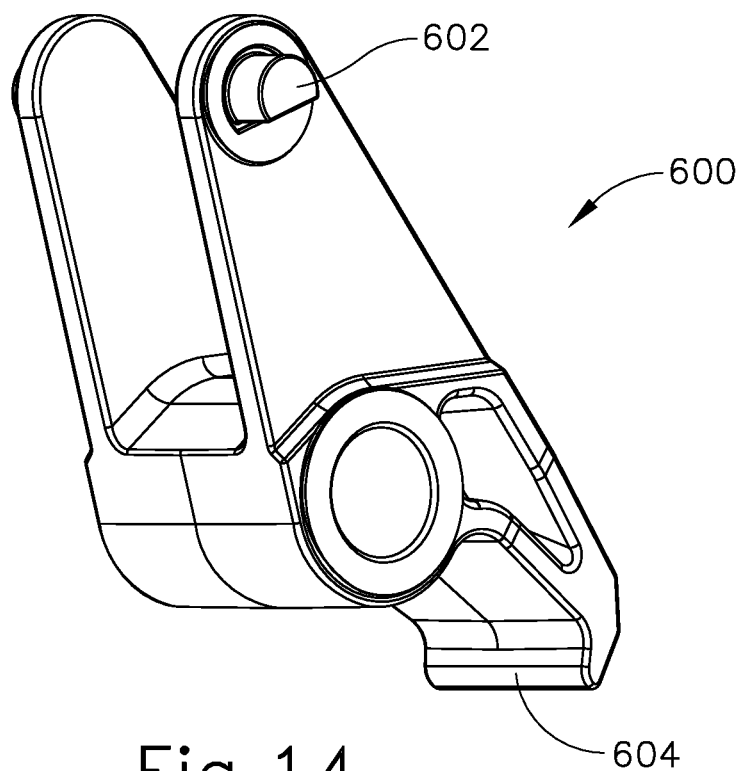
FIG. 14 depicts a perspective view of a cam follower of the stapling head actuation assembly of FIG. 13.
Figure 15:
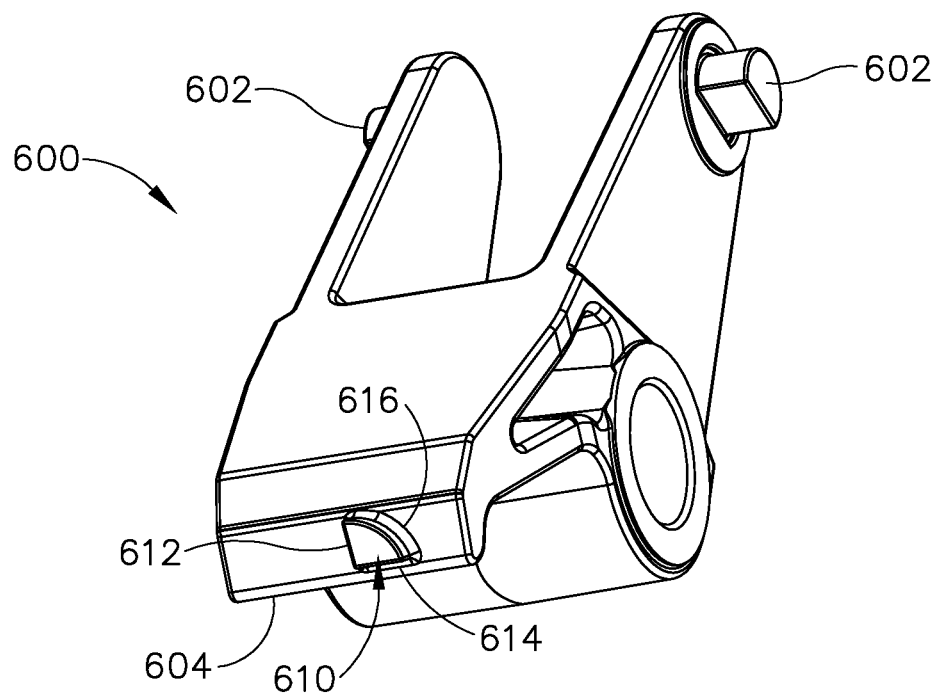
FIG. 15 depicts another perspective view of the cam follower of FIG. 14.

Cam follower (600) is pivotably coupled with drive bracket (250) via a pair of integral pins (602), which are received in complementary notches (252) of drive bracket (250). As shown in FIGS. 14-15, cam follower (600) includes a first bearing feature (604) and a second bearing feature (610). First bearing feature (604) consists of a rounded, horizontally extending surface. Second bearing feature (610) is shaped like a quarter-pie defined by a straight vertical surface (612), a horizontally extending surface (614), and a curved surface (616). Second bearing feature (610) projects proximally relative to first bearing feature (504).

Figure 16:
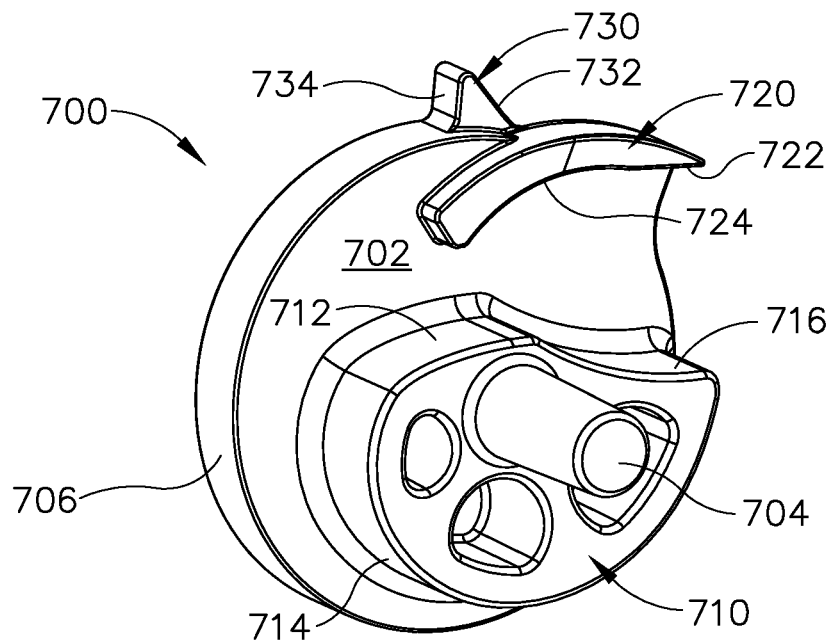
FIG. 16 depicts a perspective view of a rotary cam of the stapling head actuation assembly of FIG. 13.
Figure 17:
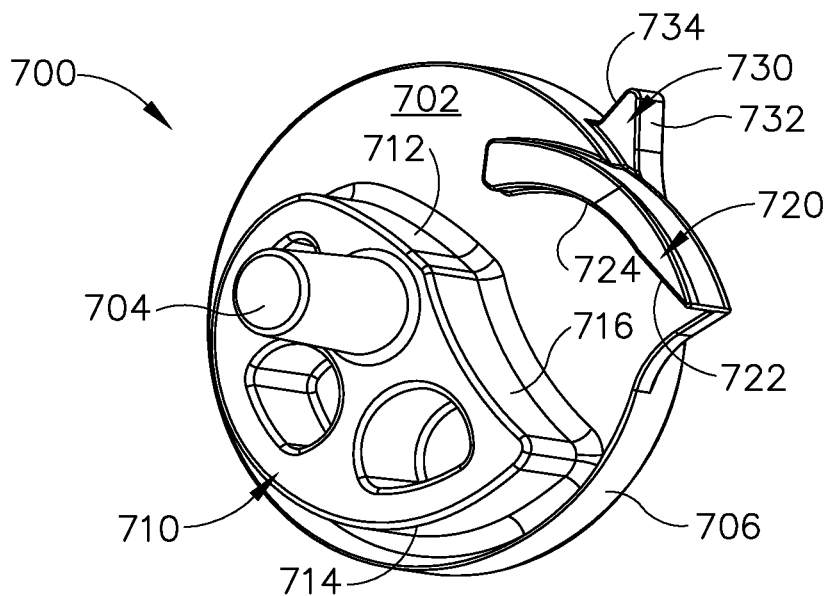
FIG. 17 depicts another perspective view of the rotary cam of FIG. 16.

FIGS. 16-17 show cam member (700) in greater detail. Cam member (700) comprises a distal face (702), a distally projecting post (704), and an outer circumferential surface (706). A first cam feature (710) and a second cam feature (720) project distally from distal face (702). Post (704) engages bushing (701). First cam feature (710) comprises a first surface region (712), a second surface region (714), and a third surface region (716). First surface region (712) is convexly defined by a relatively large radius of curvature, such that first surface region (712) is nearly flat. Second surface region (714) is convexly defined by a progressively increasing radius of curvature. Third surface region (716) is concavely defined by a relatively large radius of curvature. In addition to projecting distally from distal face (702), second cam feature (720) projects outwardly from outer circumferential surface (706). Second cam feature (720) includes a first surface region (722) and a second surface region (724). First surface region (722) is substantially flat while second surface region (724) is concavely curved. The origin of the radius of curvature for each curved surface region (712, 714, 716, 724) is offset from the center of post (704).

Figure 18A:
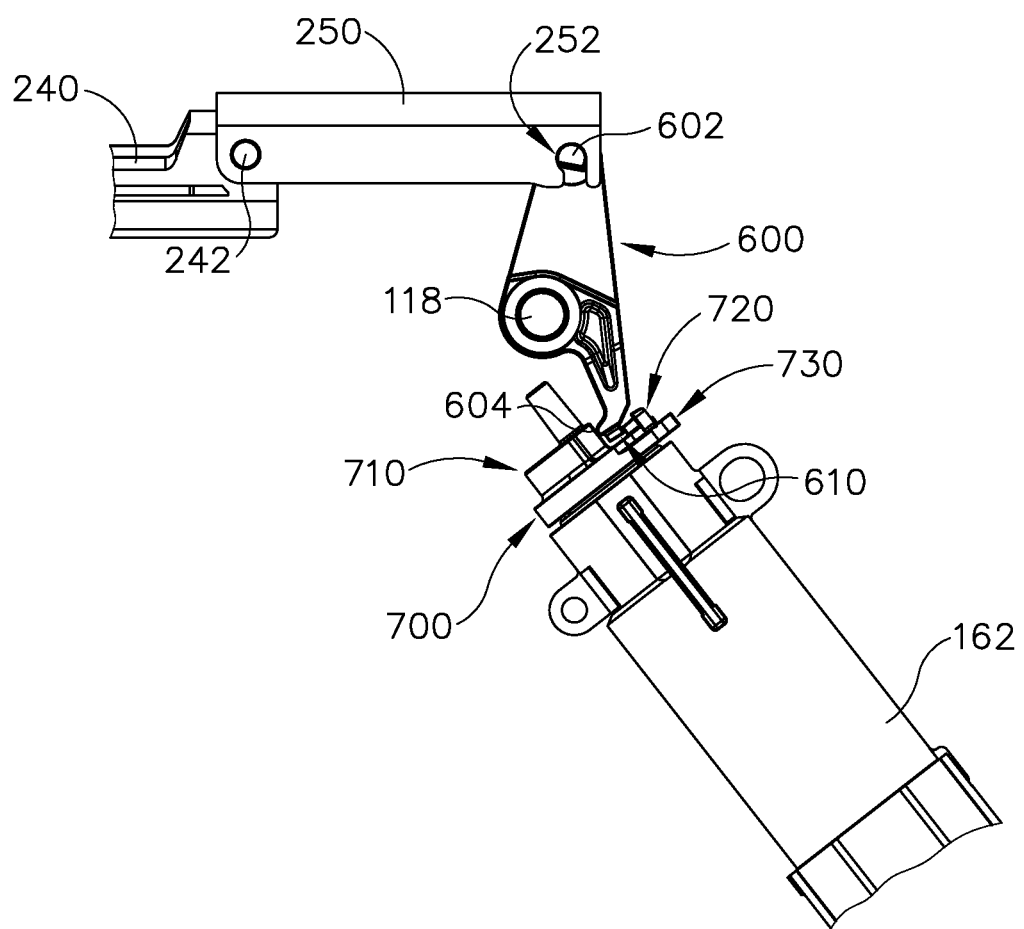
FIG. 18A depicts a side elevational view of the stapling head actuation assembly of FIG. 13, with the rotary cam in a first angular position and the cam follower in a first pivotal position.
Figure 18B:
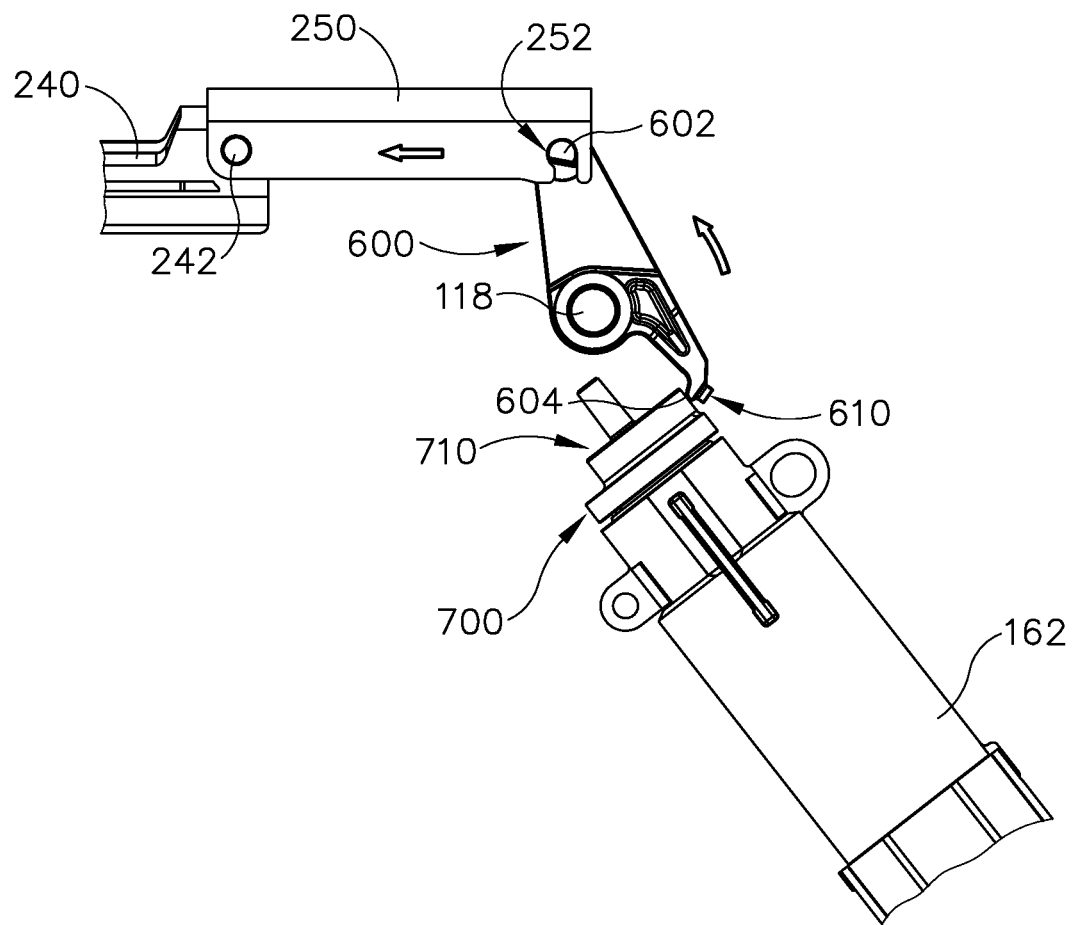
FIG. 18B depicts a side elevational view of the stapling head actuation assembly of FIG. 13, with the rotary cam in a second angular position and the cam follower in a second pivotal position.

FIGS. 18A-18B show the general interaction between cam follower (600) and first and second cam features (710, 720), though this interaction will be described in greater detail below with reference to FIGS. 20A-20D. As cam member (700) is rotated from the position shown in FIG. 18A to the position shown in FIG. 18B, first cam feature (710) bears against first bearing feature (604) of cam follower (600), causing cam follower to pivot about pin (118). In the view shown in FIGS. 18A-18B, cam follower (600) pivots counterclockwise as cam member (700) is rotated from the position shown in FIG. 18A to the position shown in FIG. 18B. As can be seen in the transition from FIG. 18A to FIG. 18B, this counterclockwise pivoting of cam follower (600) drives drive bracket (250) and stapling head assembly driver (240) distally, thereby actuating stapling head assembly (300). As cam member (700) continues to rotate in the same direction back toward the position shown in FIG. 18A, second cam feature (720) engages and bears against second bearing feature (610) of cam follower (600), causing cam follower (600) to pivot clockwise about pin (118). This clockwise pivoting of cam follower (600) about pin (118) retracts drive bracket (250) and stapling head assembly driver (240) proximally back toward the position shown in FIG. 18A.

Figure 19A:
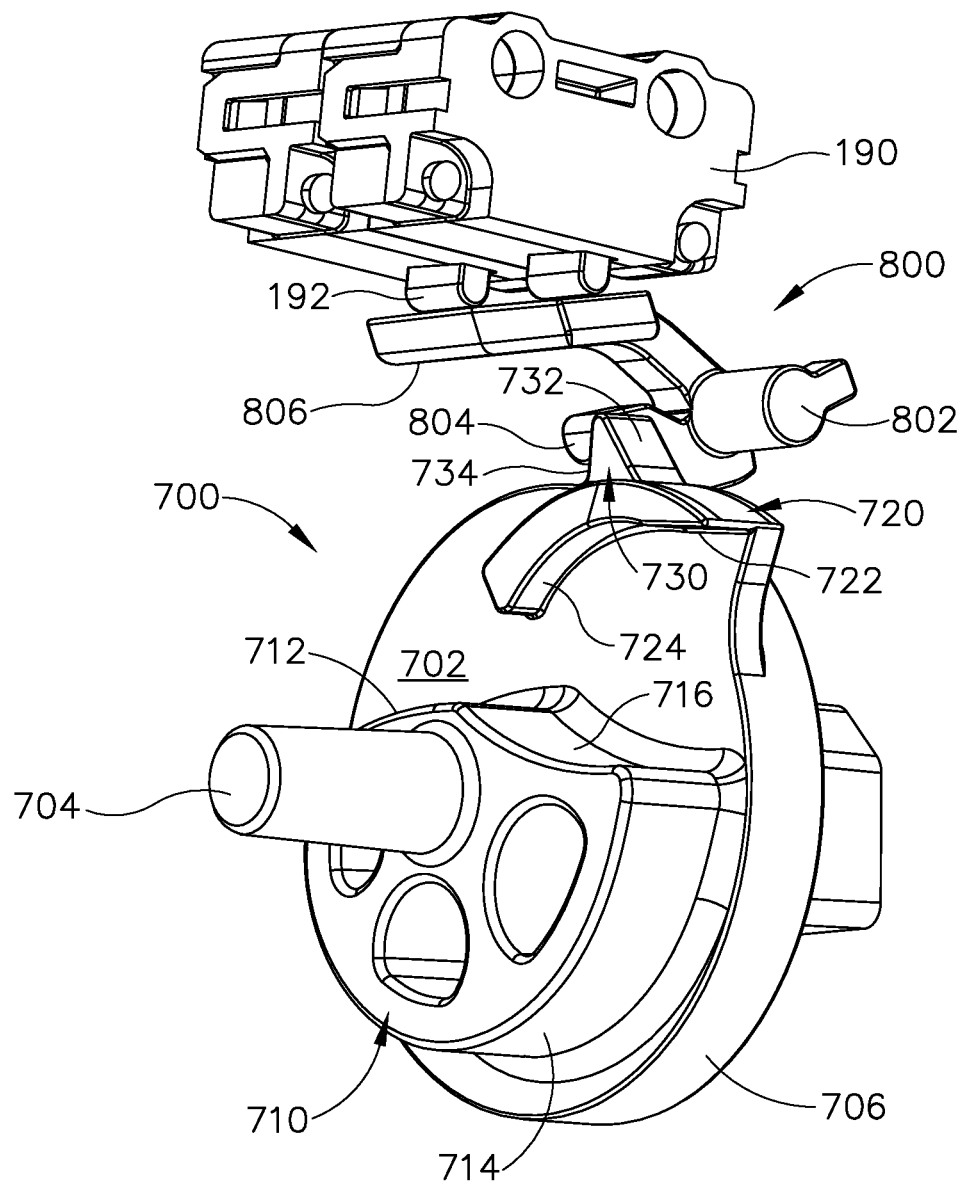
FIG. 19A depicts a perspective view of the rotary cam of FIG. 16, a rocker member, and a stop switch, with the rotary cam in a first angular position and the rocker member in a first pivotal position.
Figure 19B:
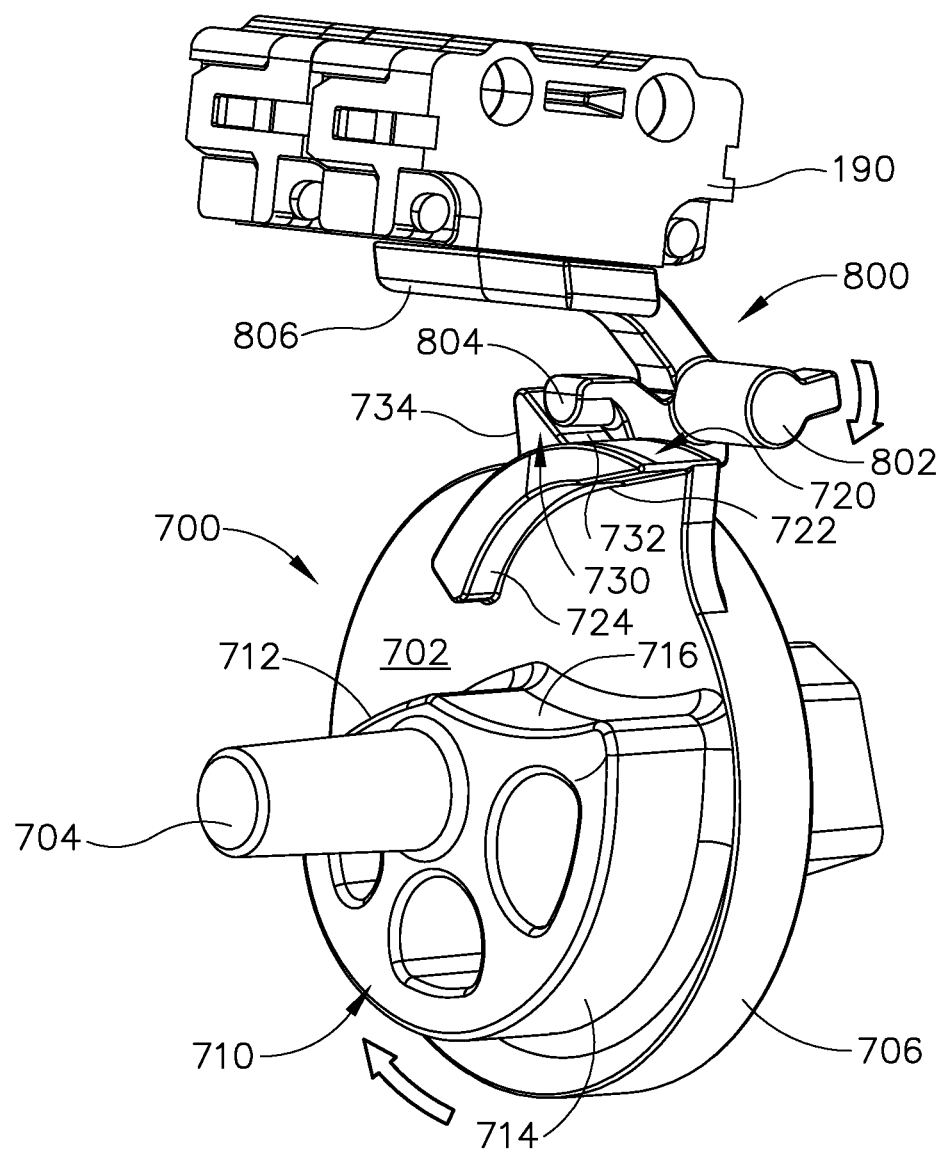
FIG. 19B depicts a perspective view of the rotary cam of FIG. 16, the rocker member of FIG. 19A, and the stop switch of FIG. 19A, with the rotary cam in a fourth angular position and the rocker member in a second pivotal position.

Referring back to FIGS. 16-17, a third cam feature (730) projects outwardly from outer circumferential surface (706). Third cam feature (730) comprises a first surface region (732) and a second surface region (734). First surface region (732) is flat and is oriented generally tangentially relative to outer circumferential surface (706). Second surface region (732) is also flat and is oriented radially outwardly relative to outer circumferential surface (706). Third cam feature (730) is configured to interact with a rocker member (800) as shown in FIGS. 19A-19B. Rocker member (800) comprises an integral pin (802), a bearing member (804), and a paddle (806). Pin (802) is pivotably coupled with casing (110), such that rocker member (800) is pivotable within casing (110) about the longitudinal axis defined by pin (802). Bearing member (804) is configured to interact with third cam feature (730) as will be described in greater detail below. Paddle (806) is configured to actuate a switch button (192) of a short circuit module (190) as will also be described in greater detail below.

FIG. 19A shows cam member (700) in the same position as shown in FIG. 18A. At this stage, second surface region (734) of third cam feature (730) is adjacent to bearing member (804) of rocker member (800). FIG. 19B shows cam member (700) in a position where cam member (700) has been rotated past the position shown in FIG. 18B and back toward the position shown in FIG. 18A. However, cam member (700) has not completed a full revolution. At the stage shown in FIG. 19B, first surface region (732) has engaged and borne against bearing member (804), thereby pivoting rocker member (800) about the longitudinal axis defined by pin (802). This has caused paddle (806) to actuate switch button (192) of short circuit module (190). Short circuit module (190) is configured to prevent motor (160) from further activation when switch button (192) has been actuated. In some versions, short circuit module (190) couples battery pack (120) with a power sink, in addition to short circuiting motor (160), when switch button (192) is actuated. This may result in discharge of battery pack (120) in addition to stopping activation of motor (160) once an actuation stroke of stapling head assembly (300) has been completed. By way of example only, short circuit module (190) may be configured and operable in accordance with at least some of the teachings of U.S. Pub. No. 2015/0083774, issued as U.S. Pat. No. 9,907,552 on Mar. 6, 2018, the disclosure of which is incorporated by reference herein. Other suitable configurations will be apparent to those of ordinary skill in the art in view of the teachings herein.

FIGS. 20A-20D schematically depict the interaction between cam member (700), features of cam follower (600), and features of rocker member (800) as cam member (700) rotates. It should be understood that the rotation of cam member (700) throughout the stages shown in FIGS. 20A-20D is driven by motor (160) and gearbox (162). FIG. 20A shows cam member (700) in the same position as shown in FIGS. 18A and 19A. At this stage, first bearing feature (604) of cam follower (600) is positioned on first surface region (712) and bearing member (804) or rocker member (800) is adjacent to second surface region (734) of third cam feature (730). Also at this stage, knife member (340) and staple driver member (350) are in proximal positions, such that stapling head assembly (300) is in a non-actuated state. As cam member (700) is rotated to the position shown in FIG. 20B, second surface region (714) bears against bearing member (804), thereby driving bearing member (804) upwardly. This causes cam follower (600) to pivot about pin (118) to the position shown in FIG. 18B. Cam follower (600) thus drives knife member (340) and staple driver member (350) distally via drive bracket (250) and stapling head assembly driver (240). Stapling head assembly (300) is thus in an actuated state at the stage shown in FIG. 20B. In some versions, cam member (700) rotates through an angular range of approximately 270° in order to transition stapling head assembly (300) from the non-actuated state to the actuated state.

After stapling head assembly (300) has been actuated, cam member (700) continues to rotate to the position shown in FIG. 20C. At this stage, first surface region (722) of second cam member (720) begins to engage curved surface (616) of second bearing feature (610) of cam follower (600). As cam member (700) continues to rotate to the position shown in FIG. 20D, second surface region (724) engages curved surface (616) of second bearing feature (610), driving second bearing feature (610) downwardly. This causes cam follower (600) to pivot about pin (118) back from the position shown in FIG. 18B toward the position shown in FIG. 18A. Cam follower (600) thus drives knife member (340) and staple driver member (350) proximally via drive bracket (250) and stapling head assembly driver (240). In addition, first surface region (732) has engaged and borne against bearing member (804), thereby pivoting rocker member (800) about the longitudinal axis defined by pin (802) at the stage shown in FIG. 20D. Rocker member (800) is thus in the same state in FIG. 20D as shown in FIG. 19B. Short circuit module (190) has thus been actuated at the stage shown in FIG. 20D.

It should be understood from the foregoing that cam member (700) is operable to drive knife member (340) and staple driver member (350) distally, then drive knife member (340) and staple driver member (350) proximally and actuate short circuit module (190) by rotating in a single angular direction through the range of motion shown in FIGS. 20A-20D. Other suitable ways in which knife member (340), staple driver member (350), and short circuit module (190) may be actuated will be apparent to those of ordinary skill in the art in view of the teachings herein.

E. Exemplary Anastomosis Procedure

Figure 21A:
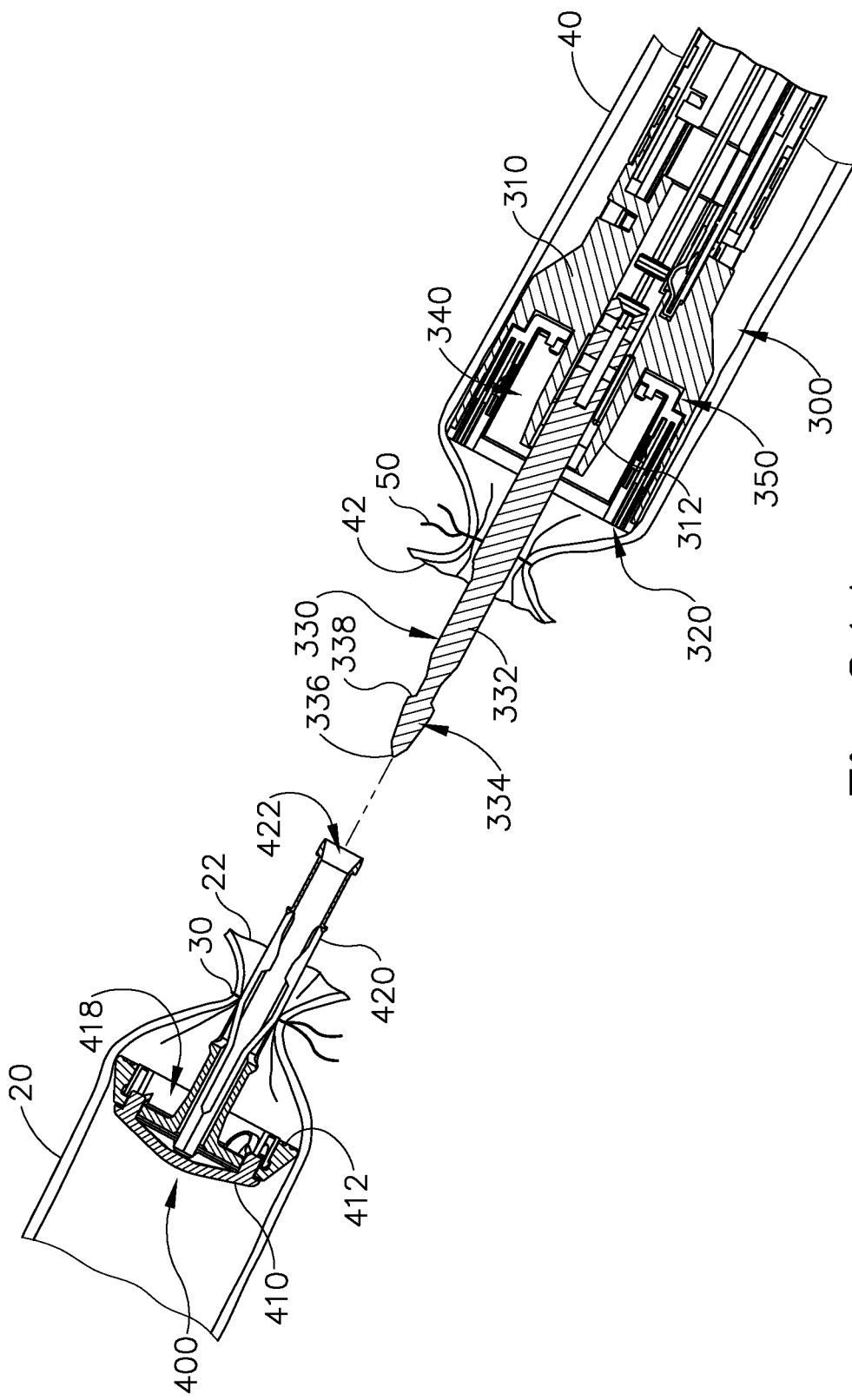
FIG. 21A depicts a cross-sectional side view of the anvil of FIG. 3 positioned within a first section of a digestive tract and the stapling head assembly of FIG. 6 positioned in a second section of the digestive tract, with the anvil separated from the stapling head assembly.
Figure 21B:
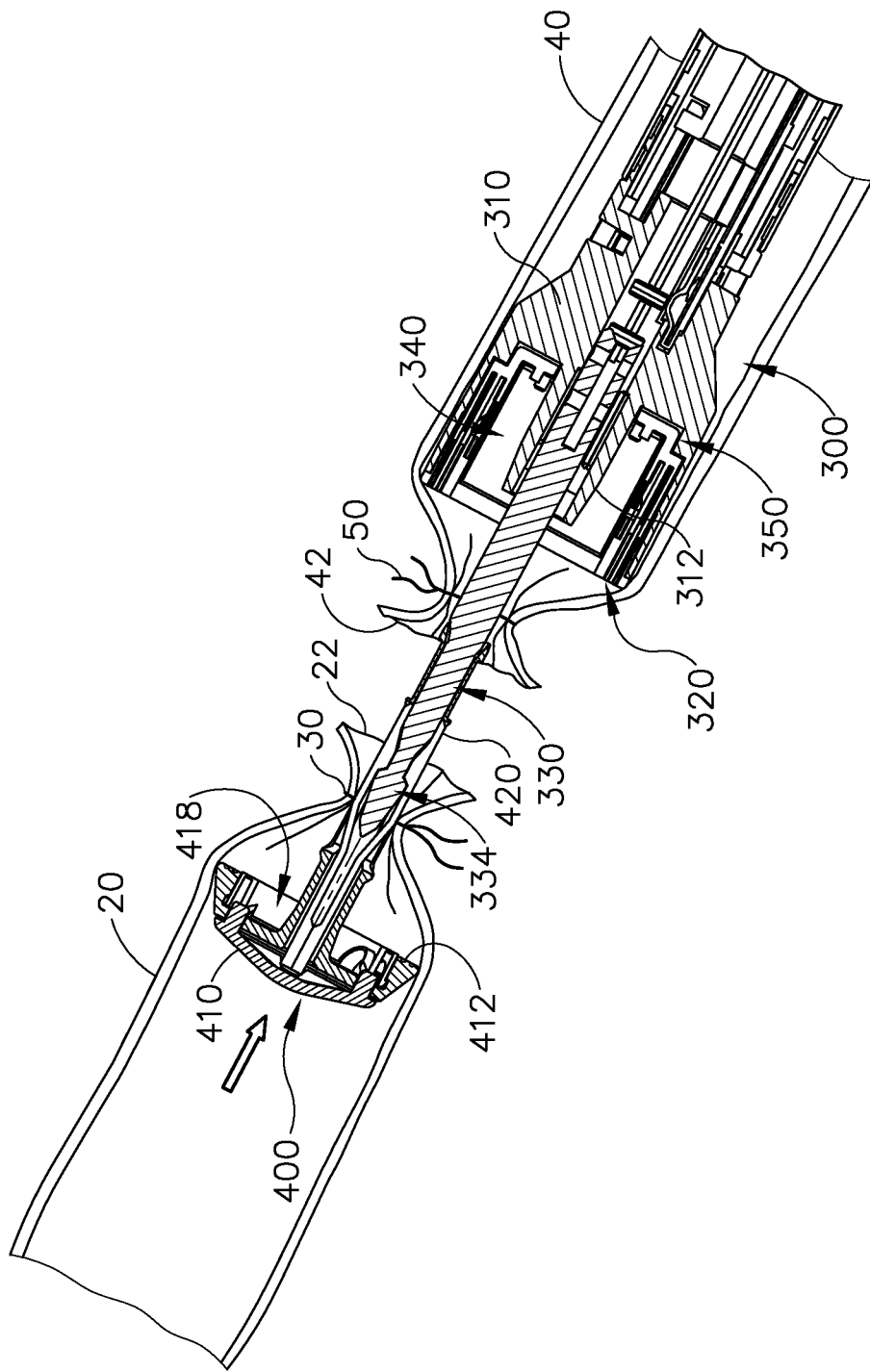
FIG. 21B depicts a cross-sectional side view of the anvil of FIG. 3 positioned within the first section of the digestive tract and the stapling head assembly of FIG. 6 positioned in the second section of the digestive tract, with the anvil secured to the stapling head assembly.
Figure 21C:
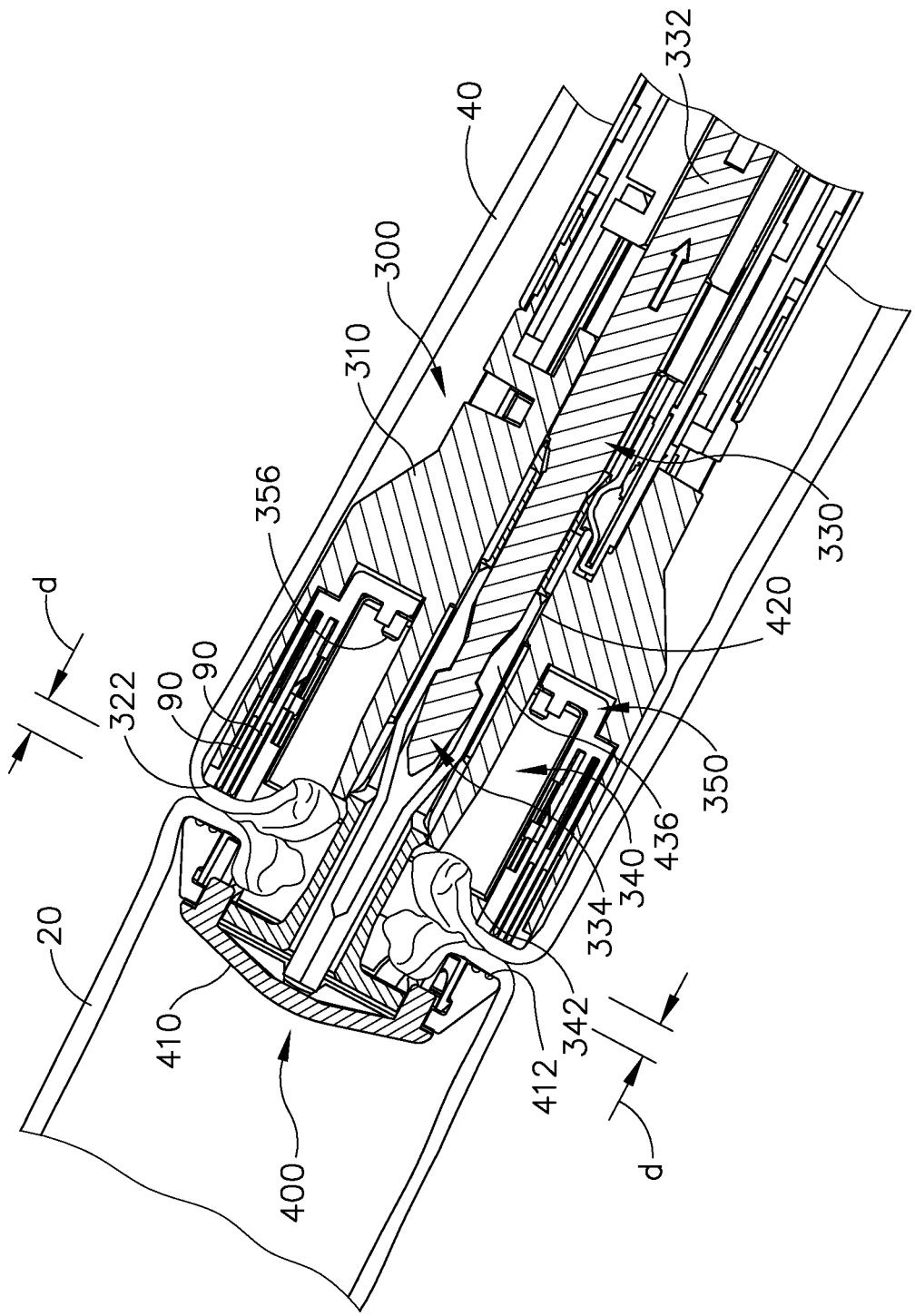
FIG. 21C depicts a cross-sectional side view of the anvil of FIG. 3 positioned within the first section of the digestive tract and the stapling head assembly of FIG. 6 positioned in the second section of the digestive tract, with the anvil retracted toward the stapling head assembly to thereby clamp tissue between the anvil and the stapling head assembly.

FIGS. 21A-21E show instrument (10) being used to form an anastomosis (70) between two tubular anatomical structures (20, 40). By way of example only, the tubular anatomical structures (20, 40) may comprise sections of a patient's esophagus, sections of a patient's colon, other sections of the patient's digestive tract, or any other tubular anatomical structures. As shown in FIG. 21A, anvil (400) is positioned in one tubular anatomical structure (20) and stapling head assembly (300) is positioned in another tubular anatomical structure (40). In versions where tubular anatomical structures (20, 40) comprise sections of a patient's colon, stapling head assembly (300) may be inserted via the patient's rectum. It should also be understood that the procedure depicted in FIGS. 21A-21E is an open surgical procedure, though the procedure may instead be performed laparoscopically. Various suitable ways in which instrument (10) may be used to form an anastomosis (70) in a laparoscopic procedure will be apparent to those of ordinary skill in the art in view of the teachings herein.

As shown in FIG. 21A, anvil (400) is positioned in tubular anatomical structure (20) such that shank (420) protrudes from the open severed end (22) of tubular anatomical structure (20). A purse-string suture (30) is provided about a mid-region of shank (420) to generally secure the position of anvil (400) in tubular anatomical structure (20). Similarly, stapling head assembly (300) is positioned in tubular anatomical structure (40) such that trocar (330) protrudes from the open severed end (42) of tubular anatomical structure (20). A purse-string suture (50) is provided about a mid-region of shaft (332) to generally secure the position of stapling head assembly (300) in tubular anatomical structure (40).

Next, anvil (400) is secured to trocar (330) by inserting trocar (330) into bore (422) as shown in FIG. 21B. Latch members (430) engage head (334) of trocar (330), thereby providing a secure fit between anvil (400) and trocar (330). The operator then rotates knob (130) while holding casing (110) stationary via pistol grip (112). This rotation of knob (130) causes trocar (330) and anvil (400) to retract proximally (as described above with reference to FIGS. 12A-12C). As shown in FIG. 21C, this proximal retraction of trocar (330) and anvil (400) compresses the tissue of tubular anatomical structures (20, 40) between surfaces (412, 322) of anvil (400) and stapling head assembly (300). The operator observes the position of needle (526) within window (114) to determine whether the gap distance (d) between opposing surfaces (412, 322) of anvil (400) and stapling head assembly (300) is appropriate; and makes any necessary adjustments via knob (130).

Once the operator has appropriately set the gap distance (d) via knob (130), the operator actuates safety trigger (140) (as shown in FIG. 12D) to enable actuation of firing trigger (150). The operator then actuates firing trigger (150) (as shown in FIG. 12D). This causes paddle (158) to actuate the switch of a motor activation module (180), thereby activating motor to rotate cam member (700) (as shown in FIGS.

Figure 21D:
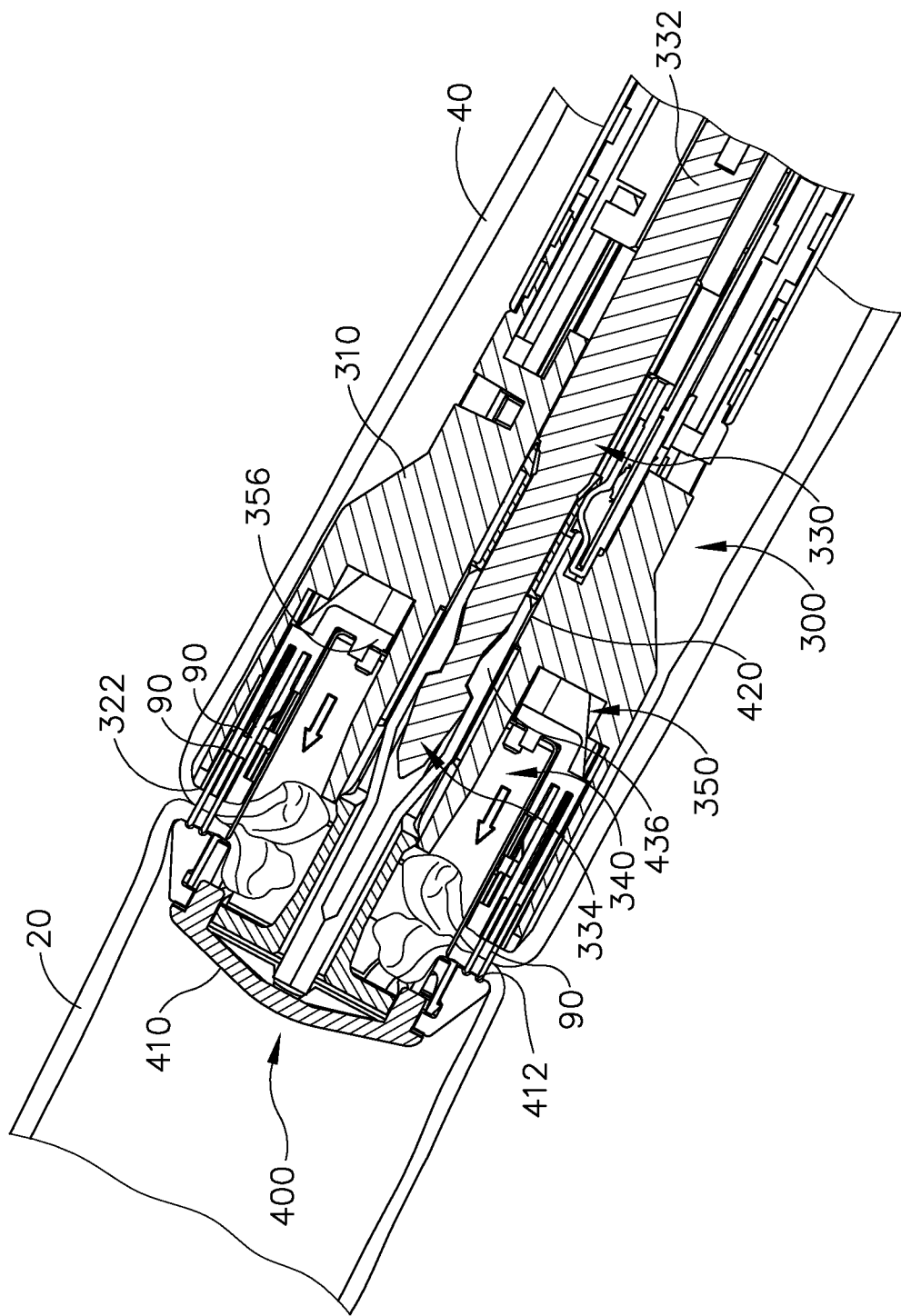
FIG. 21D depicts a cross-sectional side view of the anvil of FIG. 3 positioned within the first section of the digestive tract and the stapling head assembly of FIG. 6 positioned in the second section of the digestive tract, with the stapling head assembly actuated to sever and staple the clamped tissue.

20A-20D). This rotation of cam member (700) actuates stapling head assembly (300) by driving knife member (340) and staple driver member (350) distally as shown in FIG. 21D. As knife member (340) translates distally, cutting edge (342) of knife member (340) cooperates with inner edge (416) of anvil (400), thereby shearing excess tissue that is positioned within annular recess (418) of anvil (400) and the interior of knife member (340).

As shown in FIG. 4, anvil (400) of the present example includes a breakable washer (417) within annular recess (418). This washer (417) is broken by knife member (340) when the knife member (340) completes a full distal range of motion from the position shown in FIG. 21C to the position shown in FIG. 21D. The progressively increasing radius of curvature of second surface region may provide an increasing mechanical advantage as knife member (340) reaches the end of its distal movement, thereby providing greater force by which to break the washer (417). Of course, the breakable washer (417) may be omitted entirely in some versions. In versions where washer (417) is included, it should be understood that washer (417) may also serve as a cutting board for knife member (340) to assist in cutting of tissue. Such a cutting technique may be employed in addition to or in lieu of the above-noted shearing action between inner edge (416) and knife member (340).

As staple driver member (350) translates distally from the position shown in FIG. 21C to the position shown in FIG. 21D, staple driver member (350) drives staples (90) through the tissue of tubular anatomical structures (20, 40) and into staple forming pockets (414) of anvil (400). Staple forming pockets (414) deform the driven staples (90) into a "B" shape as is known in the art. The formed staples (90) thus secure the ends of tissue together.

Figure 21E:
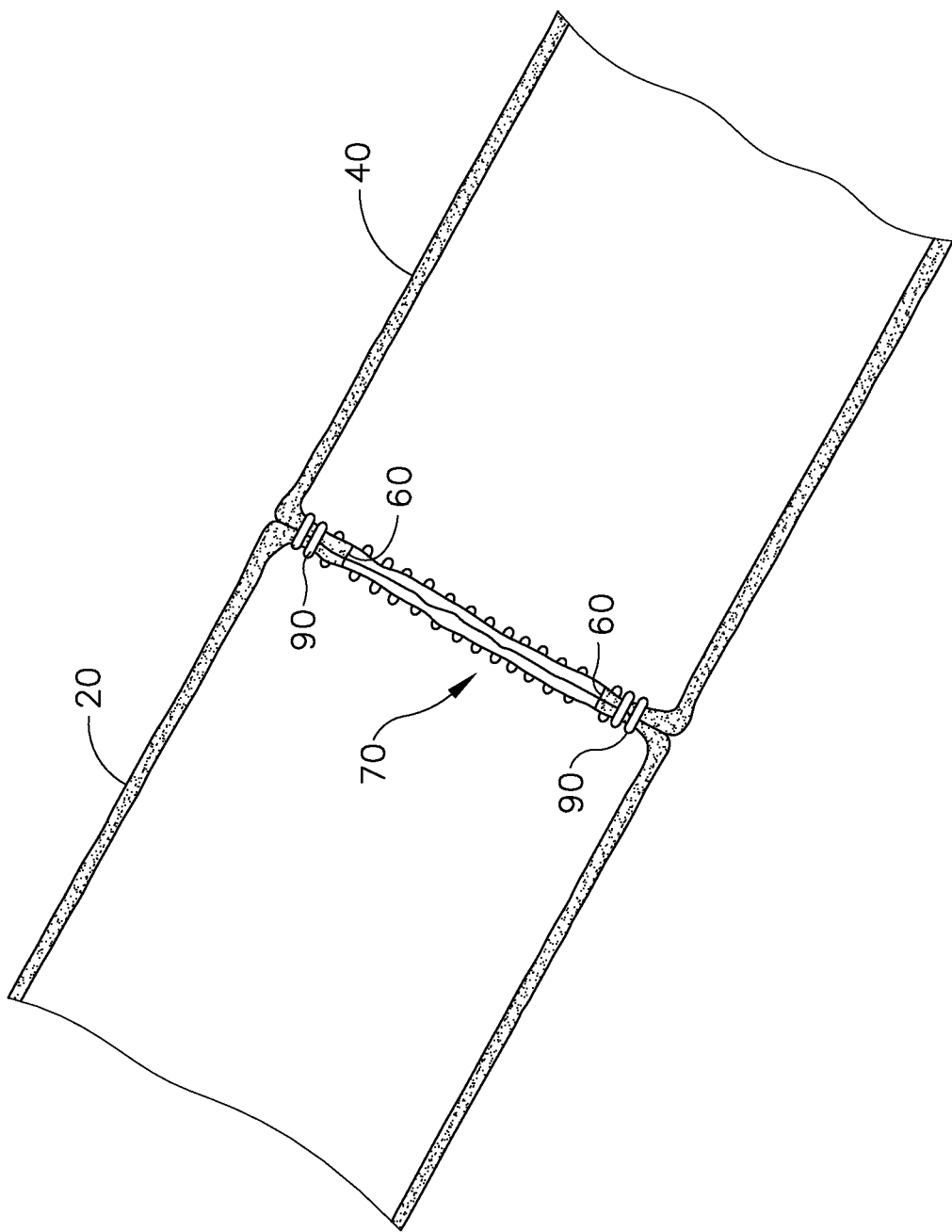
FIG. 21E depicts a cross-sectional side view of the first and second sections of the digestive tract of FIG. 21A joined together at an end-to-end anastomosis.

After the operator has actuated stapling head assembly (300) as shown in FIG. 21D, the operator rotates knob (130) to drive anvil (400) distally away from stapling head assembly (300), increasing the gap distance (d) to facilitate release of the tissue between surfaces (412, 322). The operator then removes instrument (10) from the patient, with anvil (400) still secured to trocar (330). Referring back to the example where the tubular anatomical structures (20, 40) comprise sections of a patient's colon, instrument (10) may be removed via the patient's rectum. With instrument (10) is removed, the tubular anatomical structures (20, 40) are left secured together by two annular arrays of staples (90) at an anastomosis (70) as shown in FIG. 21E. The inner diameter of the anastomosis (70) is defined by the severed edge (60) left by knife member (340).

II. Exemplary Alternative Instruments with Anvil Actuation Lockout Features

Although various lockout features are described above with respect to triggers (140, 150) of instrument (10), it may be desirable to provide lockout features that selectively lock out other features of instrument (10). For instance, in an instrument similar to instrument (10) described above, certain lockout features may be included to lock out actuation of an anvil actuation assembly similar to the anvil actuation assembly described above. In particular, such features may prevent an operator from adjusting gap distance (d) after the operator reaches a particular stage of operation of instrument (10) (e.g., after safety trigger (140) is actuated). In such examples, the ability to prevent adjustment of the gap distance (d) after an appropriate gap distance (d) has already been established may be desirable to ensure that the operator completes the anastomosis procedure in a particular sequence of steps comprising adjusting the gap distance followed by the firing procedure.

Examples of anvil lockout features are described in U.S. Pub. No. 2013/0153631, entitled "Feature to Lock Knob of Tissue Stapler," published Jun. 20, 2013, issued as U.S. Pat. No. 9,220,505 on Dec. 29, 2015, the disclosure of which is incorporated by reference herein. While various alternative instruments are described below, other examples will be apparent to those of ordinary skill in the art in view of the teachings herein. It should be further understood that various features and/or structures of the instruments described below may be readily incorporated with other instruments described herein.

A. Exemplary Instrument with Anvil Actuation Rod Lockout Feature

Figure 22:
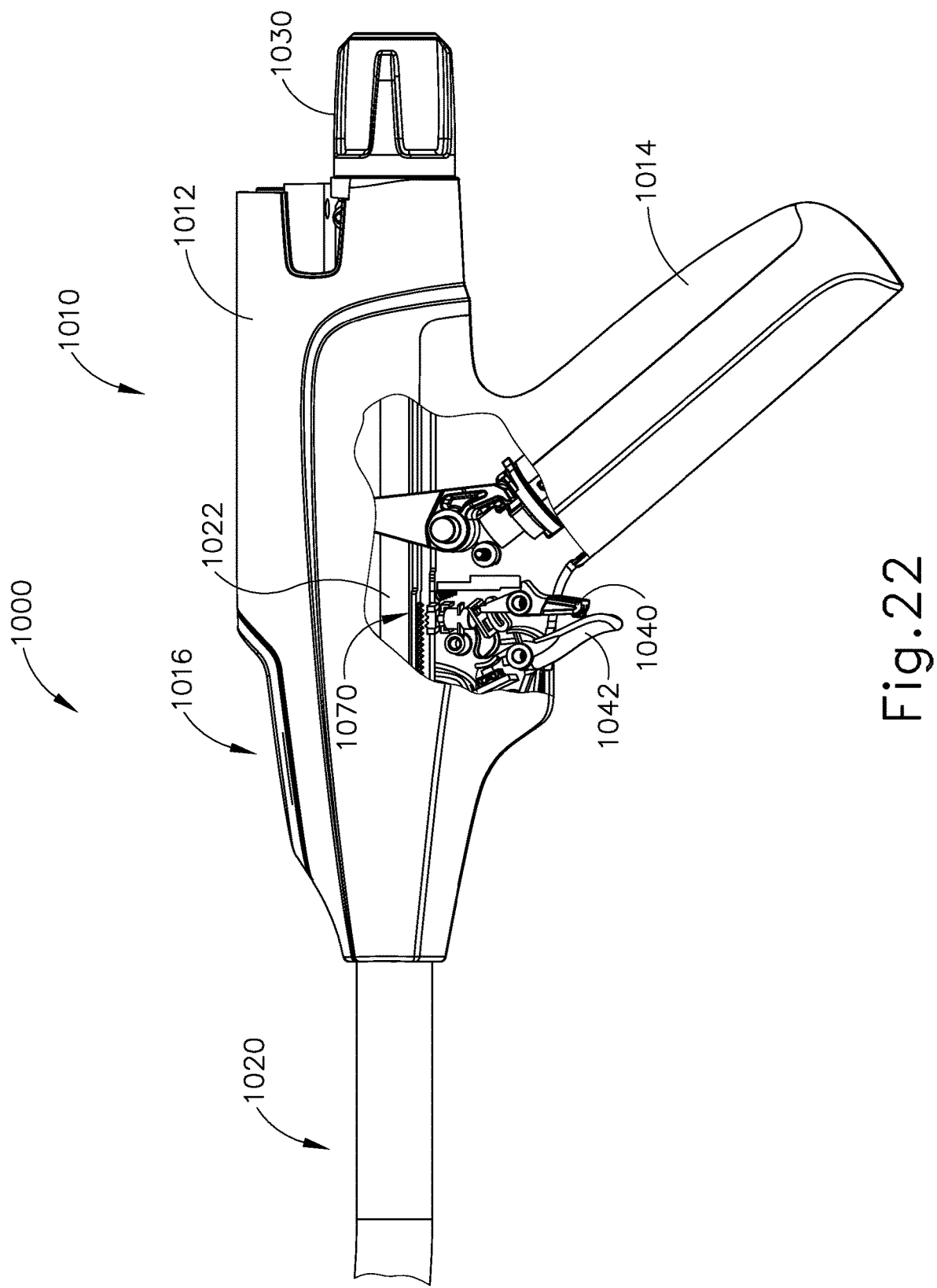
FIG. 22 depicts a side cut-away view of a handle assembly of an exemplary alternative circular stapler.

FIG. 22 shows an exemplary alternative surgical circular stapling instrument (1000) that may be used to provide an end-to-end anastomosis between two sections of an anatomical lumen such as a portion of a patient's digestive tract. It should be understood that instrument (1000) of the present example is substantially the same as instrument (10) described above unless otherwise noted herein. For instance, like with instrument (10), instrument (1000) comprises a handle assembly (1010), a shaft assembly (1020), a stapling head assembly (not shown), and an anvil (not shown). Handle assembly (1010) is substantially the same has handle assembly (110) described above and comprises a casing (1012) defining an obliquely oriented pistol grip (1014). Handle assembly (1010) further includes a window (1016) that permits viewing of a movable indicator needle (not shown) as similarly described above.

Like with instrument (10) described above, instrument (1000) is controlled by an operator via knob (1030) and triggers (1040, 1042). Knob (1030), like with knob (130) described above, is operatively connected to shaft assembly (1020) to actuate the anvil. In particular, knob (1030) is rotatable to engage threads (not shown) of shaft assembly (1020) to translate a trocar actuation rod (1022), which ultimately actuates the anvil as similarly described above with respect to shaft assembly (200) of instrument (10).

Triggers (1040, 1042) function similarly to triggers (140, 150) described above. For instance, a safety trigger (1040) may be first actuated by an operator to unblock a firing trigger (1042), to thereby enable activation of the stapling head assembly. Like with safety trigger (140) described above, safety trigger (1040) includes a first upright member (1044) that is generally operable to permit actuation of safety trigger (1040) only after the anvil has been adjusted to define a gap distance (d) that is within a clinically acceptable range. In particular, trocar actuation rod (1022) is operatively connected to a bracket (1024), which includes at least one slot (1026). As similarly described above with respect to slot (506), slot (1026) is configured to receive at least a portion of first upright member (1044) to thereby permit movement of safety trigger (1040). Although not shown, it should be understood that firing trigger (1042) may also include an upright member (not shown) similar to second upright member (154) described above.

Firing trigger (1042) is similar to firing trigger (150) described above. In particular, once safety trigger (1040) has been activated, firing trigger (1042) is operable to initiate actuation of the stapling head assembly. Firing trigger (1042) includes a paddle (1046), which is configured to engage a motor activation module (1050) when firing trigger (1042) is actuated by an operator. Like with motor activation module (180) described above, motor activation module (1050) of the present example initiates the stapling sequence by activating a motor (not shown). The motor then drives a cam member (1052), which in turn drives a cam follower (1054). Cam member (1052) and cam follower (1054) are substantially the same as cam member (700) and cam follower (600) described above, such that cam member (1052) and cam follower (1054) cooperate to drive the stapling head assembly through a stapling sequence.

Figure 23:
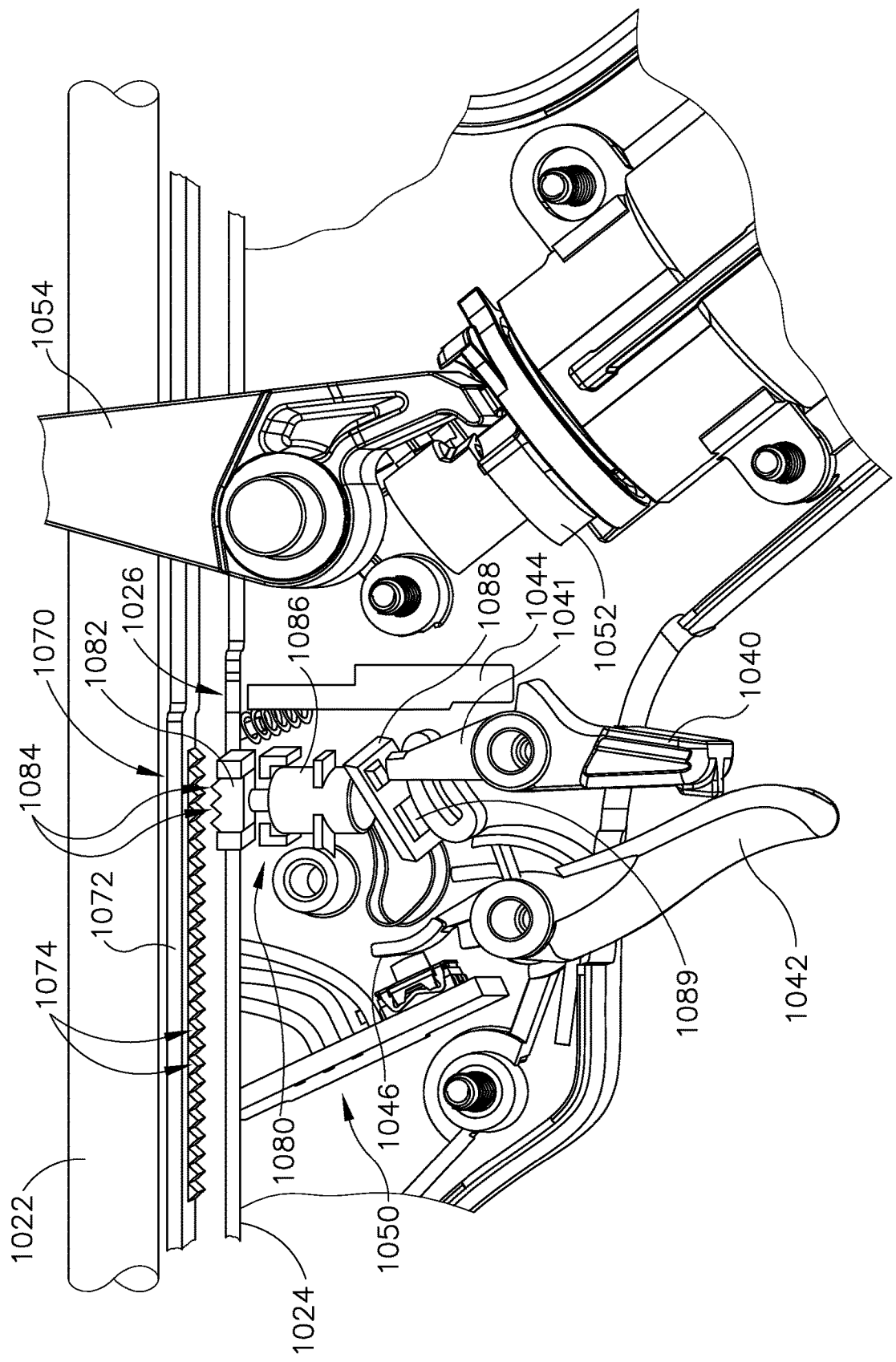
FIG. 23 depicts a side elevational view of an anvil lockout assembly of the handle assembly of FIG. 22, with the anvil lockout assembly in an unlocked position.

Unlike instrument (10) described above, instrument (1000) of the present example comprises an anvil lockout assembly (1070). Anvil lockout assembly (1070) is generally configured to prevent further adjustment of the longitudinal position of the anvil once safety trigger (1040) is actuated. Such a feature may be desirable because lockout of the anvil may prevent an operator from improperly changing the gap distance (d) once a suitable gap (d) distance is reached. Anvil lockout assembly (1070) comprises a lockout member (1072), and an actuation assembly (1080). As is best seen in FIG. 23, lockout member (1072) is fixedly secured to trocar actuation rod (1022). Lockout member (1072) of the present example includes a plurality of triangular teeth (1074) extending downwardly from lockout member (1072). As will be described in greater detail below, teeth (1074) are configured to engage with corresponding teeth (1084) of actuation assembly (1080) to prevent translation of trocar actuation rod (1022).

Although lockout member (1072) of the present example is shown as including teeth (1074), it should be understood that in other examples any other suitable surfacing treatment may be used. For instance, in some examples lockout member (1072) includes a knurled surface, bumps, ridges, detent features, or any other suitable surface treatment or geometry that may be configured to engage with a corresponding surface of actuation assembly (1080) to prevent translation of trocar actuation rod (1022). Additionally, although lockout member (1072) of the present example is shown as being fixedly secured to trocar actuation rod (1022), it should be understood that no such limitation is intended. For instance, in other examples lockout member (1072) is of integral construction with bracket (1024). In such examples, lockout member (1072) may include various features such as slots and/or channels, in addition to teeth (1074), to permit the same functionality of bracket (1024) described above. Of course, various other configurations of lockout member (1072) will be apparent to those of ordinary skill in the art in view of the teachings herein.

Actuation assembly (1080) comprises a lock block (1082), an actuator (1086), and an activation board (1088). Lock block (1082) includes a plurality of teeth (1084), which correspond to teeth (1074) of lockout member (1072). As will be described in greater detail below, lock block (1082) is generally configured to engage with lockout member (1072) to prevent translation of trocar actuation rod (1022).

Lock block (1082) is attached to a portion of actuator (1086). Generally, actuator (1086) is configured to selectively drive lock block (1082) upwardly into engagement with lockout member (1072). Actuator (1086) of the present example comprises a solenoid, although any other suitable mechanical or electro-mechanical actuation mechanism may be used. Actuator (1086) is in communication with activation board (1088). Generally, activation board (1088) is operable to activate actuator (1086) to initiate movement of actuator (1086) to thereby drive lock block (1082) into engagement with lockout member (1072). Activation board (1088) of the present example comprises a button (1089) that is integrated into a printed circuit board. Although not shown, it should be understood that activation board (1088) may include other components suitable for communicating an electrical signal to actuator (1086) such as resistors, capacitors, integrated circuit boards, etc.

Button (1089) is adjacent to safety trigger (1040). As will be described in greater detail below, safety trigger (1040) includes an activation arm (1041) that moves in conjunction with safety trigger (1040) to engage button (1089). Although button (1089) of the present example is shown as an electromechanical push button, it should be understood that in other examples button (1089) may comprise any other suitable electrical switching mechanism. In still other examples, button (1089) may be omitted. In lieu of button (1089), a sensor may be used to replicate the functionality of button (1089) without necessarily requiring direct physical contact between activation board (1088) and safety trigger (1040). Additionally, it should be understood that in examples where actuator (1086) is an entirely mechanical actuator, activation board (1088) may be omitted entirely and safety trigger (1040) may instead be mechanically coupled to actuator (1086) via gears, cams, shafts, etc.

Figure 24:
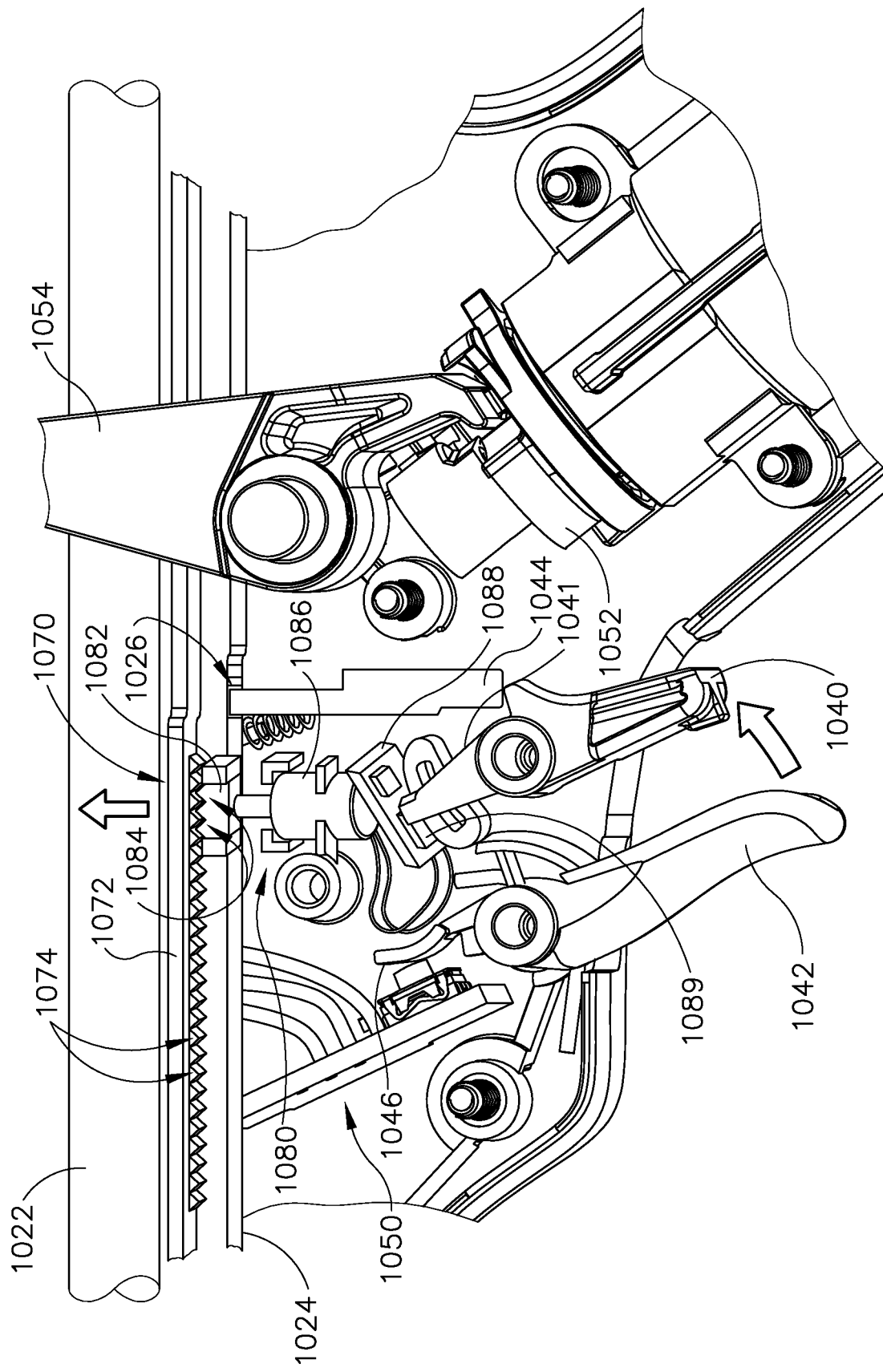
FIG. 24 depicts another side elevational view of the anvil lockout assembly of FIG. 23, with the anvil lockout assembly in a locked position.
Figure 25:
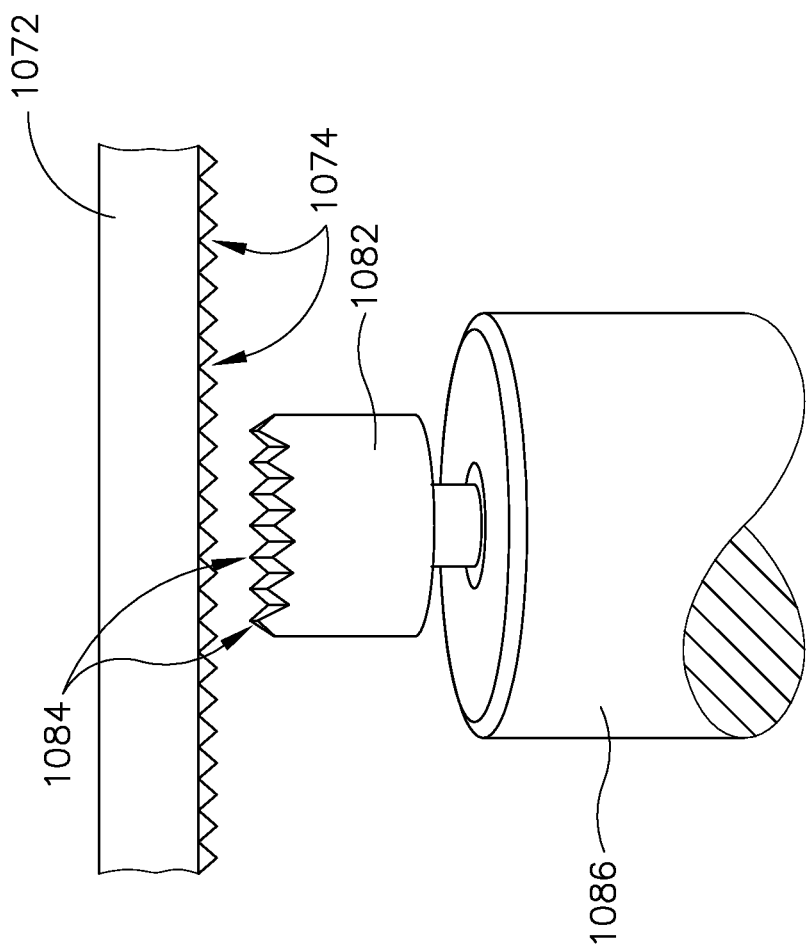
FIG. 25 depicts a detailed side elevational view of the anvil lockout assembly of FIG. 23, with the anvil lockout assembly in the unlocked position.

FIGS. 23-26 show an exemplary sequence of operation of anvil lockout assembly (1070). As can be seen in FIGS. 23 and 25, anvil lockout assembly (1070) initially begins in an unlocked state. In such a state, lock block (1082) is positioned away from lockout member (1072) such that trocar actuation rod (1022) is movable via knob (1030). In particular, safety trigger (1040) is positioned in a non-actuated position such that activation arm (1041) is disposed away from button (1089) of activation board (1088). With activation arm (1041) positioned away from button (1089), activation board (1088) is in an open circuit condition such that no signal is communicated to actuator (1086). Because actuator (1086) of the present example is a solenoid, the open circuit condition of activation board (1088) results in actuator (1086) being in a non-active condition thereby positioning lock block (1082) away from lockout member (1072). Although the unlocked state is described herein as being associated with activation board (1088) being in the open circuit condition, it should be understood that in examples using alternative actuators (1086) described above, activation board (1088) may provide numerous alternative signals to actuator (1086) that correspond to the particular actuator (1086) being used.

Figure 26:
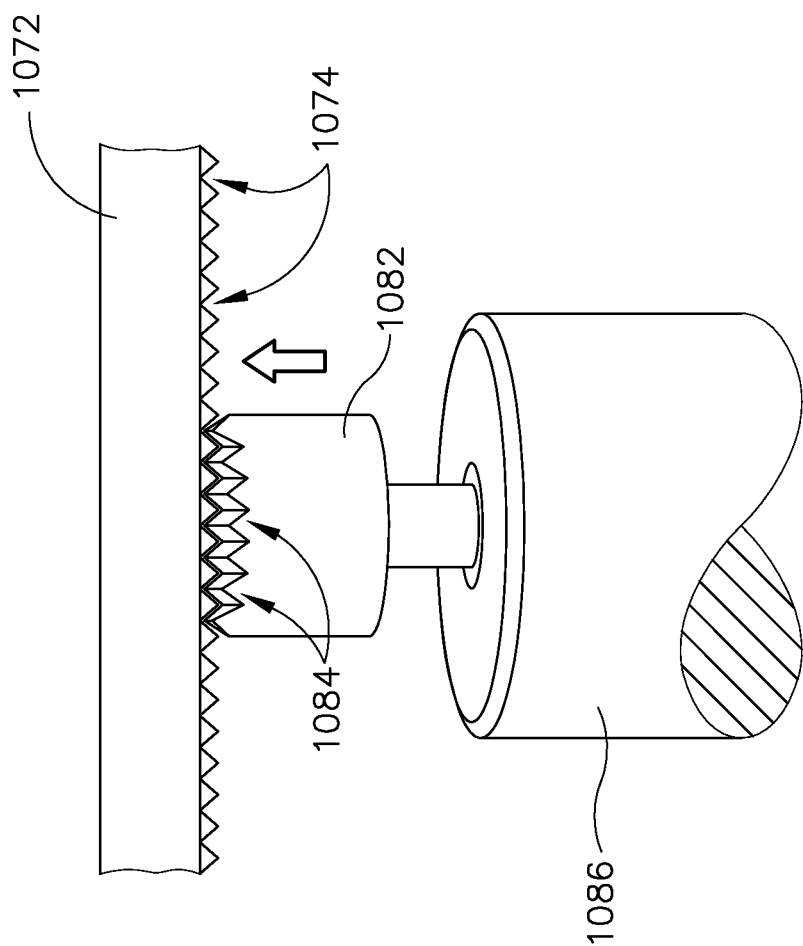
FIG. 26 depicts another detailed side elevational view of the anvil lockout assembly of FIG. 23, with the anvil lockout assembly in the locked position.

FIGS. 24 and 26 show anvil lockout assembly (1070) in a locked state. To transition anvil lockout assembly (1070) to the locked state, an operator may pivot safety trigger (1040) proximally. Proximal movement of safety trigger (1040) correspondingly moves activation arm (1041) toward button (1089) of activation board (1088) until activation arm (1041) engages button (1089). Once an operator as moved safety trigger (1040) to engage button (1089), anvil lockout assembly (1070) will automatically transition to the locked state without further operator intervention. In particular, engagement between button (1089) and activation arm (1041) causes activation board (1088) to transition to a closed circuit condition. When activation board (1088) is in the closed circuit condition, activation board (1088) communicates a signal to actuator (1086). Actuator (1086) then responds to such a signal by driving lock block (1082) upwardly and into engagement with lockout member (1072). With lock block (1082) engaged with lockout member (1072), teeth (1074, 1084) mesh, thereby locking translation of trocar actuation rod (1022).

In some variations, instrument (1000) is also configured to selectively activate actuator (1086) based whether battery pack (120) is fully inserted in socket (116). By way of example only, instrument (1000) may be configured such that anvil lockout assembly (1070) remains in the locked state (by default) until battery pack (120) is fully inserted in socket (116). Once battery pack (120) is fully inserted into socket (116), actuator (1086) is automatically activated transition anvil lockout assembly (1070) to the unlocked state. Anvil lockout assembly (1070) may remain in the unlocked state until the operator pivots safety trigger (1040) proximally as noted above. Once the operator pivots safety trigger (1040) proximally, anvil lockout assembly (1070) may again be transitioned back to the locked state as noted above.

It should therefore be understood that anvil lockout assembly (1070) may prevent translation of trocar actuation rod (1022) when either of the two following conditions are present: (a) battery pack (120) is not fully inserted in socket (116), or (b) safety trigger (1040) has been pivoted proximally. However, anvil lockout assembly (1070) will permit translation of trocar actuation rod (1022) when both of the two following conditions are present: (a) battery pack (120) is fully inserted in socket (116), and (b) safety trigger (1040) has not yet been pivoted proximally.

Various suitable features that may be used to provide activation of anvil lockout assembly (1070) in response to insertion of battery pack (120) into socket (116) will be apparent to those of ordinary skill in the art in view of the teachings herein.

B. Exemplary Instrument with Knob Lockout Actuation Feature

Figure 27:
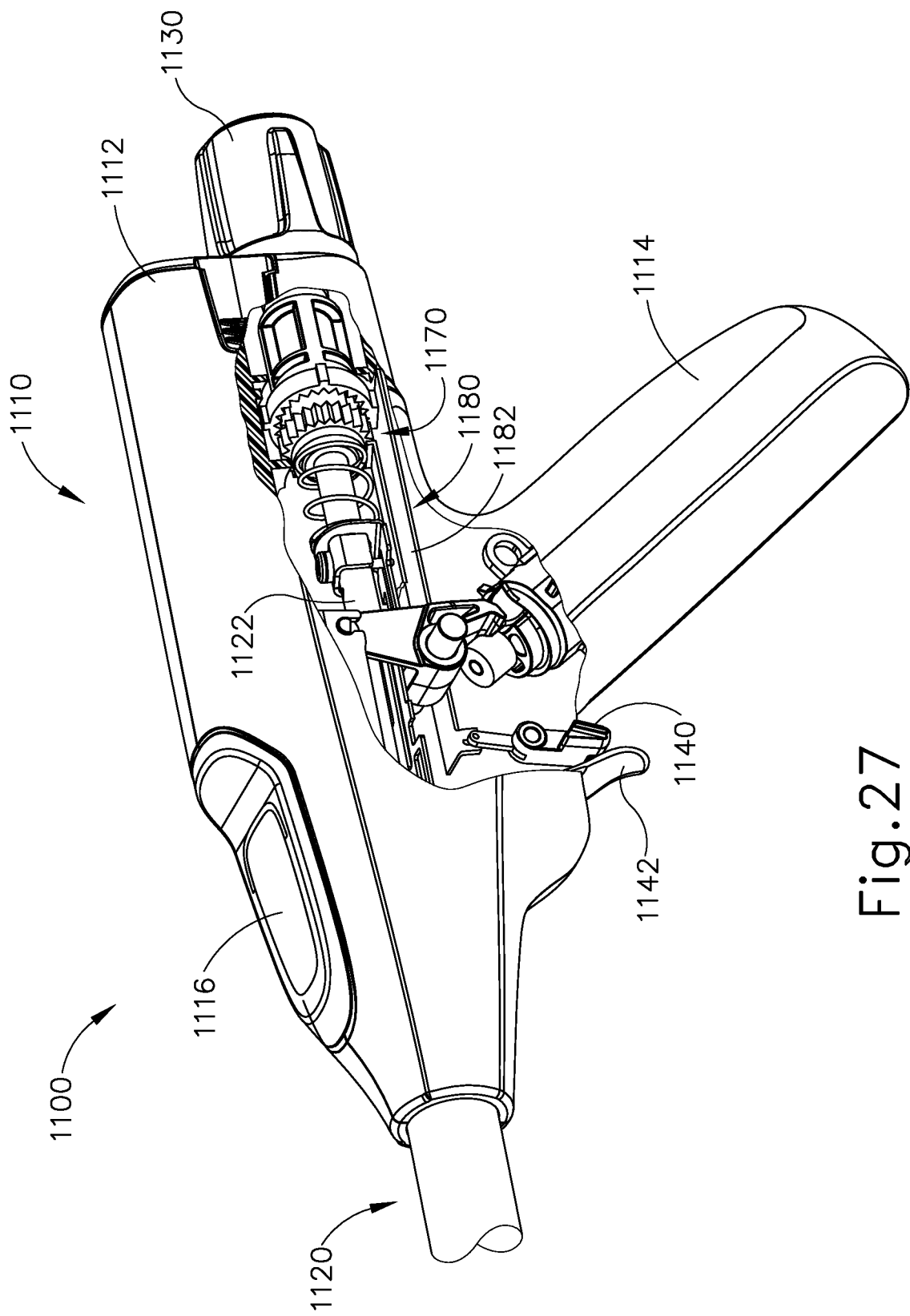
FIG. 27 depicts a detailed perspective cut-away view of a handle assembly of another exemplary alternative circular stapler.
Figure 28:
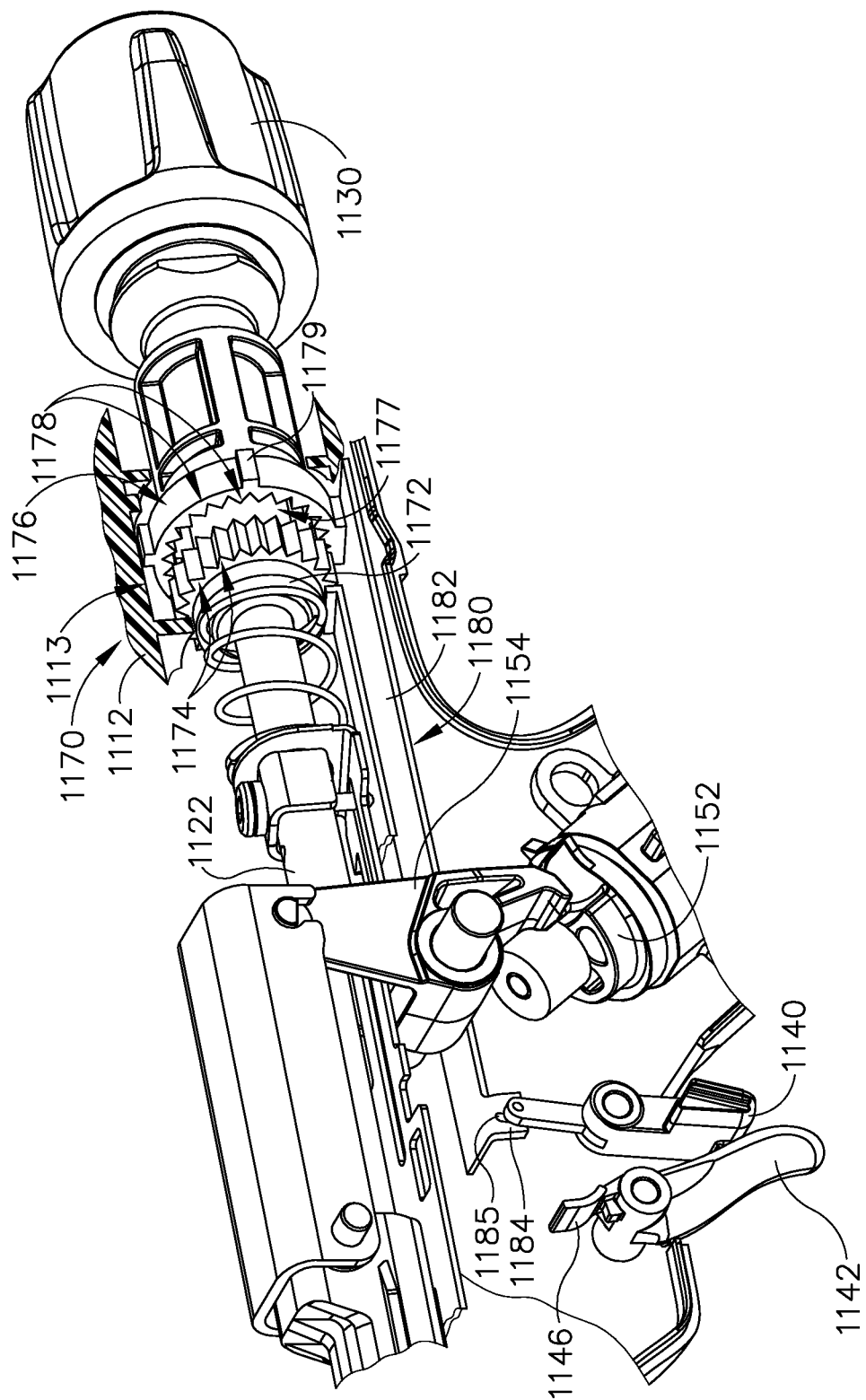
FIG. 28 depicts a detailed perspective view of an anvil actuation assembly of the handle assembly of FIG. 27.

FIG. 27 shows another exemplary alternative surgical circular stapling instrument (1100) that may be used to provide an end-to-end anastomosis between two sections of an anatomical lumen such as a portion of a patient's digestive tract. It should be understood that instrument (1100) of the present example is substantially the same as instrument (10) described above unless otherwise noted herein. For instance, like with instrument (10), instrument (1100) comprises a handle assembly (1110), a shaft assembly (1120), a stapling head assembly (not shown), and an anvil (not shown). Handle assembly (1110) is substantially the same has handle assembly (110) described above and comprises a casing (1112) defining an obliquely oriented pistol grip (1114). Handle assembly (1110) further includes a window (1116) that permits viewing of a movable indicator needle (not shown) as similarly described above.

Like with instrument (10) described above, instrument (1100) is controlled by an operator via knob (1130) and triggers (1140, 1142). Knob (1130), like with knob (130) described above, is operatively connected to shaft assembly (1120) to actuate the anvil. In particular, knob (1130) is rotatable to engage threads (not shown) of shaft assembly (1120) to translate a trocar actuation rod (1122), which ultimately actuates the anvil as similarly described above with respect to shaft assembly (200) of instrument (10).

Triggers (1140, 1142) function similarly as triggers (140, 150) described above. For instance, a safety trigger (1140) may be first actuated by an operator to unblock a firing trigger (1142), to thereby enable activation of the stapling head assembly. Although not shown, it should be understood that like with safety trigger (140) described above, safety trigger (1140) may include an upright member (not shown) that is generally operable to permit actuation of safety trigger (1140) only after the anvil has been adjusted to define a gap distance (d) that is within a clinically acceptable range. Additionally, it should be understood that firing trigger (1142) may also include an upright member (not shown) similar to second upright member (154) described above. Of course, in other examples the upright members may be omitted entirely.

Firing trigger (1142) is similar to firing trigger (150) described above. In particular, once safety trigger (1140) has been activated, firing trigger (1142) is operable to initiate actuation of the stapling head assembly. Firing trigger (1142) includes a paddle (1146), which is configured to engage a motor activation module (not shown) when firing trigger (1142) is advanced by an operator. Like with motor activation module (180) described above, the motor activation module of the present example initiates the stapling sequence by activating a motor (not shown). The motor then drives a cam member (1152), which in turn drives a cam follower (1154). Cam member (1152) and cam follower (1154) are substantially the same as cam member (700) and cam follower (600) described above, such that cam member (1152) and cam follower (1154) cooperate to drive the stapling head assembly through a stapling sequence.

Figure 29:
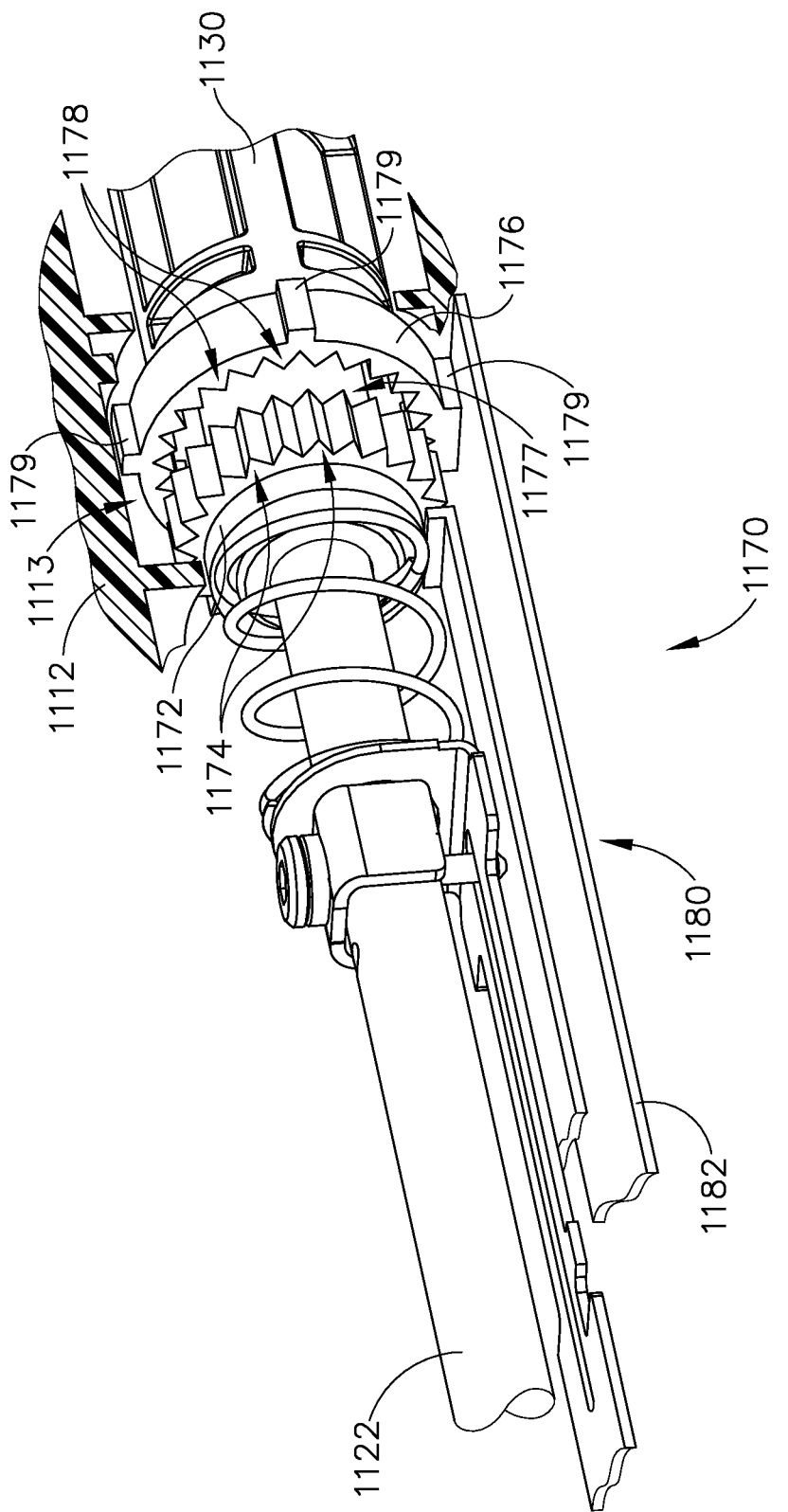
FIG. 29 depicts a detailed perspective view of an anvil lockout assembly of the anvil actuation assembly of FIG. 28, with the anvil lockout assembly in an unlocked position.

Unlike instrument (10) described above, instrument (1100) of the present example comprises an anvil lockout assembly (1170). Anvil lockout assembly (1170) is generally configured to prevent further adjustment of the longitudinal position of the anvil once safety trigger (1140) is actuated. Such a feature may be desirable because lockout of the anvil may prevent an operator from improperly changing the gap distance (d) once a suitable gap distance (d) is reached. Anvil lockout assembly (1170) comprises an inner lockout member (1172), an outer lockout member (1176), and an actuation member (1180). As is best seen in FIG. 29, inner lockout member (1172) is disposed about a portion of a portion of knob (1130) and is fixedly secured thereto. Inner lockout member (1172) of the present example includes a plurality of triangular teeth (1174) extending radially outwardly from inner lockout member (1172). As will be described in greater detail below, teeth (1174) are configured to engage with corresponding teeth (1184) of outer lockout member (1176) to prevent rotation of knob (1130), thereby preventing translation of trocar actuation rod (1122).

Outer lockout member (1176) has a generally cylindrical shape and defines an opening (1177) that is sized to receive inner lockout member (1172). The inner diameter of outer lockout member (1176) defines a plurality of teeth (1178), which correspond to teeth (1147) of inner lockout member (1172). As will be described in greater detail below, teeth (1178) are configured to engage teeth (1174) of inner lockout member (1172) to prevent further adjustment of the longitudinal position of anvil, by preventing further rotation of knob (1130). Outer lockout member (1176) further includes a plurality of protrusions (1179) protruding radially outwardly from the outer diameter of outer lockout member (1176). Protrusions (1179) are disposed in corresponding channels (1113) within casing (1112) to rotationally fix outer lockout member (1176) in position while still permitting at least some translation.

Although inner and outer lockout members (1172, 1176) of the present example are shown as including teeth (1174, 1178), it should be understood that in other examples any other suitable surfacing treatment or geometry may be used. For instance, in some examples lockout members (1172, 1176) include corresponding knurled surfaces, bumps, splines, ridges, detent features, or any other suitable surface treatment or geometry that may be configured to correspondingly engage to prevent relative rotational movement between lockout members (1172, 1176).

Actuation member (1180) comprises an elongate body (1182) extending from outer lockout member (1176) to safety trigger (1140). In particular, body (1182) includes a trigger bracket (1184) that is configured to couple with safety trigger (1140). Trigger bracket (1184) includes a channel (1185) that permits bracket (1184) to be pivotably coupled to safety trigger (1140). Similarly, the proximal end of body (1182) is configured to couple with at least one protrusion (1179) of outer lockout member (1176). Accordingly, movement of safety trigger (1140) is transferred to outer lockout member (1176) via actuation member (1180). In other words, outer lockout member (1176) translates longitudinally in response to pivoting of safety trigger (1140). As will be described in greater detail below, outer lockout member (1176) is generally responsive to safety trigger (1140) to selectively lock actuation of the anvil.

Figure 30:
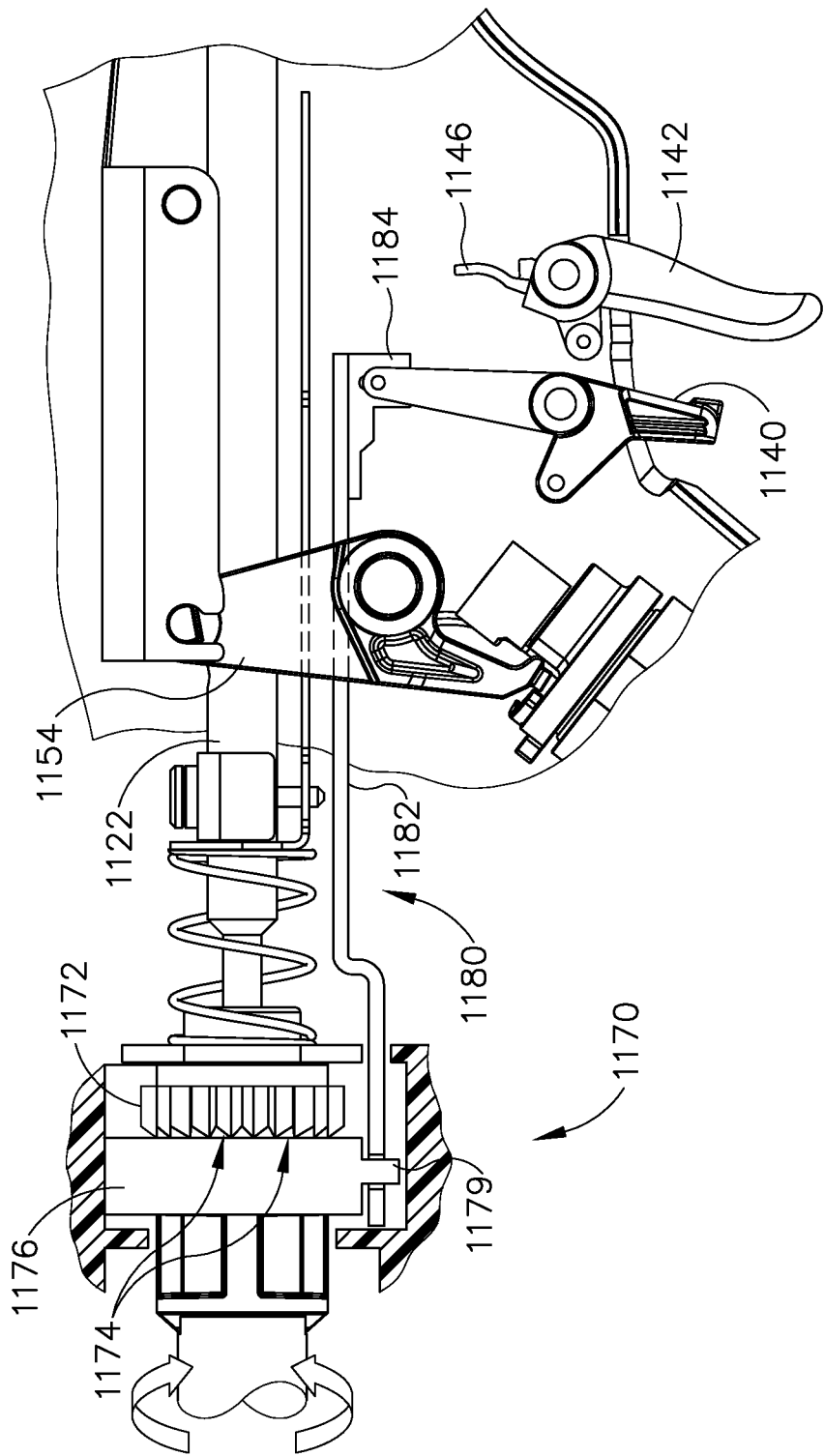
FIG. 30 depicts a detailed side elevational view of the anvil actuation assembly of FIG. 28, with the anvil lockout assembly of FIG. 29 in the unlocked position.
Figure 31:
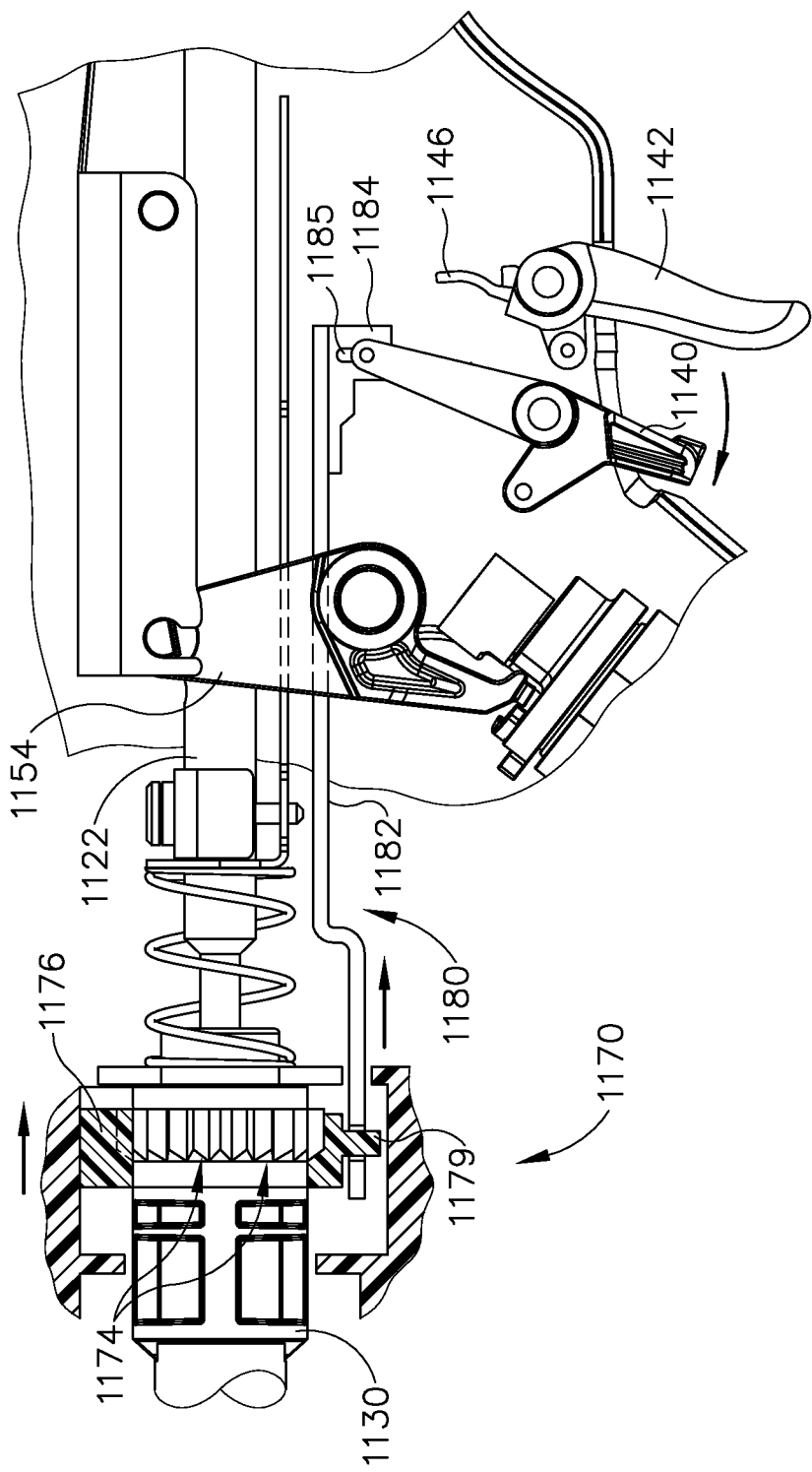
FIG. 31 depicts another detailed side elevational view of the anvil actuation assembly of FIG. 28, with the anvil lockout assembly of FIG. 29 in a locked position.
Figure 32:
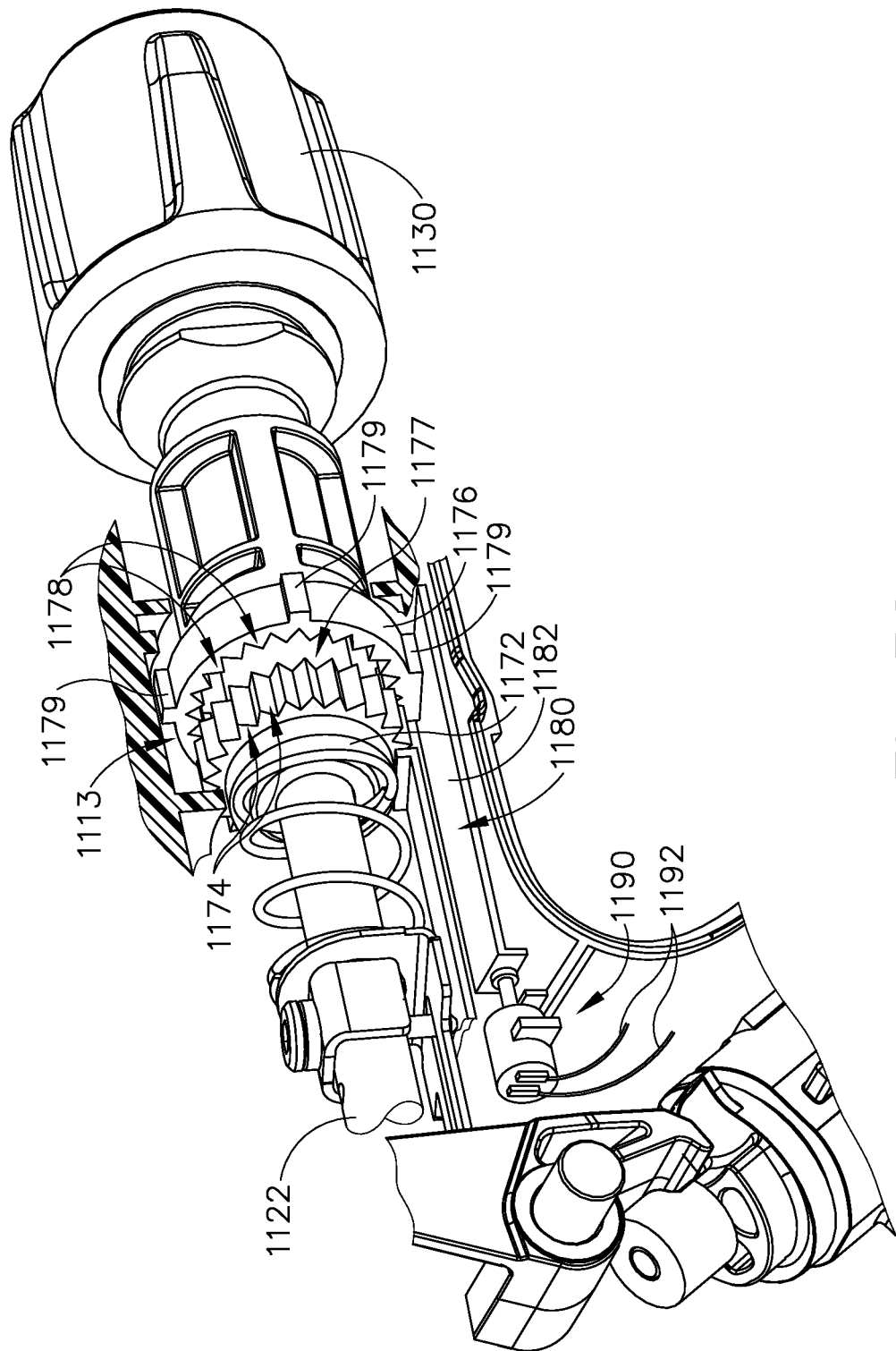
FIG. 32 depicts a detailed perspective view of an alternative configuration of the anvil lockout assembly of FIG. 29.

FIGS. 30-32 show an exemplary sequence of operation of anvil lockout assembly (1170). As can be seen in FIG. 30, anvil lockout assembly (1170) initially begins in an unlocked state. In such a state, outer lockout member (1176) is positioned proximally away from inner lockout member (1172) such that inner lockout member (1172) is freely rotatable relative to outer lockout member (1176). It should be understood that when inner lockout member (1172) is freely rotatable, knob (1130) is similarly freely rotatable such that the longitudinal position of the anvil may be adjusted via trocar actuation rod (1122).

Once the operator has rotated knob (1130) to adjust the longitudinal position of the anvil to achieve an appropriate gap distance (d), it may be desirable to prevent further adjustment of the longitudinal position of the anvil. FIG. 31 shows anvil lockout assembly (1170) in a locked state. To advance anvil lockout assembly (1170) to the locked state, the operator may pivot safety trigger (1140) proximally. Proximal movement of safety trigger (1140) causes safety trigger (1140) to drive actuation member (1180) distally.

Distal movement of actuation member (1180) results in corresponding movement of outer lockout member (1176). As outer lockout member (1176) is moved distally, teeth (1178) of outer lockout member (1176) will begin to engage teeth (1174) of inner lockout member (1176). Once teeth (1178) of outer lockout member (1176) fully engage with teeth (1174) of inner lockout member (1176), outer lockout member (1176) will prevent relative rotational movement of inner lockout member (1172) via protrusions (1179) and casing (1112). Because inner lockout member (1172) is fixedly secured to knob (1130), rotational movement of knob (1130) will also be prevented. With knob (1130) locked in position, further adjustment of the longitudinal position of the anvil will be prevented. With further adjustment of the longitudinal position of the anvil prevented, the operator may then actuate firing trigger (1142) to initiate the stapling sequence as described above with respect to instrument (10).

In some examples, it may be desirable to drive outer lockout member (1176) using other actuation means instead of a mechanical connection as described above. One merely exemplary alternative configuration of instrument (1100) is shown in FIG. 32. As can be seen, instrument (1100) is alternatively equipped with an actuation mechanism (1190) such as a solenoid. Actuation mechanism (1190) is aligned with the longitudinal axis of actuation member (1180) and is fixedly secured to actuation member (1180). To accommodate actuation mechanism (1190), actuation member (1180) may be shortened or otherwise modified to intersect with actuation mechanism (1190). Actuation mechanism (1190) includes a plurality of wires (1192) that may connect to a circuit board, switch, and/or sensor. Although not shown, it should be understood that actuation mechanism (1190) may be actuated using safety trigger (1140) using a similar configuration as safety trigger (1040) of instrument (1000) described above. For instance, actuation of safety trigger (1140) may complete a circuit that activates actuation mechanism (1190), thereby driving lockout member (1176) longitudinally into engagement with lockout member (1172).

In operation, actuation mechanism (1190) generally provides the same function as safety trigger (1140), except actuation mechanism (1190) removes the necessity for actuation member (1180) to extend the entire distance to safety trigger (1140). Although actuation mechanism (1190) is shown and described herein as comprising a solenoid, it should be understood that any other suitable actuator may be used as will be apparent to those of ordinary skill in the art in view of the teachings herein.

In some variations, instrument (1100) is also configured to selectively activate actuation mechanism (1190) based whether battery pack (120) is fully inserted in socket (116). By way of example only, instrument (1100) may be configured such that anvil lockout assembly (1170) remains in the locked state (by default) until battery pack (120) is fully inserted in socket (116). Once battery pack (120) is fully inserted into socket (116), actuation mechanism (1190) is automatically activated transition anvil lockout assembly (1170) to the unlocked state. Anvil lockout assembly (1170) may remain in the unlocked state until the operator pivots safety trigger (1140) proximally as noted above. Once the operator pivots safety trigger (1140) proximally, anvil lockout assembly (1170) may again be transitioned back to the locked state as noted above.

It should therefore be understood that anvil lockout assembly (1170) may prevent translation of trocar actuation rod (1122) when either of the two following conditions are present: (a) battery pack (120) is not fully inserted in socket (116), or (b) safety trigger (1140) has been pivoted proximally. However, anvil lockout assembly (1170) will permit translation of trocar actuation rod (1122) when both of the two following conditions are present: (a) battery pack (120) is fully inserted in socket (116), and (b) safety trigger (1140) has not yet been pivoted proximally.

Figure 33:
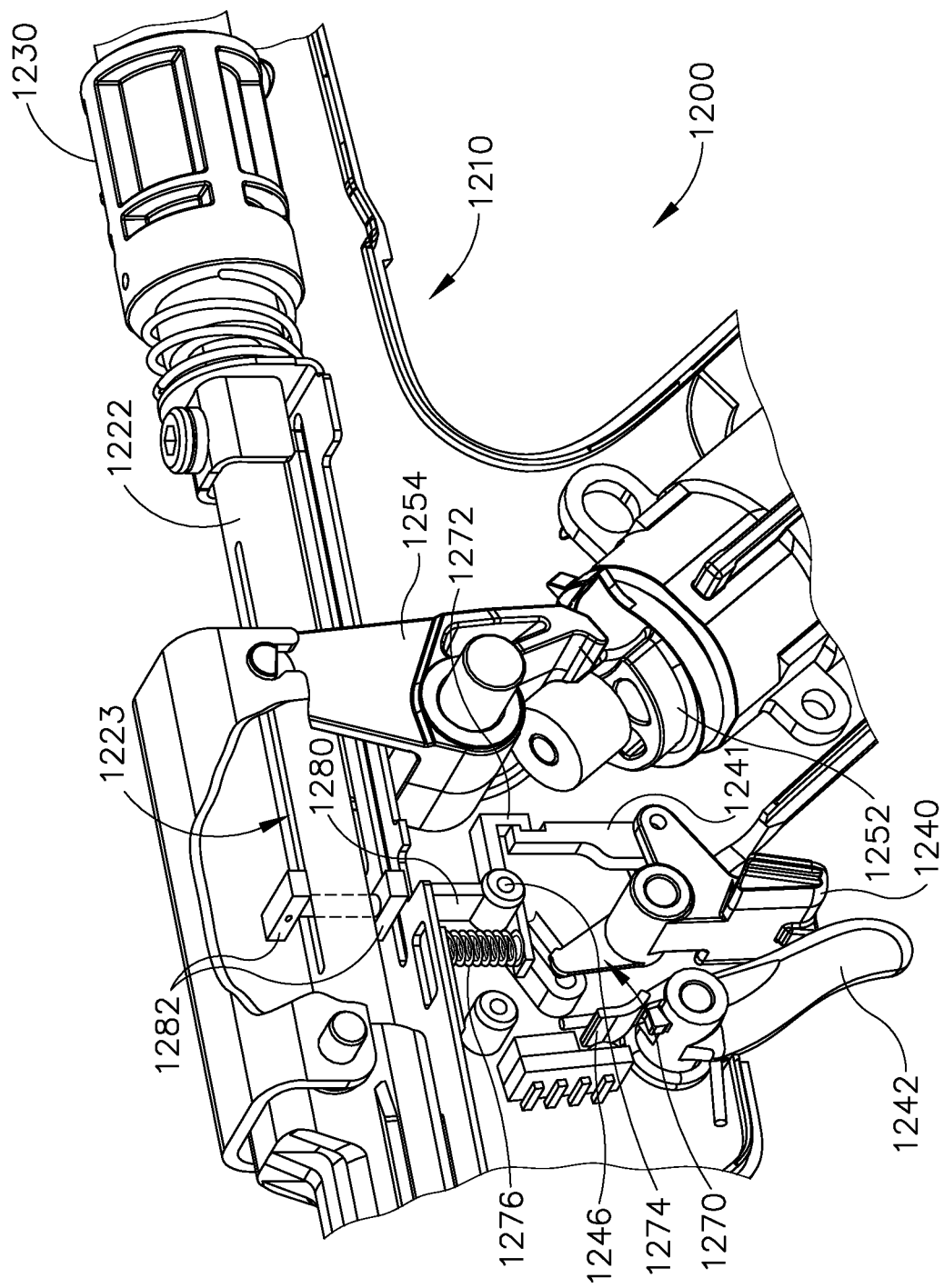
FIG. 33 depicts a detailed perspective cut-away view of yet another exemplary alternative anvil lockout assembly.

Various suitable features that may be used to provide activation of anvil lockout assembly (1170) in response to insertion of battery pack (120) into socket (116) will be apparent to those of ordinary skill in the art in view of the teachings herein III. Exemplary Alternative Lockout Features A. Exemplary Rotatable Anvil Lockout Assembly FIG. 33 shows still another exemplary alternative instrument (1200) that may be used to provide an end-to-end anastomosis between two sections of an anatomical lumen such as a portion of a patient's digestive tract. It should be understood that instrument (1200) of the present example is substantially the same as instrument (10) described above unless otherwise noted herein. For instance, like with instrument (10), instrument (1200) comprises a handle assembly (1210), a shaft assembly (not shown), a stapling head assembly (not shown), and an anvil (not shown). Handle assembly (1210) is substantially the same has handle assembly (110) described above such that further details will not be described herein.

Like with instrument (10) described above, instrument (1200) is controlled by an operator via knob (1230) and triggers (1240, 1242). Knob (1230), like with knob (130) described above, is operatively connected to the shaft assembly to actuate the anvil. In particular, knob (1230) is rotatable to engage threads (not shown) of the shaft assembly to translate a trocar actuation rod (1222), which ultimately actuates the anvil as similarly described above with respect to shaft assembly (200) of instrument (10).

Triggers (1240, 1242) function similarly as triggers (140, 150) described above. For instance, a safety trigger (1240) may be first actuated by an operator to unblock a firing trigger (1242), to thereby enable activation of the stapling head assembly. Although not shown, it should be understood that like with safety trigger (140) described above, safety trigger (1240) may include an upright member (not shown) that is generally operable to permit actuation of safety trigger (1240) only after the anvil has been adjusted to define a gap distance (d) that is within a clinically acceptable range. Additionally, it should be understood that firing trigger (1242) may also include an upright member (not shown) similar to second upright member (154) described above. Of course, in other examples the upright members may be omitted entirely.

Firing trigger (1242) is similar to firing trigger (150) described above. In particular, once safety trigger (1240) has been activated, firing trigger (1242) is operable to initiate actuation of the stapling head assembly. Firing trigger (1242) includes a paddle (1246), which is configured to engage a motor activation module (not shown) when firing trigger (1242) is advanced by an operator. Like with motor activation module (180) described above, the motor activation module of the present example initiates the stapling sequence by activating a motor (not shown). The motor then drives a cam member (1252), which in turn drives a cam follower (1254). Cam member (1252) and cam follower (1254) are substantially the same as cam member (700) and cam follower (600) described above, such that cam member (1252) and cam follower (1254) cooperate to drive the stapling head assembly through a stapling sequence.

Unlike instrument (10) described above, instrument (1200) of the present example comprises an anvil lockout assembly (1270). Anvil lockout assembly (1270) is generally configured to prevent further adjustment of the longitudinal position of the anvil once safety trigger (1240) is actuated. Such a feature may be desirable because lockout of the anvil may prevent an operator from improperly changing the gap distance (d) once a suitable gap distance (d) is reached. Anvil lockout assembly (1270) comprises an actuation member (1272), a pivot (1274), a resilient member (1276) and a lockout member (1280). Actuation member (1272) is configured to engage with a lockout arm (1241) that is attached to safety trigger (1240). As will be described in greater detail below, actuation member (1272) is generally configured to hold anvil lockout assembly (1270) in the position shown in FIGS. 33 and 36 until safety trigger (1240) is actuated.

Resilient member (1276) and actuation member (1272) are disposed on opposite sides of pivot (1274). Pivot (1274) permits actuation member (1272), resilient member (1276) and lockout member (1280) to pivot about an axis defined by pivot (1274). Resilient member (1276) is configured to drive actuation member (1272) and lockout member (1280) in a counter clockwise direction (as seen in FIG. 33) once actuation member (1272) is disengaged from lockout arm (1241) of safety trigger (1240). As will be understood, resilient member (1276) is generally configured to bias anvil lockout assembly (1270) toward a locked position.

Lockout member (1280) extends upwardly from pivot (1274) through a longitudinal slot (1223) in trocar actuation rod (1222). As can be seen, lockout member (1280) is generally positioned perpendicularly relative to the longitudinal axis of trocar actuation rod (1222). Lockout member (1280) includes two blocks (1282) disposed on either side of trocar actuation rod (1222). Blocks (1282) are positioned on lockout member (1280) at a distance that is slightly larger than the outer diameter of trocar actuation rod (1222). As will be described in greater detail below, such a positioning of blocks (1282) enables lockout member (1280) to prevent translation of trocar actuation rod (1222) in at least one direction when lockout member (1280) departs from the perpendicular positioning shown in FIG. 33.

Figure 34:
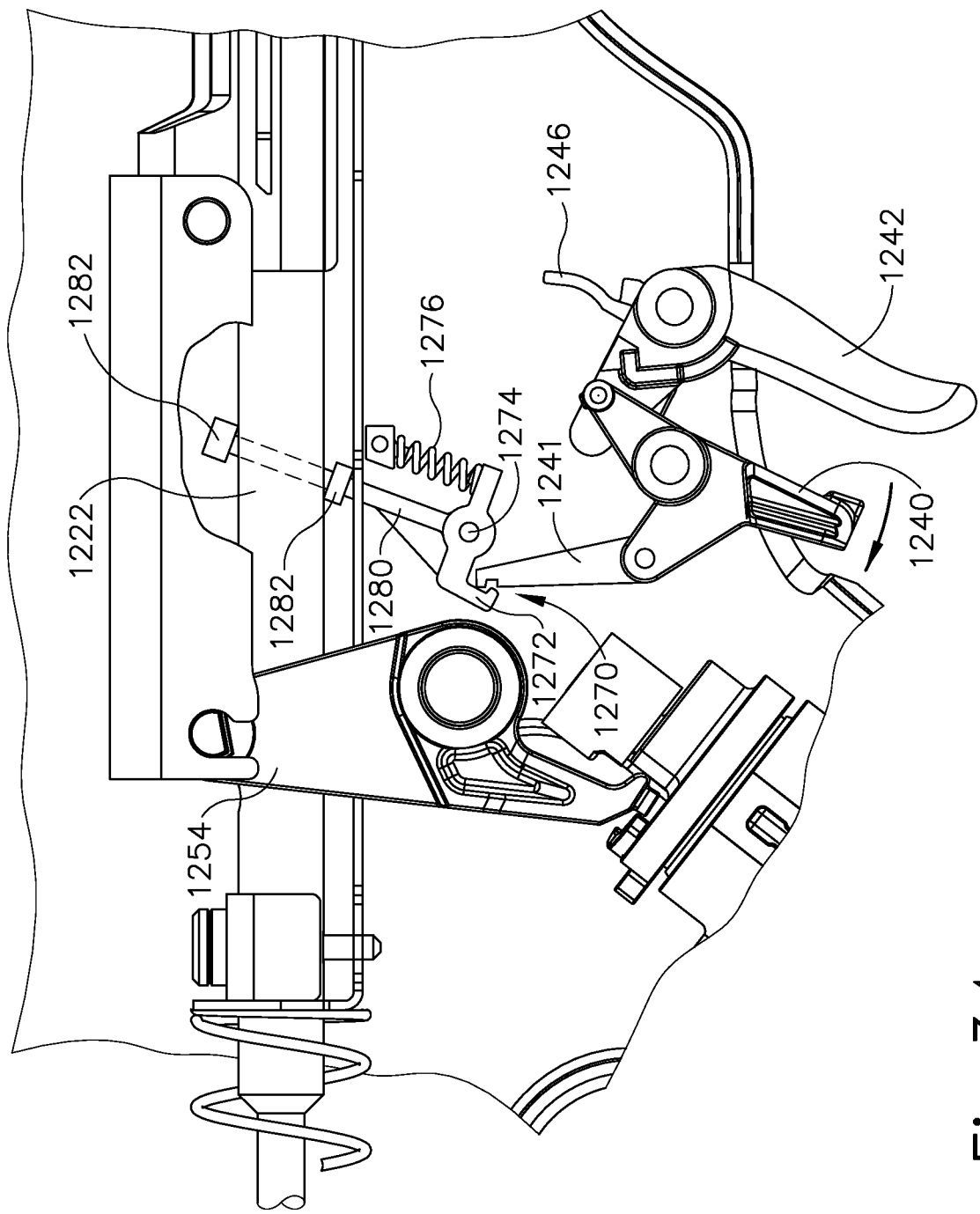
FIG. 34 depicts a detailed side elevational view of the anvil lockout assembly of FIG. 33, with the anvil lockout assembly in an intermediate state between an unlocked position and a locked position.
Figure 35:
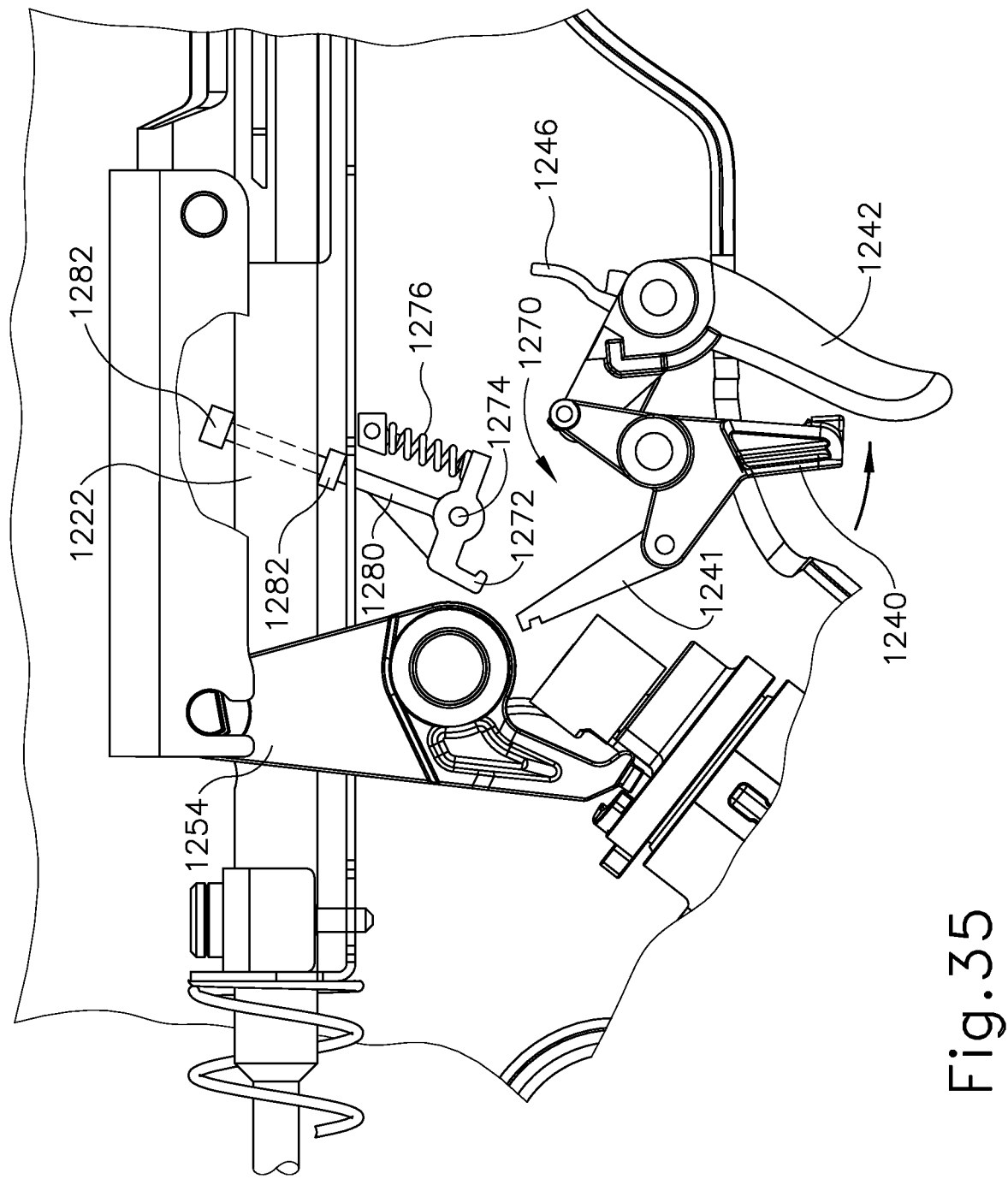
FIG. 35 depicts another detailed side elevational view of the anvil lockout assembly of FIG. 33, with the anvil lockout assembly in the locked position.
Figure 36:
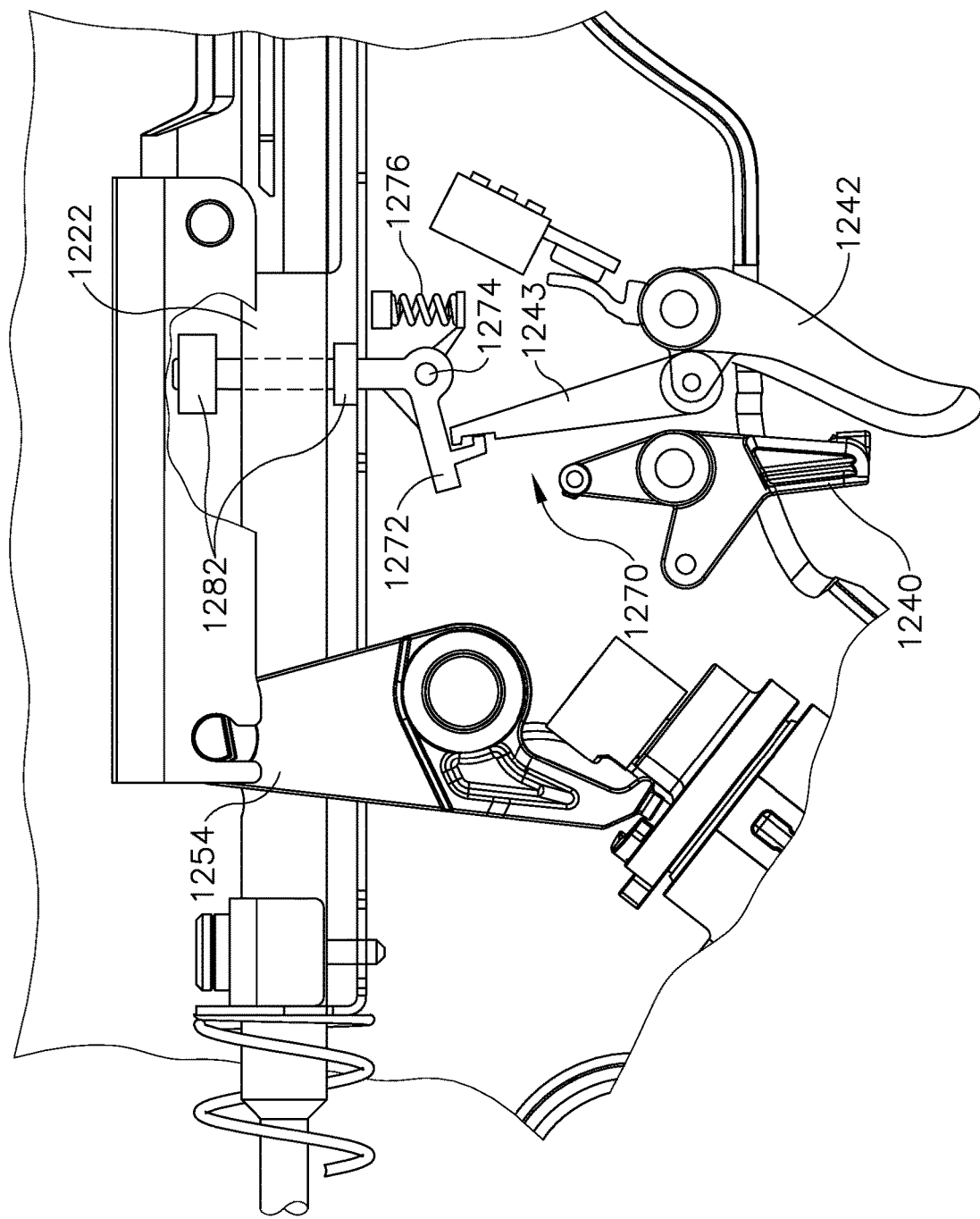
FIG. 36 depicts a detailed side elevational view of an exemplary variation of the anvil lockout assembly of FIG. 33, with the anvil lockout assembly in an unlocked position.

FIGS. 33-36 show an exemplary sequence of operation of anvil lockout assembly (1270). It should be noted that FIG. 33 shows instrument (1200) oriented with the distal end toward the left side of the page, while FIGS. 34-36 show instrument (1200) oriented with the distal end toward the right side of the page. As can be seen in FIG. 33, anvil lockout assembly (1270) is initially in an unlocked position, where trocar actuation rod (1222) is freely translatable within handle assembly (1210). In this position, actuation member (1272) is in engagement with safety trigger (1240), thereby holding anvil lockout assembly (1270) in the unlocked position. Correspondingly, lockout member (1280) is disposed in a position that is perpendicular to the longitudinal axis of trocar actuation rod (1222) such that translation of trocar actuation rod (1222) is not impeded by blocks (1282).

To shift anvil lockout assembly (1270) to the locked position, an operator merely has to actuate safety trigger (1240). Once safety trigger (1240) is actuated, lockout arm (1241) of safety trigger (1240) disengages from actuation member (1272) as shown in FIG. 34. With actuation member (1272) disengaged from lockout arm (1241), resilient member (1276) initiates movement of actuation member (1272) and lockout member (1280) in a clockwise direction (as shown in FIG. 34, but counter clockwise in FIG. 33) about pivot (1274). With lockout member (1280) rotated in a clockwise direction, blocks (1282) bear against the outer diameter of trocar actuation rod (1222), providing friction that prevents further advancement of the anvil via trocar actuation rod (1222).

Once anvil lockout assembly (1270) is in a locked position, lockout assembly (1270) will remain in the locked position. Even if the operator pivots safety trigger (1240) back to a non-actuated position as shown in FIG. 35, this pivotal movement of safety trigger (1240) will have no effect on lockout member (1280) since safety trigger (1240) is completely disengaged from lockout member (1280) as soon as lockout member (1280) pivots to the locking position.

FIG. 36 shows a variation of lockout assembly (1270) where an arm (1243) of firing trigger (1242) is engaged with actuation member (1272). In particular, when firing trigger (1242) is in a non-actuated position as shown in FIG. 36, arm (1243) holds lockout member (1280) in an unlocked state, preventing blocks (1282) from bearing against trocar actuation rod (1222). The operator is thus free to adjust the longitudinal position of the anvil via trocar actuation rod (1222) in the state shown in FIG. 36. However, after the operator pivots safety trigger (1240) to the actuated position, and then pivots firing trigger (1242) to the actuated position, arm (1243) disengages actuation member (1272). This disengagement of arm (1243) from actuation member (1272) allows resilient member (1276) to drive lockout member (1280) about pivot (1274), thereby driving blocks (1282) into trocar actuation rod (1222) to prevent further longitudinal movement of trocar actuation rod (1222). Thus, the variation of FIG. 36 operates substantially identically to the example of FIGS. 33-35 except that firing trigger (1242) releases lockout member (1280) in the variation of FIG. 36 while safety trigger (1240) releases lockout member (1280)

in the example of FIGS. 33-35. Still other suitable variations will be apparent to those of ordinary skill in the art in view of the teachings herein.

B. Exemplary Anvil Lockout Assembly Actuated by Cam Follower

Figure 37:
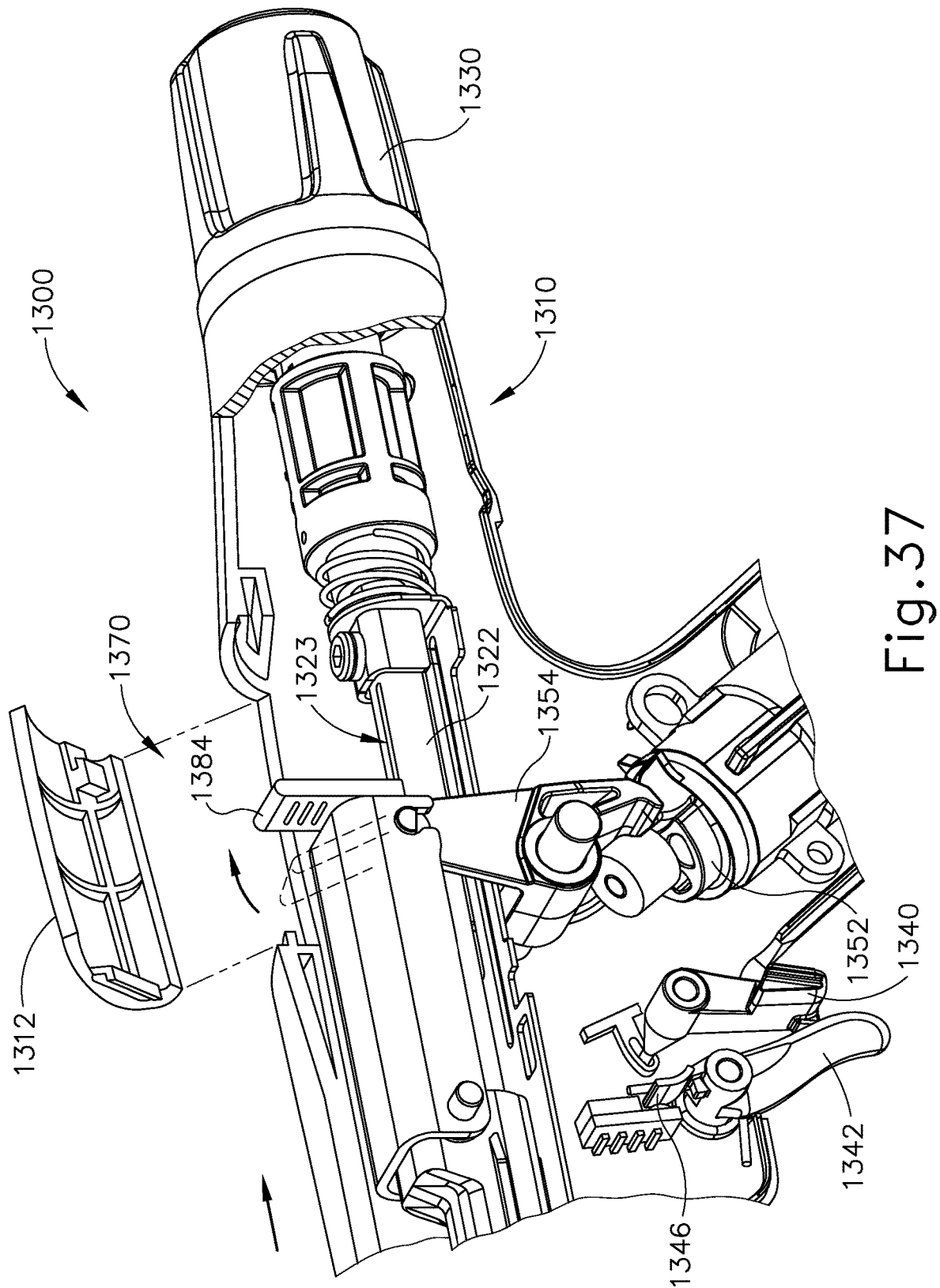
FIG. 37 depicts a detailed perspective cut-away view of yet another exemplary alternative anvil lockout assembly.

FIG. 37 shows yet another exemplary alternative instrument (1300) that may be used to provide an end-to-end anastomosis between two sections of an anatomical lumen such as a portion of a patient's digestive tract. It should be understood that instrument (1300) of the present example is substantially the same as instrument (10) described above unless otherwise noted herein. For instance, like with instrument (10), instrument (1300) comprises a handle assembly (1310), a shaft assembly (not shown), a stapling head assembly (not shown), and an anvil (not shown). Handle assembly (1310) is substantially the same has handle assembly (110) described above such that further details will not be described herein.

Like with instrument (10) described above, instrument (1300) is controlled by an operator via knob (1330) and triggers (1340, 1342). Knob (1330), like with knob (130) described above, is operatively connected to the shaft assembly to actuate the anvil. In particular, knob (1330) is rotatable to engage threads (not shown) of the shaft assembly to translate a trocar actuation rod (1322), which ultimately actuates the anvil as similarly described above with respect to shaft assembly (200) of instrument (10).

Triggers (1340, 1342) function similarly as triggers (140, 150) described above. For instance, a safety trigger (1340) may be first actuated by an operator to unblock a firing trigger (1342), to thereby enable activation of the stapling head assembly. Although not shown, it should be understood that like with safety trigger (140) described above, safety trigger (1340) may include an upright member (not shown) that is generally operable to permit actuation of safety trigger (1340) only after the anvil has been adjusted to a clinically acceptable range. Additionally, it should be understood that firing trigger (1342) may also include an upright member (not shown) similar to second upright member (154) described above. Of course, in other examples the upright members may be omitted entirely.

Firing trigger (1342) is similar to firing trigger (150) described above. In particular, once safety trigger (1340) has been activated, firing trigger (1342) is operable to initiate actuation of the stapling head assembly. Firing trigger (1342) includes a paddle (1346), which is configured to engage a motor activation module (not shown) when firing trigger (1342) is advanced by an operator. Like with motor activation module (180) described above, the motor activation module of the present example initiates the stapling sequence by activating a motor (not shown). The motor then drives a cam member (1352), which in turn drives a cam follower (1354). Cam member (1352) and cam follower (1354) are substantially the same as cam member (700) and cam follower (600) described above, such that cam member (1352) and cam follower (1354) cooperate to drive the stapling head assembly through a stapling sequence.

Figure 38:
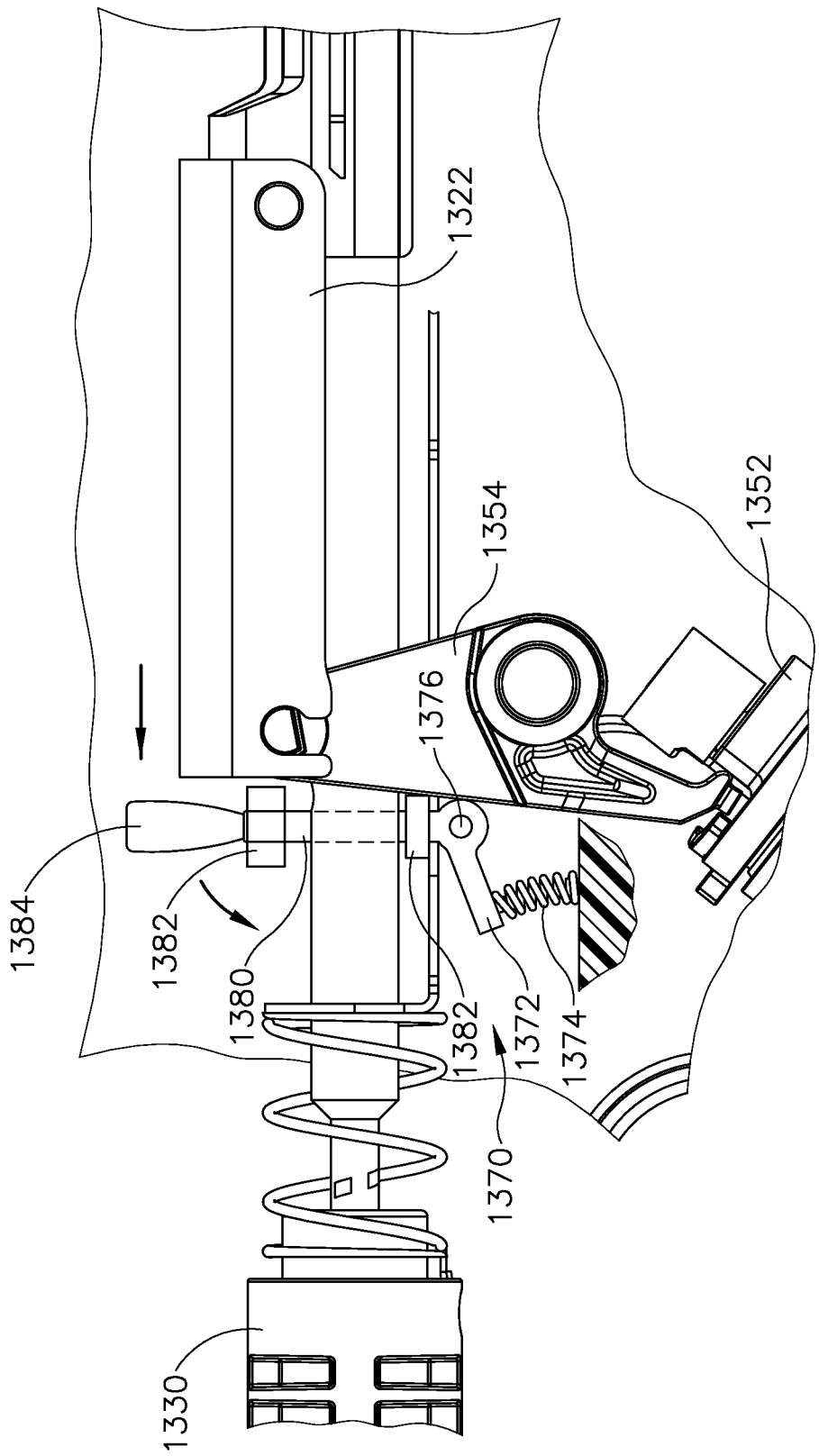
FIG. 38 depicts a detailed side elevational view of the anvil lockout assembly of FIG. 37, with the anvil lockout assembly in an unlocked position.

Unlike instrument (10) described above, instrument (1300) of the present example comprises an anvil lockout assembly (1370). Anvil lockout assembly (1370) is generally configured to prevent further adjustment of the longitudinal position of the anvil once safety trigger (1340) is activated. Such a feature may be desirable because lockout of the anvil may prevent an operator from improperly changing the gap distance (d) once a suitable gap distance (d) is reached. As can be seen in FIGS. 37-38, anvil lockout assembly (1370) comprises a lever arm (1372), a pivot (1376), a resilient member (1374), and a lockout member (1380). Lever arm (1372) is pivotable about pivot (1376) to actuate lockout member (1380) between an unlocked and locked position, as will be described in greater detail below. Resilient member (1374) is in communication with lever arm (1372) and is configured to bias anvil lockout assembly (1370) toward a locked position.

Lockout member (1380) extends upwardly from pivot (1376) through a slot (1323) in trocar actuation rod (1322). Lockout member (1380) comprises a pair of blocks (1382) and a tab (1384). Each block (1382) is disposed on either side of trocar actuation rod (1322). Blocks (1382) are spaced from each other at a distance that is slightly larger than the outer diameter of trocar actuation rod (1322). As will be described in greater detail below, such a spacing of blocks (1382) is configured to permit actuation of trocar actuation rod (1322) when lockout member (1380) is positioned perpendicularly relative to the longitudinal axis of trocar actuation rod (1322); yet blocks (1382) are also configured to lock trocar actuation rod (1322) when lockout member (1380) is positioned at a non-perpendicular angle relative to the longitudinal axis of trocar actuation rod (1322).

Tab (1384) of lockout member (1380) extends upwardly into handle assembly (1310) from the upper end of lockout member (1380). As will be described in greater detail below, tab (1384) is accessible to an operator by removing a panel (1312) of handle assembly (1310) to expose the internal components of instrument (1300). As will also be described in greater detail below, tab (1384) is generally configured to act as a bailout feature, permitting an operator to manually disengage anvil lockout assembly (1370) when anvil lockout assembly (1370) is in a locked position.

Figure 39:
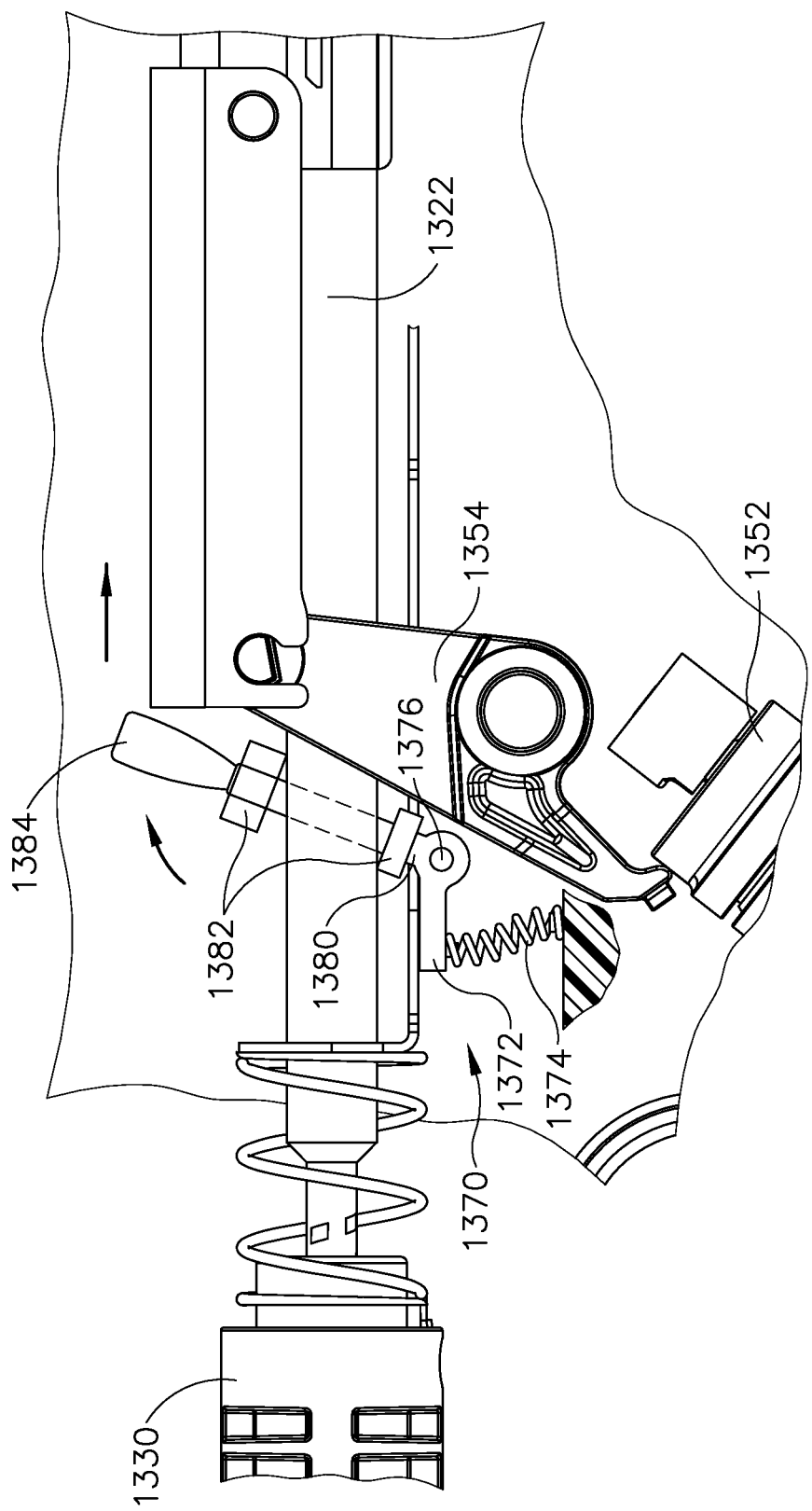
FIG. 39 depicts another detailed side elevational view of the anvil lockout assembly of FIG. 37, with the anvil lockout assembly in a locked position.

FIGS. 38-39 show an exemplary sequence of operation of anvil lockout assembly (1370). As can be seen in FIG. 38, anvil lockout assembly (1370) may initially be unlocked by cam follower (1354) acting on lockout member (1380) against the biasing of resilient member (1374) to align lockout member (1380) in a perpendicular position relative to the longitudinal axis of trocar actuation rod (1322). Thus, it should be understood that unlike other anvil lockout assemblies (1070, 1170, 1270) described above that are controlled by respective safety triggers (1040, 1140, 1240), anvil lockout assembly (1370) of the present example is controlled by the positioning of cam follower (1354).

As can be seen in FIG. 39, as cam follower (1354) is actuated by cam member (1352) during the staple firing sequence, lockout member (1380) is permitted to move to a locked position. In particular, pivotal movement of cam follower (1354) provides clearance for lockout member (1380) to rotate about pivot (1376). With such clearance available, resilient member (1374) acts upon lever arm (1372), driving lever arm (1372) and lockout member (1380) in a clockwise direction. Such movement of lockout member (1380) permits blocks (1382) to bear against the outer diameter of trocar actuation rod (1322), thereby preventing further actuation of trocar actuation rod (1322). It should therefore be understood that the longitudinal position of the anvil will be locked by blocks (1382) as soon as cam follower (1354) as part of the staple firing sequence. As noted above, cam follower (1354) will eventually pivot back from the position shown in FIG. 39 to the position shown in FIG. 38 as the staple firing sequence is fully completed. It should be understood that cam follower (1354) will thus drive lockout member (1380) back to the unlocked position as the staple firing sequence is fully completed. The operator may then translate the anvil distally to assist in releasing tissue to facilitate removal of instrument (1300) from the patient.

In some instances, it may be desirable to bail out of a staple firing sequence before that sequence is completed. In particular, it may be desirable to translate the anvil distally to assist in releasing tissue before cam follower (1354) pivots back to the position shown in FIG. 38. This may occur where, for example, operator error prevents instrument (1300) from being able to complete the full staple firing sequence. To return anvil lockout assembly (1370) to the unlocked position without moving cam follower (1354), the operator may remove panel (1312) of handle assembly (1310) as shown in FIG. 37. With panel (1312) removed, the operator may grasp tab (1384) of lockout member (1380). To unlock lockout member (1380) the operator may pull tab (1384) proximally as shown in FIG. 37. This proximal movement of tab (1384) will disengage blocks (1382) from trocar actuation rod (1322), thereby permitting the operator to actuate trocar actuation rod (1322) to drive the anvil distally to release tissue. Although instrument (1300) is described herein as providing a bailout feature via tab (1384), it should be understood that such a feature is merely optional and may be omitted in some examples.

C. Exemplary Alternative Triggers with Safety Return Feature

Figure 40:
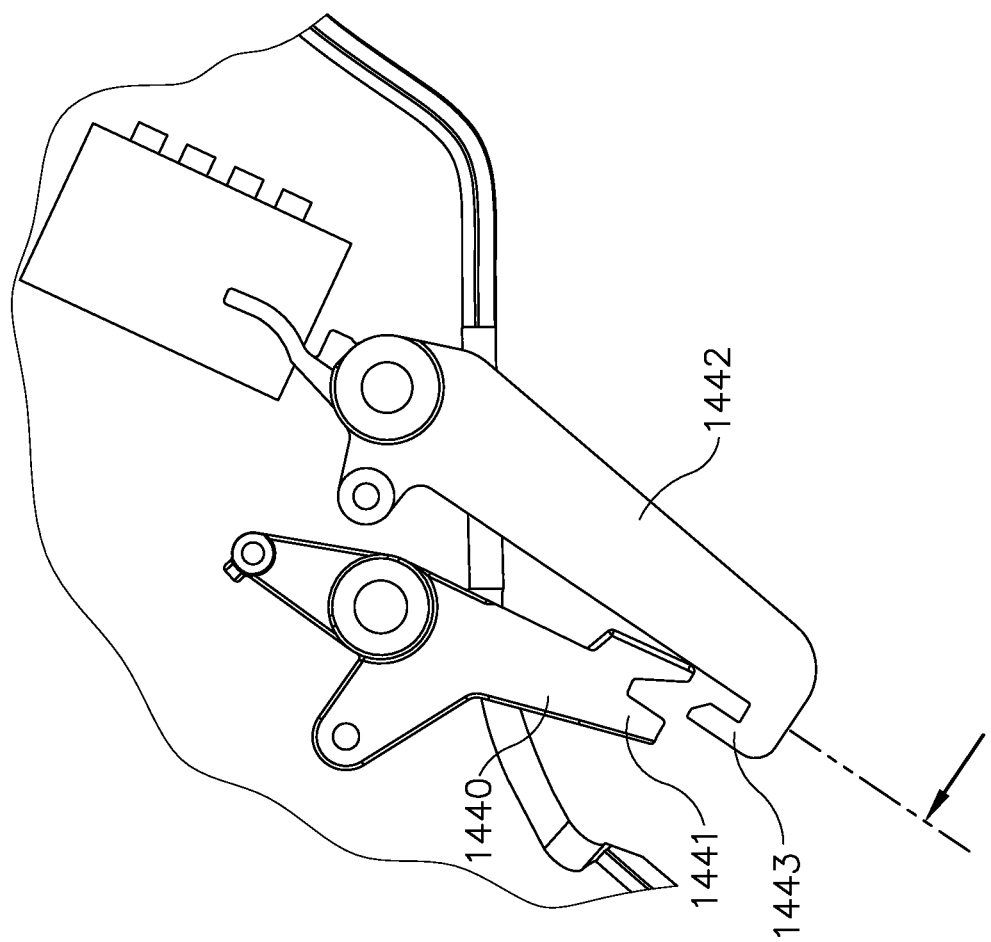
FIG. 40 depicts a side elevational view of an exemplary alternative set of triggers that may be readily incorporated into the circular staplers of FIGS. 1, 22, 27, 33 and 37.

FIG. 40 shows an exemplary set of triggers (1440, 1442) that may be readily incorporated into any of the instruments (10, 1000, 1100, 1200, 1300) described above. Generally, triggers (1440, 1442) are usable to operate instruments (10, 1000, 1100, 1200, 1300) substantially the same as described above. However, unlike other triggers (140, 150, 1040, 1042, 1140, 1142, 1240, 1242, 1340, 1342), triggers (1440, 1442) include other functional features that may improve the general operability of instruments (10, 1000, 1100, 1200, 1300). In particular, triggers (1440, 1442) comprise a safety trigger (1440) and a firing trigger (1442). Generally, firing trigger (1442) is operable to automatically retract safety trigger (1440) to its initial position when firing trigger (1442) returns to its initial position after being actuated.

As can be seen, safety trigger (1440) includes a receiving feature (1441) that is configured to receive at least a portion of firing trigger (1442). Correspondingly, firing trigger (1442) includes a coupling feature (1443) that is configured to be received in receiving feature (1441). As will be described in greater detail below, coupling feature (1443) generally defines a hook shape such that coupling feature (1443) may pull safety trigger (1440) to its initial position.

FIGS. 40-43 show an exemplary sequence of operation of triggers (1440, 1442). As can be seen in FIG. 40, initially triggers (1440, 1442) are disposed in an initial position. It should be understood that the initial position corresponds to the position of triggers (1440, 1442) prior to use by an operator to initiate a stapling sequence. In the initial position, receiving feature (1441) of safety trigger (1440) and coupling feature (1443) of firing trigger (1442) are disengaged from each other such that safety trigger (1440) may move independently relative to firing trigger (1442).

Figure 41:
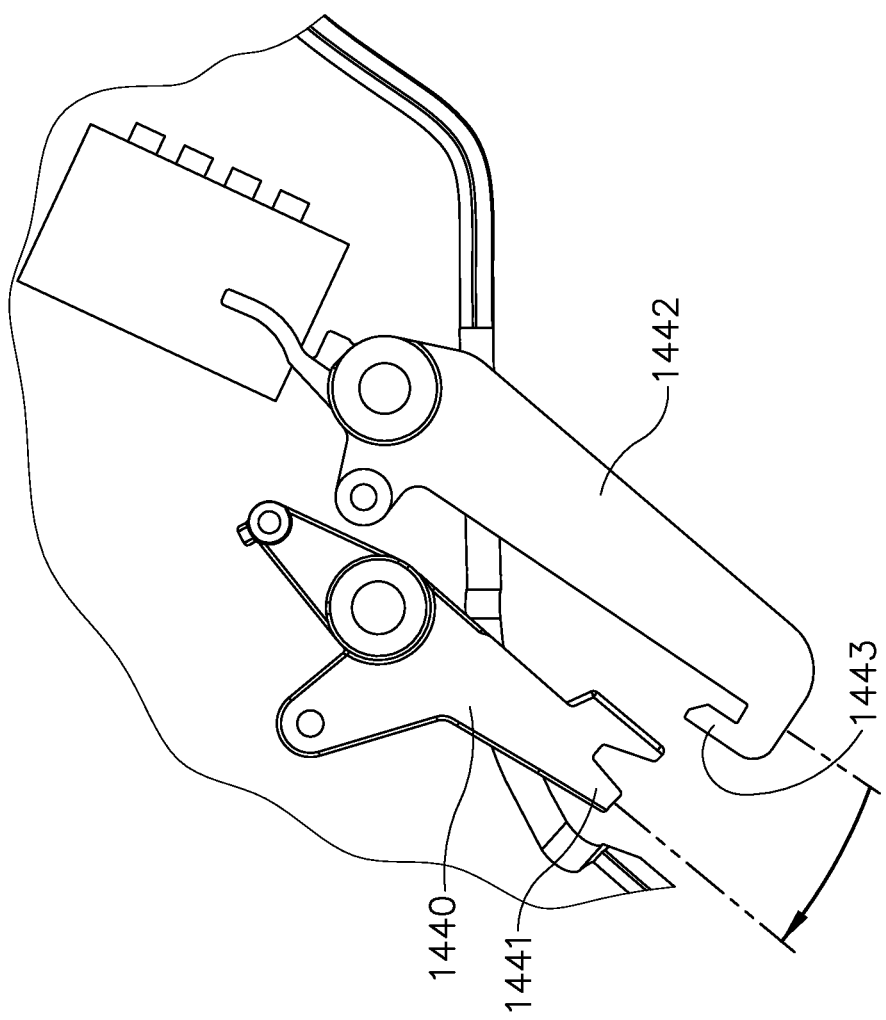
FIG. 41 depicts another side elevational view of the triggers of FIG. 40, with a safety trigger engaged.

As described above with respect to instrument (10), to initiate a stapling sequence, an operator must first actuate safety trigger (1440) to unlock movement of firing trigger (1442). FIG. 41 shows safety trigger (1440) in an actuated position such that firing trigger (1442) is in an unlocked condition where the operator may actuate firing trigger (1442). As can be seen, in this stage receiving feature (1441) of safety trigger (1440) and coupling feature (1443) of firing trigger (1442) remain disengaged from each other and are now offset from each other.

Figure 42:
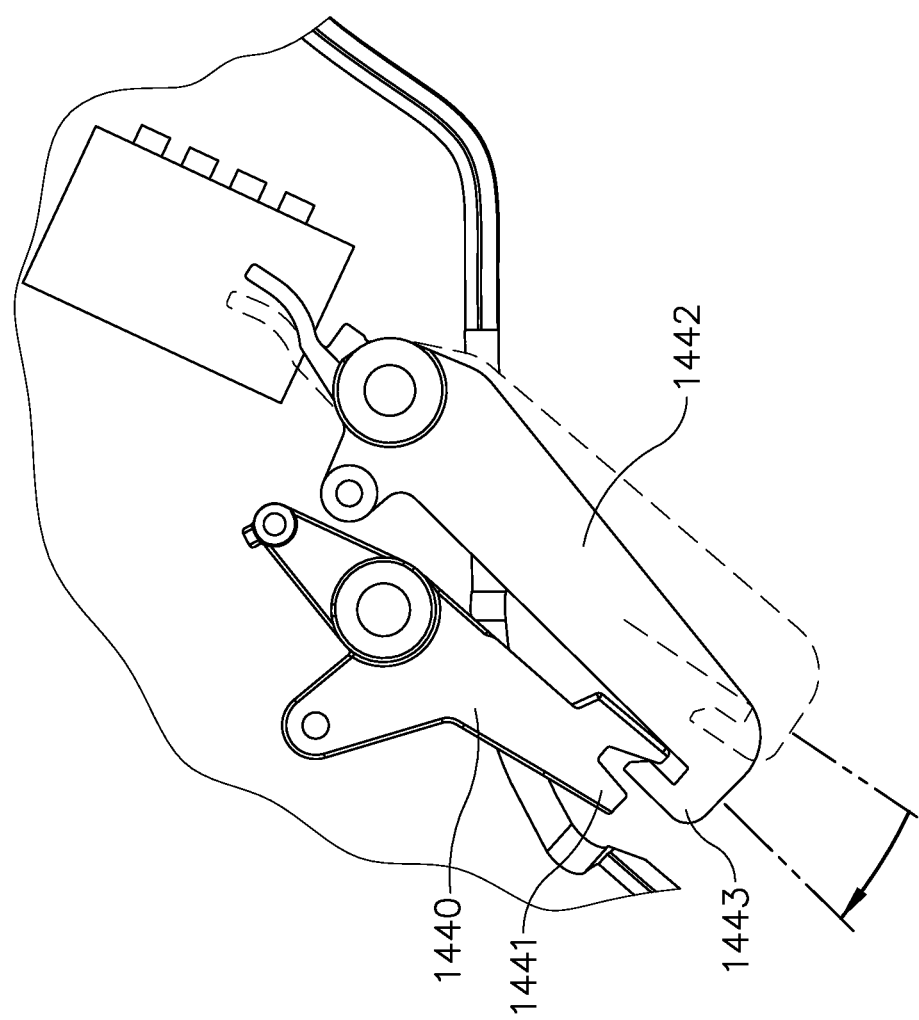
FIG. 42 depicts another side elevational view of the triggers of FIG. 40, with a firing trigger advanced to an activation position and engaged with the safety trigger.

Next, the operator may desire to initiate a stapling sequence by actuating firing trigger (1442) to a firing position. FIG. 42 shows firing trigger (1442) actuated to a position where a firing sequence is initiated. As can be seen by comparing FIGS. 41 and 42, in the process of actuating firing trigger (1442), coupling feature (1443) of firing trigger (1442) enters into receiving feature (1441) of safety trigger (1440) thereby interlocking firing trigger (1442) and safety trigger (1440).

Figure 43:
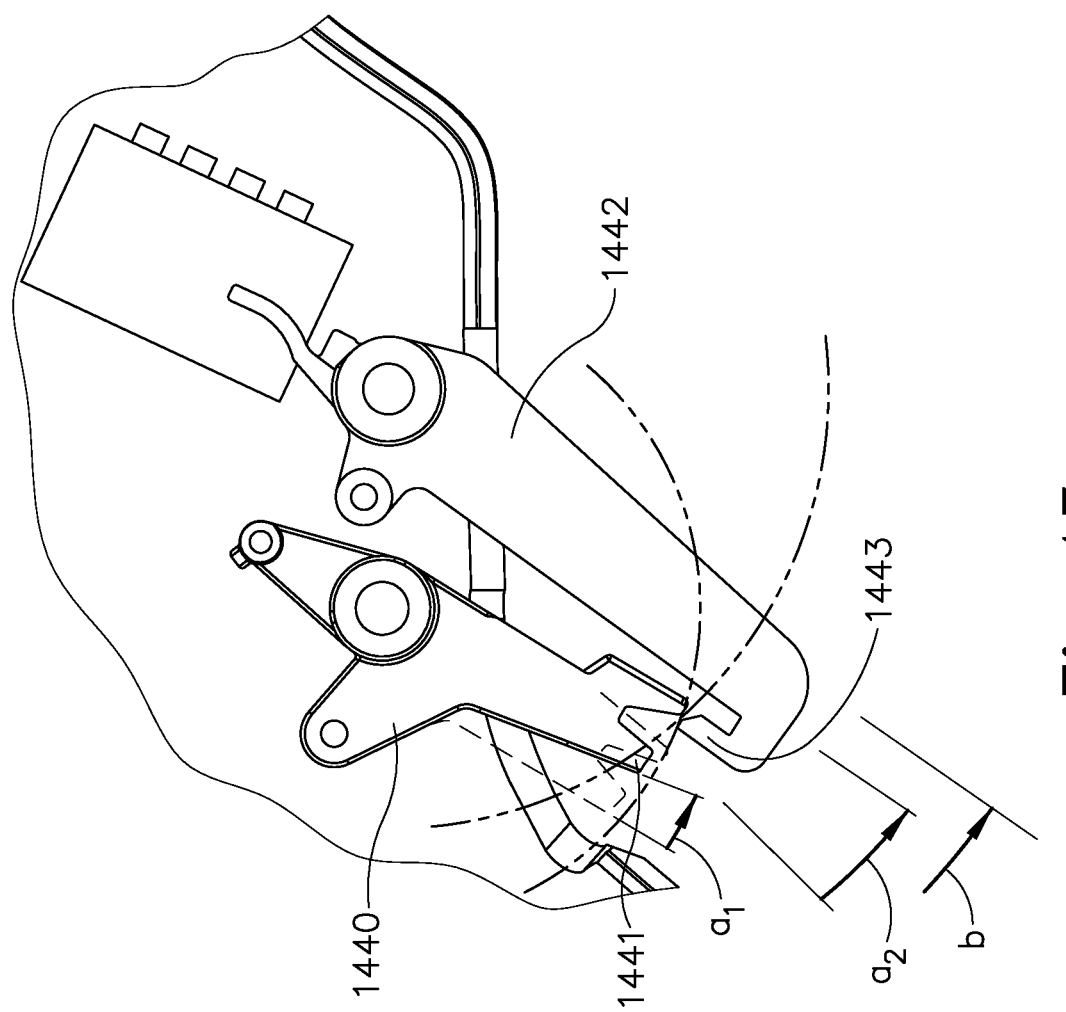
FIG. 43 depicts still another side elevational view of the triggers of FIG. 40, with the firing trigger returning the safety trigger to an initial position.

Once firing trigger (1442) has been actuated to the firing position, the interlocking relationship of coupling feature (1443) and receiving feature (1441) will permit firing trigger (1442) to automatically return safety trigger (1440) toward the initial position of safety trigger (1440). As can be seen in FIG. 43, firing trigger (1442) moves through a return stroke ($a_1$) pulling safety trigger (1440) through a separate safety return stroke ($a_2$). It should be understood that the respective travel paths (shown in phantom in FIG. 43) of safety trigger (1440) and firing trigger (1442) are configured such that coupling feature (1443) remains received within receiving feature (1441) only for the duration of safety return stroke ($a_2$) to pull safety trigger (1440) to its initial position. Once coupling feature (1443) disengages from receiving feature (1441), firing trigger (1442) may continue moving through return stroke ($a_1$), through a travel stroke (b) before returning to the initial position of firing trigger (1442). Although not shown, it should be understood that in some examples firing trigger (1442) may include a resilient feature that may return firing trigger (1442) to the initial position of firing trigger (1442) automatically after an operator releases firing trigger (1442). Of course, such a feature is merely optional and may be omitted in some examples.

D. Exemplary Triggers with Secondary Firing Lockout Feature

Figure 44:
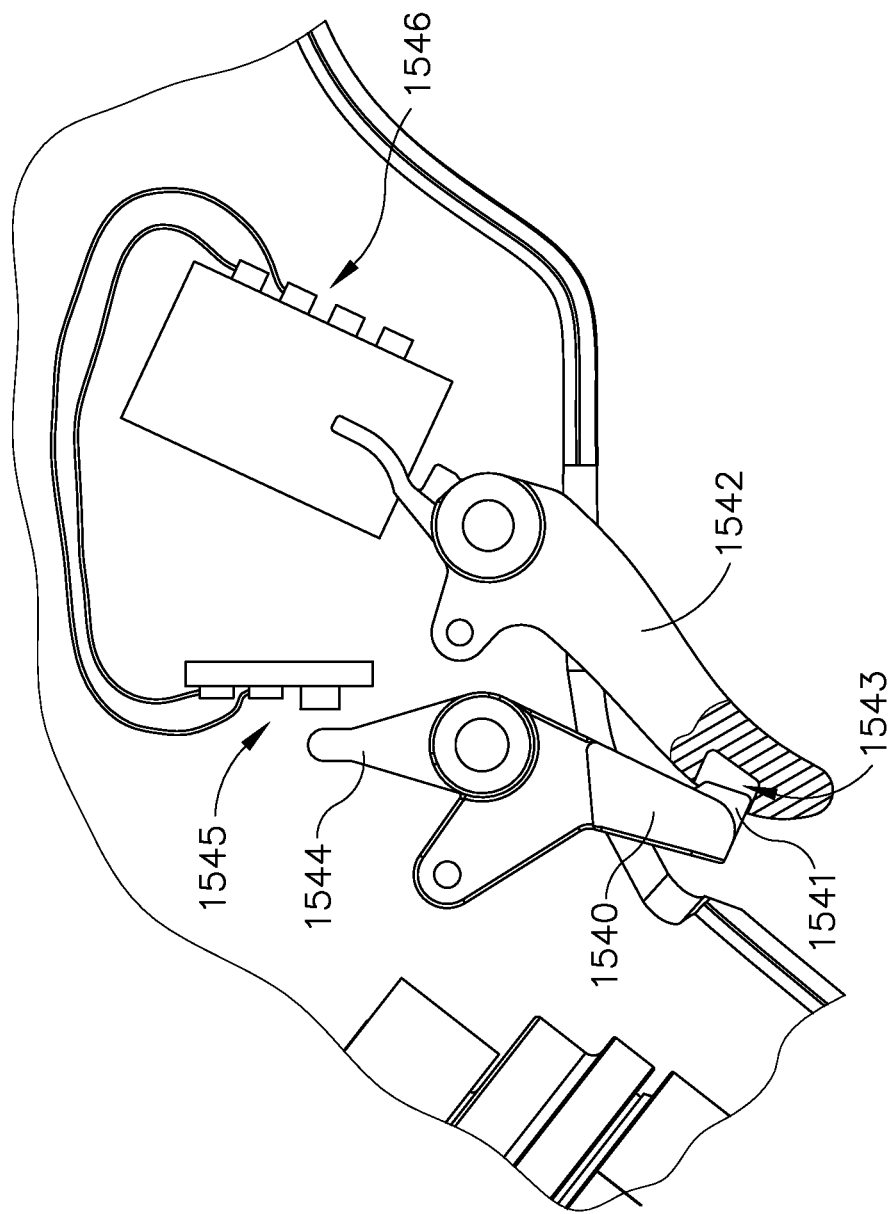
FIG. 44 depicts a side elevational view of another exemplary alternative set of triggers that may be readily incorporated into the circular staplers of FIGS. 1, 22, 27, 33, and 37.

FIG. 44 shows another exemplary set of triggers (1540, 1542) that may be readily incorporated into any of the instruments (10, 1000, 1100, 1200, 1300) described above. Generally, triggers (1540, 1542) are usable to operate instruments (10, 1000, 1100, 1200, 1300) substantially the same as described above. However, unlike other triggers (140, 150, 1040, 1042, 1140, 1142, 1240, 1242, 1340, 1342), triggers (1540, 1542) include other functional features that may improve the general operability of instruments (10, 1000, 1100, 1200, 1300). In particular, triggers (1540, 1542) comprise a safety trigger (1540) and a firing trigger (1542). Safety trigger (1540) is substantially the same as safety trigger (140) described above, except safety trigger (1540) is generally configured to provide both a mechanical stop to firing trigger (1542) and a digital or electrical stop to firing trigger (1542).

As can be seen, safety trigger (1540) includes a stop protrusion (1541) and an actuator (1544). Protrusion (1541) is configured to be received within a corresponding recess (1543) disposed within firing trigger (1542). When protrusion (1541) is received within recess (1543), protrusion prevents actuation of firing trigger (1542) because protrusion (1543) blocks the travel path of firing trigger (1542).

Safety trigger (1540) also includes actuator (1544). Generally actuator (1544) interfaces with a button assembly (1545) to provide a second lockout feature to prevent staple firing while safety trigger (1540) is engaged. In particular, button assembly (1545) is in communication with a motor activation module (1546) that is substantially the same as motor activation module (180) described above. When actuator (1544) of safety trigger (1540) is not engaged with button assembly (1545), a safety circuit of motor activation module (1546) is left in an open state such that motor activation module (180) is electrically inoperable to activate a motor (not shown). With the safety circuit in the open state, even if the operator were somehow able to actuate firing trigger (1542), motor activation module (1546) would not be able to activate the motor in response to actuation of firing trigger (1542). Thus, in the state shown in FIG. 44, the staple firing sequence is mechanically prevented by the pivotal position of safety trigger (1540) and is electrically prevented by the open circuit provided by button assembly (1545) being disengaged by actuator (1544).

However, once safety trigger (1540) is actuated away from firing trigger (1542), actuator (1544) engages button assembly (1545). Once button assembly (1545) is engaged by actuator (1544) the safety circuit of motor activation module (1546) is in a closed state. With the safety circuit in a closed state, subsequent actuation of firing trigger (1542) will initiate a staple firing sequence.

E. Exemplary Firing Lockout Features

Figure 45:
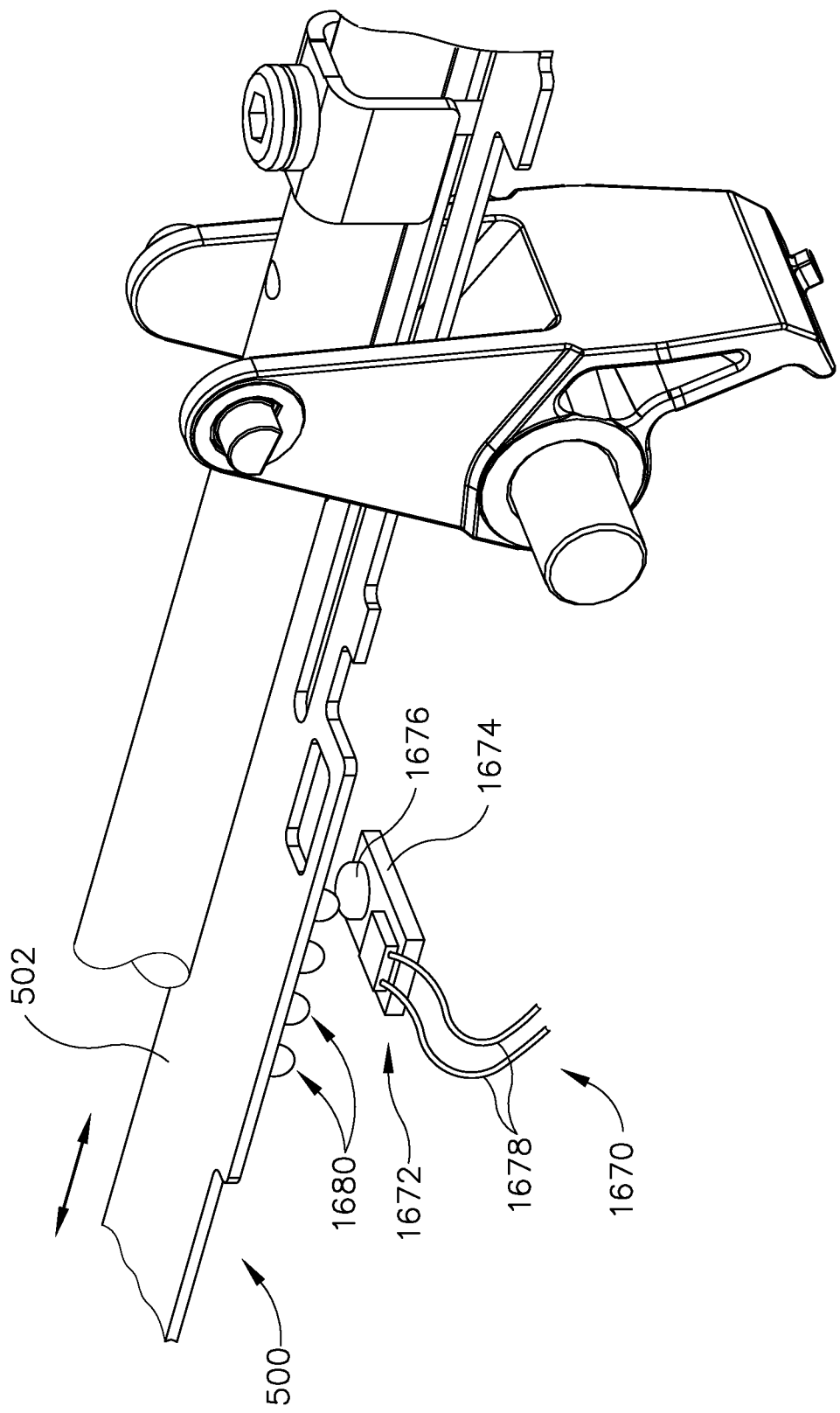
FIG. 45 depicts a detailed perspective view of the anvil actuation assembly of FIG. 12A, with the anvil actuation assembly equipped with a firing lockout assembly.

FIG. 45 shows an exemplary firing lockout assembly (1670) that may be readily incorporated into any of the instruments (10, 1000, 1100, 1200, 1300) described above. Although firing lockout assembly (1670) may be readily incorporated into instruments (10, 1000, 1100, 1200, 1300), firing lockout assembly (1670) is described herein in the context of instrument (10). As described above, instrument (10) includes a first upright member (144) and a second upright member (154) to physically stop triggers (140, 150) from being actuated before anvil (400) is adjusted to a position within a clinically acceptable range. It should be understood that in some examples it may be desirable to provide a separate electronic stop in addition to, or in lieu of upright members (144, 154). Firing lockout assembly (1670) of the present example provides such functionality.

As can be seen, firing lockout assembly (1670) includes a sensor assembly (1672) and a plurality of indicators (1680). Sensor assembly (1672) comprises a circuit board (1674), a sensor (1676), and a plurality of wires (1678). Circuit board (1674) is in communication with sensor (1676) such that sensor (1676) is operable to communicate the presence of indicators (1680) to circuit board (1674). Circuit board (1674) may then communicate signals from sensor (1676) to motor activation module (180) via wires (1678) as will be described in greater detail below.

Indicators (1680) of the present example comprise a plurality of protrusions extending downwardly from body (502) of bracket (500). Correspondingly, sensor (1676) is a push button that is adjacent to indicators (1680) such that each protrusion may actuate the button as body (502) moves relative to sensor (1676). Alternatively, sensor (1676) may comprise a proximity sensor and/or any other suitable kind of sensor (1676) that is responsive to the presence of indicators (1680) adjacent to sensor (1676). Circuit board (1674) is configured to count each actuation of sensor (1676) such that the relative position of body (502) may be calculated as body (502) moves relative to sensor (1676). After circuit board (1674) has calculated a predetermined travel amount for body (502), circuit board (1674) may send a signal via wires (1678) to motor activation module (180) to indicate that motor (160) may be activated using triggers (140, 150). As noted above, the longitudinal positioning of body (502) is associated with the longitudinal positioning of anvil (400). It should therefore be understood that sensor (1676) may be operable to determine whether the gap distance (d) is within the clinically acceptable range. Moreover, feedback from sensor (1676) may be provided to motor activation module (180) such that actuation of firing trigger (150) will only activate motor (160) if feedback from sensor (1676) indicates that the gap distance (d) is within the clinically acceptable range.

Figure 46:
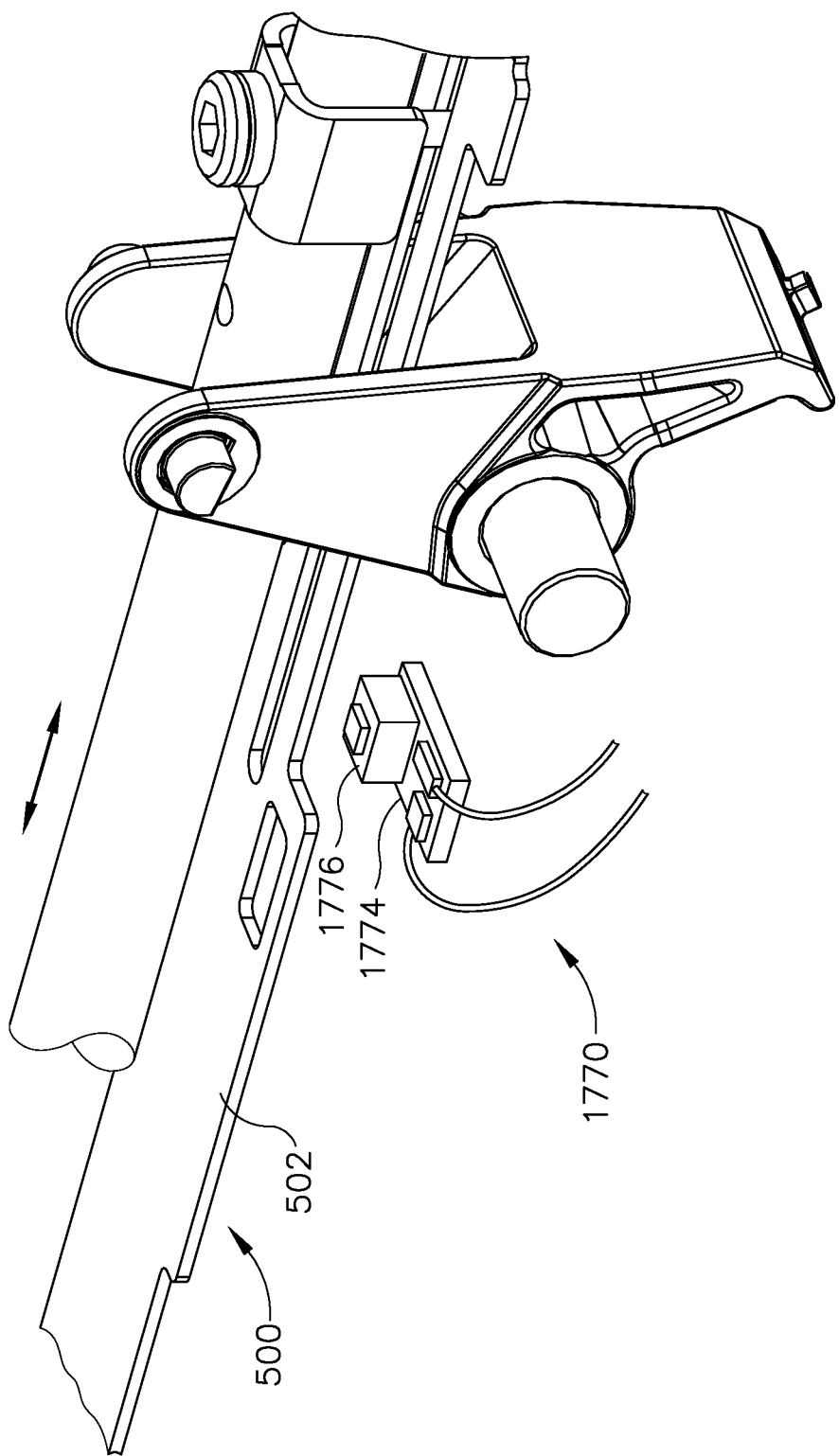
FIG. 46 depicts a detailed perspective view of the anvil actuation assembly of FIG. 12A, with the anvil actuation assembly equipped with an alternative firing lockout assembly.

FIG. 46 shows an exemplary alternative firing lockout assembly (1770). Firing lockout assembly (1770) of this example is substantially the same as firing lockout assembly (1670) described above, except firing lockout assembly (1770) includes a circuit board (1774) equipped with a Hall Effect sensor (1776) instead of a button. Correspondingly, at least a portion of body (502) is magnetized to provide a suitable magnetic field that sensor (1776) may detect. Thus, sensor (1776) may be operable to determine whether the gap distance (d) is within the clinically acceptable range. Moreover, feedback from sensor (1776) may be provided to motor activation module (180) such that actuation of firing trigger (150) will only activate motor (160) if feedback from sensor (1776) indicates that the gap distance (d) is within the clinically acceptable range.

IV. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) a body; (b) a shaft assembly extending distally from the body; (c) a stapling head assembly located at the distal end of the shaft assembly, wherein the stapling head assembly comprises a distal surface, wherein the stapling head assembly is operable to drive an annular array of staples through the distal surface; (d) an anvil, wherein the anvil is configured to couple with the stapling head assembly; (e) an anvil adjustment assembly, wherein the anvil adjustment assembly comprises a translating member, wherein the translating member is operable to translate relative to the body along a longitudinal axis to thereby adjust the longitudinal position of the anvil relative to the distal surface of the stapling head assembly; (f) a first trigger, wherein the first trigger is operable to actuate the stapling head assembly to thereby drive the annular array of staples through the distal surface toward the anvil; and (g) a lockout assembly, wherein the lockout assembly comprises an electrically powered braking feature, wherein the lockout assembly is configured to transition between a first state and a second state, wherein: (i) in the first state, the lockout assembly is configured to permit translation of the translating member, and (ii) in the second state, the lockout assembly is configured to prevent translation of the translating member.

Example 2

The surgical instrument of Example 1, wherein the electrically powered braking feature comprises a solenoid.

Example 3

The surgical instrument of Example 2, wherein the lockout assembly further comprises a second trigger, wherein the second trigger is movable between a non-actuated position and an actuated position, wherein the second trigger is operable to provide the solenoid in a non-activated state in response to the second trigger being in the non-actuated position, wherein the second trigger is further operable to provide the solenoid in an activated state in response to the second trigger being in the actuated position.

Example 4

The surgical instrument of any one or more of Examples 2 through 3, wherein the braking feature further comprises a lock member, wherein the solenoid is operable to selectively drive the lock member into engagement with the translating member to thereby prevent translation of the translating member.

Example 5

The surgical instrument of Example 4, wherein the translating member comprises a laterally presented array of teeth, wherein the lock member comprises an array of teeth, wherein the solenoid is operable to selectively drive the teeth of the lock member into engagement with the teeth of the translating member to thereby prevent translation of the translating member.

Example 6

The surgical instrument of any one or more of Examples 4 through 5, wherein the solenoid is operable to selectively drive the lock member along a path that is transverse to the longitudinal axis to thereby drive the lock member into engagement with the translating member to thereby prevent translation of the translating member.

Example 7

The surgical instrument of any one or more of Examples 4 through 6, wherein the anvil adjustment assembly comprises an annularly arranged array of teeth, wherein the lock member comprises an angularly arranged array of teeth, wherein the solenoid is operable to selectively drive the teeth of the lock member into engagement with the teeth of the anvil adjustment assembly to thereby prevent translation of the translating member.

Example 8

The surgical instrument of Example 7, wherein the anvil adjustment assembly further comprises a rotary member, wherein the translating member is coupled with the rotary member, wherein the rotary member is operable to drive the translating member longitudinally in response to rotation of the rotary member.

Example 9

The surgical instrument of Example 8, wherein the angularly arranged array of teeth are secured to the rotary member such that the teeth of the lock member are operable to prevent rotation of the rotary member to thereby prevent translation of the translating member.

Example 10

The surgical instrument of any one or more of Examples 4 or 7 through 9, wherein the solenoid is operable to selectively drive the lock member along a path that is parallel to the longitudinal axis to thereby drive the lock member into engagement with the translating member to thereby prevent translation of the translating member.

Example 11

The surgical instrument of any one or more of Examples 1 through 10, wherein in the first state, the lockout assembly is further configured to prevent actuation of the first trigger, and wherein in the second state, the lockout assembly is further configured to permit actuation of the first trigger.

Example 12

The surgical instrument of Example 11, wherein the lockout assembly further comprises a second trigger, wherein the second trigger is movable between a non-actuated position and an actuated position, wherein the second trigger is operable to provide the lockout assembly in the first state in response to the second trigger being in the non-actuated position, wherein the second trigger is further operable to provide the lockout assembly in the second state in response to the second trigger being in the actuated position.

Example 13

The surgical instrument of Example 12, wherein the first trigger is movable from an actuated position to a non-actuated position, wherein the first trigger is configured to drive the second trigger from the actuated position toward the non-actuated position in response to the first trigger being driven from the actuated position toward the non-actuated position.

Example 14

The surgical instrument of any one or more of Examples 1 through 13, wherein the lockout assembly is inoperable to transition from the first state to the second state until the anvil is within a predetermined range of distance from the distal surface of the stapling head assembly.

Example 15

The surgical instrument of Example 14, further comprising a blocking member, wherein the anvil adjustment assembly is operable to drive the blocking member based on the position of the anvil relative to the distal surface of the stapling head assembly, wherein the blocking member is configured to selectively block a portion of the lockout assembly to thereby prevent the lockout assembly from transitioning from the first state to the second state.

Example 16

The surgical instrument of any one or more of Examples 1 through 15, further comprising a motor positioned in the body, wherein the motor is operable to actuate the stapling head assembly in response to actuation of the first trigger.

Example 17

The surgical instrument of Example 16, wherein the lockout assembly further comprises a second trigger, wherein the second trigger is movable between a non-actuated position and an actuated position, wherein the second trigger is operable to: (i) provide the lockout assembly in the first state in response to the second trigger being in the non-actuated position, (ii) electrically disable activation of the motor by the first trigger when the second trigger is in the non-actuated position, (iii) provide the lockout assembly in the second state in response to the second trigger being in the actuated position, and (iv) electrically enable activation of the motor by the first trigger when the second trigger is in the actuated position.

Example 18

The surgical instrument of any one or more of Examples 1 through 17, wherein the anvil adjustment assembly further comprises a trocar secured to the translating member, wherein the trocar is configured to protrude distally from the stapling head assembly, wherein the trocar is configured to couple with the anvil.

Example 19

The surgical instrument of any one or more of Examples 1 through 18, wherein the body defines a socket configured to receive a battery pack, wherein the lockout assembly is configured to be in the first state in response to a battery pack being inserted in the socket, wherein the lockout assembly is configured to be in the second state in response to the absence of a battery pack from the socket.

Example 20

A surgical instrument comprising: (a) a stapling head assembly, wherein the stapling head assembly comprises a plurality of staples; (b) a clamping member, wherein the clamping member comprises a plurality of staple forming features; (c) a clamping drive assembly, wherein the clamping drive assembly is operable to drive the clamping member toward and away from the stapling head assembly; (d) a firing assembly, wherein the firing assembly is operable to actuate the stapling head assembly to thereby drive the staples toward the staple forming features; and (e) a lockout assembly, wherein the lockout assembly is operable to selectively lock the clamping drive assembly and thereby prevent actuation of the clamping drive assembly in response to a first operational condition, wherein the lockout assembly is further operable to selectively lock the clamping drive assembly and thereby prevent actuation of the clamping drive assembly in response to a second operational condition, wherein the second operational condition is different from the first operational condition.

Example 21

The surgical instrument of Example 20, wherein the firing assembly comprises a first trigger, wherein the first condition comprises actuation of the first trigger such that the lockout assembly is operable to selectively lock the clamping drive assembly and thereby prevent actuation of the clamping drive assembly in response to actuation of the first trigger.

Example 22

The surgical instrument of Example 21, wherein the firing assembly further comprises a second trigger, wherein the second trigger is configured to activate the firing assembly to thereby actuate the stapling head assembly to thereby drive the staples toward the staple forming features, wherein the first trigger is configured to selectively prevent actuation of the second trigger.

Example 23

The surgical instrument of any one or more of Examples 20 through 21, further comprising a power source coupling feature, wherein the power source coupling feature is configured to couple with a power source to thereby provide electrical power to the firing assembly, wherein the second condition comprises the absence of a power source from the power source coupling feature such that the lockout assembly is operable to selectively lock the clamping drive assembly and thereby prevent actuation of the clamping drive assembly in response to the absence of a power source from the power source coupling feature.

Example 24

The surgical instrument of Example 23, wherein the power source coupling feature comprises a socket.

Example 25

The surgical instrument of any one or more of Examples 23 through 24, wherein the power source coupling feature is configured to couple with a battery pack.

Example 26

A surgical instrument comprising: (a) a stapling head assembly, wherein the stapling head assembly comprises a plurality of staples; (b) a clamping member, wherein the clamping member comprises a plurality of staple forming features; (c) a clamping drive assembly, wherein the clamping drive assembly is operable to drive the clamping member toward and away from the stapling head assembly; (d) a firing assembly, wherein the firing assembly is operable to actuate the stapling head assembly to thereby drive the staples toward the staple forming features; (e) a first lockout assembly, wherein the first lockout assembly is configured to prevent actuation of the firing assembly unless the clamping member is within a predefined range of distance from the stapling head assembly; and (f) a second lockout assembly, wherein the second lockout assembly is configured to prevent actuation of the clamping drive assembly during activation of the firing assembly, wherein the second lockout assembly comprises an electrically activated actuator

Example 27

A surgical instrument comprising: (a) a body; (b) a shaft assembly extending distally from the body; (c) a stapling head assembly located at the distal end of the shaft assembly, wherein the stapling head assembly comprises a distal surface, wherein the stapling head assembly is operable to drive an annular array of staples through the distal surface; (d) an anvil, wherein the anvil is configured to couple with the stapling head assembly; (e) an anvil adjustment assembly, wherein the anvil adjustment assembly comprises a translating member, wherein the translating member is operable to translate relative to the body along a longitudinal axis to thereby adjust the longitudinal position of the anvil relative to the distal surface of the stapling head assembly; (f) a first trigger, wherein the first trigger is operable to actuate the stapling head assembly to thereby drive the annular array of staples through the distal surface toward the anvil; and (g) a lockout assembly, wherein the lockout assembly comprises: (i) a second trigger, wherein the second trigger is operable to selectively prevent actuation of the first trigger when the second trigger is in a non-actuated state, (ii) a solenoid, and (iii) a braking feature, wherein the solenoid is operable to selectively drive the braking feature along a path transverse to the longitudinal axis into engagement with the translating member of the anvil adjustment assembly in response to actuation of the second trigger, wherein the braking feature is configured to prevent translation of the translating member when the braking feature is engaged with the translating member.

Example 28

A surgical instrument comprising: (a) a body; (b) a shaft assembly extending distally from the body; (c) a stapling head assembly located at the distal end of the shaft assembly, wherein the stapling head assembly comprises a distal surface, wherein the stapling head assembly is operable to drive an annular array of staples through the distal surface; (d) an anvil, wherein the anvil is configured to couple with the stapling head assembly; (e) an anvil adjustment assembly, wherein the anvil adjustment assembly comprises a translating member, wherein the translating member is operable to translate relative to the body along a longitudinal axis to thereby adjust the longitudinal position of the anvil relative to the distal surface of the stapling head assembly; (f) a first trigger, wherein the first trigger is operable to actuate the stapling head assembly to thereby drive the annular array of staples through the distal surface toward the anvil; and (g) a lockout assembly, wherein the lockout assembly comprises: (i) a second trigger, wherein the second trigger is operable to selectively prevent actuation of the first trigger when the second trigger is in a non-actuated state, (ii) a solenoid, and (iii) a braking feature, wherein the solenoid is operable to selectively drive the braking feature along a path parallel to the longitudinal axis into engagement with the translating member of the anvil adjustment assembly in response to actuation of the second trigger, wherein the braking feature is configured to prevent translation of the translating member when the braking feature is engaged with the translating member.

V. Miscellaneous

It should also be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

At least some of the teachings herein may be readily combined with one or more teachings of U.S. Pat. No. 7,794,475, entitled "Surgical Staples Having Compressible or Crushable Members for Securing Tissue Therein and Stapling Instruments for Deploying the Same," issued Sep. 14, 2010, the disclosure of which is incorporated by reference herein; U.S. Pub. No. 2014/0151429, entitled "Trans-Oral Circular Anvil Introduction System with Dilation Feature," published Jun. 5, 2014, issued as U.S. Pat. No. 9,572,573 on Feb. 21, 2017, the disclosure of which is incorporated by reference herein; U.S. Pub. No. 2014/0144968, entitled "Surgical Staple with Integral Pledget for Tip Deflection," published May 29, 2014, issued as U.S. Pat. No. 9,289,207 on Mar. 22, 2016, the disclosure of which is incorporated by reference herein; U.S. Pub. No. 2014/0158747, entitled "Surgical Stapler with Varying Staple Widths along Different Circumferences," published Jun. 12, 2014, now abandoned, the disclosure of which is incorporated by reference herein; U.S. Pub. No. 2014/0144969, entitled "Pivoting Anvil for Surgical Circular Stapler," published May 29, 2014, issued as U.S. Pat. No. 9,498,222 on Nov. 22, 2016, the disclosure of which is incorporated by reference herein; U.S. Pub. No. 2014/0151430, entitled "Circular Anvil Introduction System with Alignment Feature," published Jun. 5, 2014, issued as U.S. Pat. No. 9,724,100 on Aug. 8, 2017, the disclosure of which is incorporated by reference herein; U.S. Pub. No. 2014/0166717, entitled "Circular Stapler with Selectable Motorized and Manual Control, Including a Control Ring," published Jun. 19, 2014, issued as U.S. Pat. No. 9,532,783 on Jan. 3, 2017, the disclosure of which is incorporated by reference herein; U.S. Pub. No. 2014/0166728, entitled "Motor Driven Rotary Input Circular Stapler with Modular End Effector," published Jun. 19, 2014, issued as U.S. Pat. No. 9,597,081 on Mar. 21, 2017, the disclosure of which is incorporated by reference herein; and/or U.S. Pub. No. 2014/0166718, entitled "Motor Driven Rotary Input Circular Stapler with Lockable Flexible Shaft," published Jun. 19, 2014, issued as U.S. Pat. No. 9,463,022 on Oct. 11, 2016, the disclosure of which is incorporated by reference herein. Various suitable ways in which such teachings may be combined will be apparent to those of ordinary skill in the art.

While the examples herein have been provided in the context of a circular stapling instrument, it should be understood that the various teachings herein may be readily applied to various other kinds of surgical instruments. By way of example only, the various teachings herein may be readily applied to linear stapling devices (e.g., endocutters). For instance, various teachings herein may be readily combined with various teachings of U.S. Pub. No. 2012/0239012, entitled "Motor-Driven Surgical Cutting Instrument with Electric Actuator Directional Control Assembly," published Sep. 20, 2012, issued as U.S. Pat. No. 8,453,914 on Jun. 4, 2013, the disclosure of which is incorporated by reference herein, and/or U.S. Pub. No. 2010/0264193, entitled "Surgical Stapling Instrument with An Articulatable End Effector," published Oct. 21, 2010, issued as U.S. Pat. No. 8,408,439 on Apr. 2, 2013, the disclosure of which is incorporated by reference herein, as will be apparent to those of ordinary skill in the art. As another merely illustrative example, the various teachings herein may be readily applied to a motorized electrosurgical device. For instance, various teachings herein may be readily combined with various teachings of U.S. Pub. No. 2012/0116379, entitled "Motor Driven Electrosurgical Device with Mechanical and Electrical Feedback," published May 10, 2012, issued as U.S. Pat. No. 9,161,803 on Oct. 20, 2015, the disclosure of which is incorporated by reference herein, as will be apparent to those of ordinary skill in the art. Other suitable kinds of instruments in which the teachings herein may be applied, and various ways in which the teachings herein may be applied to such instruments, will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A surgical instrument comprising:
   (a) a body;
   (b) a shaft assembly extending distally from the body, wherein the shaft assembly comprises a distal end;
   (c) a stapling head assembly located at the distal end of the shaft assembly, wherein the stapling head assembly comprises a distal surface, wherein the stapling head assembly is operable to drive an annular array of staples through the distal surface;
   (d) an anvil, wherein the anvil is configured to couple with the stapling head assembly;
   (e) an anvil adjustment assembly, wherein the anvil adjustment assembly comprises a translating member, wherein the translating member is operable to translate relative to the body along a longitudinal axis to thereby adjust the longitudinal position of the anvil relative to the distal surface of the stapling head assembly;
   (f) a first trigger, wherein the first trigger is operable to actuate the stapling head assembly to thereby drive the annular array of staples through the distal surface toward the anvil; and
   (g) a lockout assembly, wherein the lockout assembly comprises a braking feature and an electrical drive, wherein the lockout assembly is configured to transition between a first state and a second state, wherein:
      (i) in the first state, the braking feature is configured to permit translation of the translating member, and
      (ii) in the second state, the braking feature is configured to prevent translation of the translating member, wherein the electrical drive is configured to actuate the braking feature into the second state.

2. The surgical instrument of claim 1, wherein the electrical drive comprises a solenoid.

3. The surgical instrument of claim 2, wherein the lockout assembly further comprises a second trigger, wherein the second trigger is movable between a non-actuated position and an actuated position, wherein the second trigger is operable to provide the solenoid in a non-activated state in response to the second trigger being in the non-actuated position, wherein the second trigger is further operable to provide the solenoid in an activated state in response to the second trigger being in the actuated position.

4. The surgical instrument of claim 2, wherein the braking feature further comprises a lock member, wherein the solenoid is operable to selectively drive the lock member into engagement with the translating member to thereby prevent translation of the translating member.

5. The surgical instrument of claim 4, wherein the translating member comprises a laterally presented array of teeth, wherein the lock member comprises an array of teeth, wherein the solenoid is operable to selectively drive the teeth of the lock member into engagement with the teeth of the translating member to thereby prevent translation of the translating member.

6. The surgical instrument of claim 4, wherein the solenoid is operable to selectively drive the lock member along a path that is transverse to the longitudinal axis to thereby drive the lock member into engagement with the translating member to thereby prevent translation of the translating member.

7. The surgical instrument of claim 4, wherein the anvil adjustment assembly comprises an annularly arranged array of teeth, wherein the lock member comprises an angularly arranged array of teeth, wherein the solenoid is operable to selectively drive the teeth of the lock member into engagement with the teeth of the anvil adjustment assembly to thereby prevent translation of the translating member.

8. The surgical instrument of claim 7, wherein the anvil adjustment assembly further comprises a rotary member, wherein the translating member is coupled with the rotary member, wherein the rotary member is operable to drive the translating member longitudinally in response to rotation of the rotary member, wherein the angularly arranged array of teeth are secured to the rotary member such that the teeth of the lock member are operable to prevent rotation of the rotary member to thereby prevent translation of the translating member.

9. The surgical instrument of claim 4, wherein the solenoid is operable to selectively drive the lock member along a path that is parallel to the longitudinal axis to thereby drive the lock member into engagement with the translating member to thereby prevent translation of the translating member.

10. The surgical instrument of claim 1, wherein when the braking feature is in the first state, the lockout assembly is further configured to prevent actuation of the first trigger, and wherein when the braking feature is in the second state, the lockout assembly is further configured to permit actuation of the first trigger.

11. The surgical instrument of claim 10, wherein the lockout assembly further comprises a second trigger, wherein the second trigger is movable between a non-actuated position and an actuated position, wherein the second trigger is operable to provide the lockout assembly in the first state in response to the second trigger being in the non-actuated position, wherein the second trigger is further operable to provide the lockout assembly in the second state in response to the second trigger being in the actuated position, wherein the first trigger is movable from an actuated position to a non-actuated position, wherein the first trigger is configured to drive the second trigger from the actuated position toward the non-actuated position in response to the first trigger being driven from the actuated position toward the non-actuated position.

12. The surgical instrument of claim 1, wherein the lockout assembly is inoperable to transition the braking feature from the first state to the second state until the anvil is within a predetermined range of distance from the distal surface of the stapling head assembly.

13. The surgical instrument of claim 12, further comprising a blocking member, wherein the anvil adjustment assembly is operable to drive the blocking member based on the position of the anvil relative to the distal surface of the stapling head assembly, wherein the blocking member is configured to selectively block a portion of the lockout assembly to thereby prevent the lockout assembly from transitioning from the first state to the second state.

14. The surgical instrument of claim 1, further comprising a motor positioned in the body, wherein the motor is operable to actuate the stapling head assembly in response to actuation of the first trigger.

15. The surgical instrument of claim 1, wherein the body defines a socket configured to receive a battery pack, wherein the lockout assembly is configured to be in the first state in response to a battery pack being inserted in the socket, wherein the lockout assembly is configured to be in the second state in response to the absence of a battery pack from the socket.

16. A surgical instrument comprising:
(a) a stapling head assembly, wherein the stapling head assembly comprises a plurality of staples;
(b) a clamping member, wherein the clamping member comprises a plurality of staple forming features;
(c) a clamping drive assembly, wherein the clamping drive assembly is operable to drive the clamping member toward and away from the stapling head assembly;
(d) a firing assembly, wherein the firing assembly is operable to actuate the stapling head assembly to thereby drive the staples toward the staple forming features; and
(e) a lockout assembly comprising an engagement feature and an electrical actuator configured to drive the engagement feature, wherein the electrical actuator is operable to selectively drive the engagement feature to lock the clamping drive assembly and thereby prevent actuation of the clamping drive assembly in response to a first operational condition, wherein the lockout assembly is further operable to selectively lock the clamping drive assembly and thereby prevent actuation of the clamping drive assembly in response to a second operational condition, wherein the second operational condition is different from the first operational condition.

17. The surgical instrument of claim 16, wherein the firing assembly comprises a first trigger, wherein the first condition comprises actuation of the first trigger such that the lockout assembly is operable to selectively lock the clamping drive assembly and thereby prevent actuation of the clamping drive assembly in response to actuation of the first trigger.

18. The surgical instrument of claim 17, wherein the firing assembly further comprises a second trigger, wherein the second trigger is configured to activate the firing assembly to thereby actuate the stapling head assembly to thereby drive the staples toward the staple forming features, wherein the first trigger is configured to selectively prevent actuation of the second trigger.

19. The surgical instrument of claim 17, further comprising a power source coupling feature, wherein the power source coupling feature is configured to couple with a power source to thereby provide electrical power to the firing assembly, wherein the second condition comprises the absence of a power source from the power source coupling feature such that the lockout assembly is operable to selectively lock the clamping drive assembly and thereby prevent actuation of the clamping drive assembly in response to the absence of a power source from the power source coupling feature.

20. A surgical instrument comprising:
(a) a stapling head assembly, wherein the stapling head assembly comprises a plurality of staples;
(b) a clamping member, wherein the clamping member comprises a plurality of staple forming features;
(c) a clamping drive assembly, wherein the clamping drive assembly is operable to drive the clamping member toward and away from the stapling head assembly;
(d) a firing assembly, wherein the firing assembly is operable to actuate the stapling head assembly to thereby drive the staples toward the staple forming features;

(e) a first lockout assembly, wherein the first lockout assembly is configured to prevent actuation of the firing assembly unless the clamping member is within a predefined range of distance from the stapling head assembly; and (f) a second lockout assembly, wherein the second lockout assembly is configured to prevent actuation of the clamping drive assembly during activation of the firing assembly, wherein the second lockout assembly comprises an electrically activated actuator and an engagement feature, wherein the electrically activated actuator is configured to actuate the engagement feature in order to prevent actuation of the clamping drive assembly.

* * * * *